United States Patent
Sanghera et al.

(10) Patent No.: US 11,666,771 B2
(45) Date of Patent: Jun. 6, 2023

(54) IMPLANTABLE ELECTRICAL LEADS AND ASSOCIATED DELIVERY SYSTEMS

(71) Applicant: ATACOR MEDICAL, INC., San Clemente, CA (US)

(72) Inventors: Rick Sanghera, San Clemente, CA (US); Brent Cadavona, San Diego, CA (US); Matthew Rollins, Lafayette, CO (US); Tim Searfoss, New Port Richey, FL (US); Brian Walguarnery, Tampa, FL (US); Michel Gelineau, Hudson, FL (US)

(73) Assignee: ATACOR MEDICAL, INC., San Clemente, CA (US)

(*) Notice: Subject to any disclaimer, the term of this patent is extended or adjusted under 35 U.S.C. 154(b) by 230 days.

(21) Appl. No.: 17/106,152

(22) Filed: Nov. 29, 2020

(65) Prior Publication Data

US 2021/0370080 A1 Dec. 2, 2021

Related U.S. Application Data

(63) Continuation-in-part of application No. 16/888,462, filed on May 29, 2020.

(Continued)

(51) Int. Cl.
*A61N 1/05* (2006.01)
*A61N 1/39* (2006.01)

(52) U.S. Cl.
CPC ......... *A61N 1/39622* (2017.08); *A61N 1/059* (2013.01); *A61N 1/0597* (2013.01)

(58) Field of Classification Search
CPC .................. A61N 1/059; A61N 1/0597; A61N 1/39622
See application file for complete search history.

(56) References Cited

U.S. PATENT DOCUMENTS

| 2,003,007 A | 5/1935 | Olive |
| 3,416,534 A | 12/1968 | Quinn |

(Continued)

FOREIGN PATENT DOCUMENTS

| EP | 0668087 | 8/1995 |
| EP | 1530983 A2 | 5/2005 |

(Continued)

OTHER PUBLICATIONS

Brown, Charles G., et. al. 'Injuries Associated with Percutaneous Placement of Transthoracic Pacemakers.' Annals of Emergency Medicine 14.3 (1985): 223-28.

(Continued)

*Primary Examiner* — Eric D. Bertram
(74) *Attorney, Agent, or Firm* — Pillsbury Winthrop Shaw Pittman LLP

(57) ABSTRACT

Disclosed is a delivery system for a component, for example, a splitting lead. A splitting lead can have a proximal portion to engage a controller and a distal portion to split apart into sub-portions that travel in multiple directions during implantation into a patient. The delivery system can include a handle and a component advancer to advance and removably engage a portion of the component. The component advancer can be coupled to the handle and advance the component into the patient by applying a force to the portion in response to actuation of the handle by the operator. Also, the delivery system can include an insertion tip with first and second ramps to facilitate advancement of first and second sub-portions into the patient in first and second directions. The leads may have various electrode configurations including, for example, wrapped or embedded electrodes, helical or elliptical coils, thin metallic plates, etc.

57 Claims, 46 Drawing Sheets

Related U.S. Application Data

(60) Provisional application No. 63/049,561, filed on Jul. 8, 2020.

(56) References Cited

U.S. PATENT DOCUMENTS

| | | |
|---|---|---|
| 3,485,247 A | 12/1969 | Ackerman |
| 4,030,509 A | 6/1977 | Heilman |
| 4,146,037 A | 3/1979 | Flynn |
| 4,270,549 A | 6/1981 | Heilman |
| 4,280,510 A | 7/1981 | ONeill |
| 4,291,707 A | 9/1981 | Heilman |
| 4,306,560 A | 12/1981 | Harris |
| 4,437,475 A | 3/1984 | White |
| 4,512,351 A | 4/1985 | Pohndorf |
| 4,532,931 A | 8/1985 | Mills |
| 4,538,624 A | 9/1985 | Tarjan |
| 4,636,199 A | 1/1987 | Victor |
| 4,664,120 A * | 5/1987 | Hess ............... A61N 1/056 600/374 |
| 4,765,341 A | 8/1988 | Mower |
| 4,787,389 A | 11/1988 | Tarjan |
| 4,832,687 A | 5/1989 | Smith, III |
| 4,846,191 A | 7/1989 | Brockway |
| 4,865,037 A | 9/1989 | Chin |
| 5,036,854 A | 8/1991 | Schollmeyer |
| 5,125,904 A | 6/1992 | Lee |
| 5,129,394 A | 7/1992 | Mehra |
| 5,176,135 A | 1/1993 | Fain |
| 5,203,348 A | 4/1993 | Dahl |
| 5,255,691 A | 10/1993 | Otten |
| 5,255,692 A | 10/1993 | Neubauer |
| 5,273,053 A | 12/1993 | Pohndorf |
| 5,300,106 A | 4/1994 | Dahl |
| 5,312,355 A | 5/1994 | Lee |
| 5,336,252 A | 8/1994 | Cohen |
| 5,364,361 A | 11/1994 | Battenfield |
| 5,391,156 A | 2/1995 | Hildwein |
| 5,441,504 A | 8/1995 | Pohndorf |
| 5,456,699 A | 10/1995 | Armstrong |
| 5,476,493 A | 12/1995 | Muff |
| 5,509,924 A | 4/1996 | Paspa |
| 5,534,018 A | 7/1996 | Wahlstrand |
| 5,545,205 A | 8/1996 | Schulte |
| 5,562,677 A | 10/1996 | Hildwein |
| 5,571,215 A | 11/1996 | Sterman |
| 5,613,953 A | 3/1997 | Pohndorf |
| 5,690,648 A | 11/1997 | Fogarty |
| 5,716,392 A | 2/1998 | Bourgeois |
| 5,728,151 A | 3/1998 | Garrison |
| 5,752,526 A | 5/1998 | Cosgrove |
| 5,752,970 A | 5/1998 | Yoon |
| 5,776,110 A | 7/1998 | Guy |
| 5,814,076 A | 9/1998 | Brownlee |
| 5,823,946 A | 10/1998 | Chin |
| 5,830,214 A | 11/1998 | Flom |
| 5,871,532 A | 2/1999 | Schroeppel |
| 5,895,414 A | 4/1999 | Sanchez-Zambrano |
| 5,904,711 A | 5/1999 | Flom |
| 5,941,819 A | 8/1999 | Chin |
| 5,944,732 A | 8/1999 | Raulerson |
| 5,951,518 A | 9/1999 | Licata |
| 6,024,704 A | 2/2000 | Meador |
| 6,032,079 A | 2/2000 | KenKnight |
| 6,076,012 A * | 6/2000 | Swanson ............... A61N 1/06 606/41 |
| 6,099,547 A | 8/2000 | Gellman |
| 6,104,957 A | 8/2000 | Alo |
| 6,122,552 A | 9/2000 | Tockman |
| 6,159,198 A | 12/2000 | Gardeski |
| 6,228,052 B1 | 5/2001 | Pohndorf |
| 6,251,418 B1 | 6/2001 | Ahern |
| 6,283,127 B1 | 9/2001 | Sterman |
| 6,324,414 B1 | 11/2001 | Gibbons |
| 6,415,187 B1 | 7/2002 | Kuzma |
| 6,445,954 B1 | 9/2002 | Olive |
| 6,478,028 B1 | 11/2002 | Paolitto |
| 6,497,651 B1 | 12/2002 | Kan |
| 6,544,247 B1 | 4/2003 | Gardeski |
| 6,651,672 B2 | 11/2003 | Roth |
| 6,706,052 B1 | 3/2004 | Chin |
| 6,718,203 B2 | 4/2004 | Weiner |
| 6,721,597 B1 | 4/2004 | Bardy |
| 6,730,083 B2 | 5/2004 | Freigang |
| 6,733,500 B2 | 5/2004 | Kelley |
| 6,749,574 B2 | 6/2004 | OKeefe |
| 6,770,070 B1 | 8/2004 | Balbierz |
| 6,772,014 B2 | 8/2004 | Coe |
| 6,836,687 B2 | 12/2004 | Kelley |
| 6,866,044 B2 | 3/2005 | Bardy |
| 6,868,291 B1 | 3/2005 | Bonner |
| 6,887,229 B1 | 5/2005 | Kurth |
| 6,889,093 B1 * | 5/2005 | Flammang ............ A61N 1/3918 607/122 |
| 6,890,295 B2 | 5/2005 | Michels |
| 6,918,908 B2 | 7/2005 | Bonner |
| 6,999,819 B2 | 2/2006 | Swoyer |
| 7,033,326 B1 | 4/2006 | Pianca |
| 7,050,851 B2 | 5/2006 | Plombon |
| 7,069,083 B2 | 6/2006 | Finch |
| 7,096,064 B2 | 8/2006 | Deno |
| 7,117,039 B2 | 10/2006 | Manning |
| 7,120,496 B2 | 10/2006 | Bardy |
| 7,149,575 B2 | 12/2006 | Ostroff |
| 7,191,015 B2 | 3/2007 | Lamson |
| 7,195,637 B2 | 3/2007 | Mika |
| 7,218,970 B2 | 5/2007 | Ley |
| 7,229,450 B1 | 6/2007 | Chitre |
| 7,239,925 B2 | 7/2007 | Bardy |
| 7,272,448 B1 | 9/2007 | Morgan |
| 7,288,096 B2 | 10/2007 | Chin |
| 7,316,667 B2 | 1/2008 | Lindstrom |
| 7,319,905 B1 | 1/2008 | Morgan |
| 7,322,960 B2 | 1/2008 | Yamamoto |
| 7,353,067 B1 | 4/2008 | Helland |
| 7,369,899 B2 | 5/2008 | Malinowski |
| 7,373,207 B2 | 5/2008 | Lattouf |
| 7,389,134 B1 | 6/2008 | Karicherla |
| 7,398,781 B1 | 7/2008 | Chin |
| 7,450,997 B1 | 11/2008 | Pianca |
| 7,496,408 B2 | 2/2009 | Ghanem |
| 7,499,758 B2 | 3/2009 | Cates |
| 7,515,969 B2 | 4/2009 | Tockman |
| 7,539,542 B1 | 5/2009 | Malinowski |
| 7,627,375 B2 | 12/2009 | Bardy |
| 7,655,014 B2 | 2/2010 | Ko |
| 7,736,330 B2 | 6/2010 | Bardy |
| 7,751,885 B2 | 7/2010 | Bardy |
| 7,761,150 B2 | 7/2010 | Ghanem |
| 7,765,014 B2 | 7/2010 | Eversull |
| 7,801,622 B2 | 9/2010 | Camps |
| 7,837,671 B2 | 11/2010 | Eversull |
| 7,846,088 B2 | 12/2010 | Ness |
| 7,850,610 B2 | 12/2010 | Ferek-Petric |
| 7,890,191 B2 | 2/2011 | Rutten |
| 7,908,015 B2 | 3/2011 | Lazeroms |
| 7,930,028 B2 | 4/2011 | Lang |
| 7,930,040 B1 | 4/2011 | Kelsch |
| 7,967,833 B2 | 6/2011 | Sterman |
| 7,983,765 B1 | 7/2011 | Doan |
| 8,060,207 B2 | 11/2011 | Wallace |
| 8,065,020 B2 | 11/2011 | Ley |
| 8,066,702 B2 | 11/2011 | Rittman, III |
| 8,090,451 B2 | 1/2012 | Tyson, Jr. |
| 8,155,755 B2 | 4/2012 | Flynn |
| 8,157,813 B2 | 4/2012 | Ko |
| 8,260,436 B2 | 9/2012 | Gerber |
| 8,280,527 B2 | 10/2012 | Eckerdal |
| 8,332,036 B2 | 12/2012 | Hastings |
| 8,340,779 B2 | 12/2012 | Harris |
| 8,355,786 B2 | 1/2013 | Malinowski |
| 8,386,052 B2 | 2/2013 | Harris |
| 8,394,079 B2 | 3/2013 | Drake |
| 8,435,208 B2 | 5/2013 | Bardy |

(56) References Cited

U.S. PATENT DOCUMENTS

| | | |
|---|---|---|
| 8,442,620 B2 | 5/2013 | Silipo |
| 8,452,421 B2 | 5/2013 | Thenuwara |
| 8,454,552 B2 | 6/2013 | Bardy |
| 8,457,742 B2 | 6/2013 | Jacobson |
| 8,478,424 B2 | 7/2013 | Tronnes |
| 8,478,426 B2 | 7/2013 | Barker |
| 8,478,431 B2 | 7/2013 | Griswold |
| 8,483,841 B2 | 7/2013 | Sanghera |
| 8,532,789 B2 | 9/2013 | Smits |
| 8,594,809 B2 | 11/2013 | Yang |
| 8,886,311 B2 | 11/2014 | Anderson |
| 9,079,035 B2 | 7/2015 | Sanghera |
| 9,468,754 B2 | 10/2016 | Martinez |
| 9,622,778 B2 | 4/2017 | Wengreen |
| 9,636,505 B2 | 5/2017 | Sanghera |
| 9,636,512 B2 | 5/2017 | Cinbis |
| 9,707,389 B2 | 7/2017 | McGeehan |
| 9,757,190 B2 | 9/2017 | Evans |
| 9,855,414 B2 | 1/2018 | Marshall |
| 10,080,905 B2 | 9/2018 | Anderson |
| 10,130,824 B2 | 11/2018 | Grinberg |
| 10,137,295 B2 | 11/2018 | Marshall |
| 10,471,267 B2 | 11/2019 | Thompson-Nauman |
| 10,532,203 B2 | 1/2020 | Thompson-Nauman |
| 10,661,073 B2 | 5/2020 | Marshall |
| 10,722,704 B2 | 7/2020 | Min |
| 10,758,228 B2 | 9/2020 | Zenz-Olson |
| 10,842,998 B2 | 11/2020 | Keefe |
| 10,881,850 B2 | 1/2021 | Baudino |
| 2002/0035381 A1 | 3/2002 | Bardy |
| 2002/0035388 A1 | 3/2002 | Lindemans |
| 2002/0042629 A1 | 4/2002 | Bardy |
| 2002/0120294 A1 | 8/2002 | Kroll |
| 2002/0143380 A1 | 10/2002 | Dahl |
| 2003/0045904 A1 | 3/2003 | Bardy |
| 2003/0074041 A1 | 4/2003 | Parry |
| 2003/0088278 A1 | 5/2003 | Bardy |
| 2003/0097153 A1 | 5/2003 | Bardy |
| 2003/0114905 A1 | 6/2003 | Kuzma |
| 2003/0114906 A1 | 6/2003 | Booker |
| 2003/0114908 A1 | 6/2003 | Flach |
| 2003/0120264 A1 | 6/2003 | Lattouf |
| 2003/0130581 A1 | 7/2003 | Salo |
| 2003/0187458 A1 | 10/2003 | Carlson |
| 2003/0208153 A1 | 11/2003 | Stenzel |
| 2004/0059348 A1 | 3/2004 | Geske |
| 2004/0064176 A1 | 4/2004 | Min |
| 2004/0088035 A1 | 5/2004 | W |
| 2004/0102829 A1 | 5/2004 | Bonner |
| 2004/0143284 A1 | 7/2004 | Chin |
| 2004/0158185 A1 | 8/2004 | Moran |
| 2004/0210293 A1 | 10/2004 | Bardy |
| 2004/0215240 A1 | 10/2004 | Lovett |
| 2004/0230282 A1 | 11/2004 | Cates |
| 2004/0236396 A1 | 11/2004 | Coe |
| 2005/0027328 A1 | 2/2005 | Greenstein |
| 2005/0049663 A1 | 3/2005 | Harris |
| 2005/0131505 A1 | 6/2005 | Yokoyama |
| 2005/0165324 A1 | 7/2005 | Receveur |
| 2005/0192639 A1 | 9/2005 | Bardy |
| 2005/0288731 A1 | 12/2005 | Shames |
| 2005/0288758 A1 | 12/2005 | Jones |
| 2006/0041295 A1 | 2/2006 | Osypka |
| 2006/0047333 A1 | 3/2006 | Tockman |
| 2006/0085039 A1 | 4/2006 | Hastings |
| 2006/0089699 A1 | 4/2006 | Imran |
| 2006/0116746 A1 | 6/2006 | Chin |
| 2006/0122676 A1 | 6/2006 | Ko |
| 2006/0129202 A1 | 6/2006 | Armstrong |
| 2006/0136004 A1 | 6/2006 | Cowan |
| 2006/0161205 A1 | 7/2006 | Mitrani |
| 2006/0241711 A1 | 10/2006 | Sathaye |
| 2006/0247672 A1 | 11/2006 | Vidlund |
| 2006/0247753 A1 | 11/2006 | Wenger |
| 2006/0253181 A1 | 11/2006 | Schulman |
| 2006/0266368 A1 | 11/2006 | Heintz |
| 2007/0023947 A1 | 2/2007 | Ludwig |
| 2007/0088394 A1 | 4/2007 | Jacobson |
| 2007/0100409 A1 | 5/2007 | Worley |
| 2007/0150015 A1 | 6/2007 | Zhang |
| 2007/0150023 A1 | 6/2007 | Ignagni |
| 2007/0179388 A1 | 8/2007 | Larik |
| 2007/0197859 A1 | 8/2007 | Schaer |
| 2007/0208402 A1 | 9/2007 | Helland |
| 2007/0249992 A1 | 10/2007 | Bardy |
| 2008/0021505 A1 | 1/2008 | Hastings |
| 2008/0027488 A1 | 1/2008 | Coles |
| 2008/0039866 A1 | 2/2008 | Stetz |
| 2008/0046056 A1 | 2/2008 | OConnor |
| 2008/0103575 A1 | 5/2008 | Gerber |
| 2008/0183230 A1 | 7/2008 | Kemmetmueller |
| 2008/0183254 A1 | 7/2008 | Bly |
| 2008/0242976 A1 | 10/2008 | Robertson |
| 2008/0243196 A1 | 10/2008 | Libbus |
| 2008/0243219 A1 | 10/2008 | Malinowski |
| 2008/0269716 A1 | 10/2008 | Bonde |
| 2008/0294217 A1 | 11/2008 | Lian |
| 2008/0300644 A1 | 12/2008 | Sathaye |
| 2009/0054947 A1 | 2/2009 | Bourn |
| 2009/0069803 A1 | 3/2009 | Starkebaum |
| 2009/0157091 A1 | 6/2009 | Buysman |
| 2009/0209970 A1 | 8/2009 | Tanaka |
| 2009/0222021 A1 | 9/2009 | Chang |
| 2009/0259283 A1 | 10/2009 | Brandt |
| 2009/0264780 A1 | 10/2009 | Schilling |
| 2009/0270962 A1 | 10/2009 | Yang |
| 2009/0326346 A1 | 12/2009 | Kracker |
| 2010/0016935 A1 | 1/2010 | Strandberg |
| 2010/0030227 A1 | 2/2010 | Kast |
| 2010/0030228 A1 | 2/2010 | Havel |
| 2010/0056858 A1 | 3/2010 | Mokelke |
| 2010/0082087 A1 | 4/2010 | Silipo |
| 2010/0094252 A1 | 4/2010 | Wengreen |
| 2010/0113963 A1 | 5/2010 | Smits |
| 2010/0125194 A1 | 5/2010 | Bonner |
| 2010/0137879 A1 | 6/2010 | Ko |
| 2010/0152747 A1 | 6/2010 | Padiy |
| 2010/0152798 A1 | 6/2010 | Sanghera |
| 2010/0152799 A1 | 6/2010 | Sanghera |
| 2010/0185268 A1 | 7/2010 | Fowler |
| 2010/0211064 A1 | 8/2010 | Mahapatra |
| 2010/0217298 A1 | 8/2010 | Bardy |
| 2010/0217301 A1 | 8/2010 | Bardy |
| 2010/0241189 A1 | 9/2010 | Dobak |
| 2010/0305428 A1 | 12/2010 | Bonner |
| 2010/0318098 A1 | 12/2010 | Lund |
| 2010/0324579 A1 | 12/2010 | Bardy |
| 2010/0331868 A1 | 12/2010 | Bardy |
| 2010/0331938 A1 | 12/2010 | Sommer |
| 2011/0009933 A1 | 1/2011 | Barker |
| 2011/0024491 A1 | 2/2011 | Jamali |
| 2011/0066185 A1 | 3/2011 | Wotton, III |
| 2011/0077708 A1 | 3/2011 | Ostroff |
| 2011/0125163 A1 | 5/2011 | Rutten |
| 2011/0152706 A1 | 6/2011 | Christopherson |
| 2011/0178566 A1 | 7/2011 | Stahmann |
| 2011/0210156 A1 | 9/2011 | Smith |
| 2011/0224680 A1 | 9/2011 | Barker |
| 2011/0224681 A1 | 9/2011 | McDonald |
| 2011/0230906 A1 | 9/2011 | Modesitt |
| 2011/0257660 A1 | 10/2011 | Jones |
| 2012/0016377 A1 | 1/2012 | Geroy |
| 2012/0029335 A1 | 2/2012 | Sudam |
| 2012/0035697 A1 | 2/2012 | Stone |
| 2012/0037291 A1 | 2/2012 | Goolishian |
| 2012/0078266 A1 | 3/2012 | Tyson |
| 2012/0089153 A1 | 4/2012 | Christopherson |
| 2012/0097174 A1 | 4/2012 | Spotnitz |
| 2012/0109250 A1 | 5/2012 | Cates |
| 2012/0123496 A1 | 5/2012 | Schotzko |
| 2012/0191106 A1 | 7/2012 | Ko |
| 2012/0209283 A1 | 8/2012 | Zhu |
| 2012/0209298 A1 | 8/2012 | McClurg |
| 2012/0245433 A1 | 9/2012 | Ahern |

(56) References Cited

U.S. PATENT DOCUMENTS

| | | |
|---|---|---|
| 2012/0302863 A1 | 11/2012 | O'Neill |
| 2013/0006326 A1 | 1/2013 | Ackermann |
| 2013/0041345 A1 | 2/2013 | Kilcoin |
| 2013/0103049 A1 | 4/2013 | Bonde |
| 2013/0158564 A1 | 6/2013 | Harris |
| 2013/0178711 A1 | 7/2013 | Avneri |
| 2013/0226266 A1 | 8/2013 | Murtonen |
| 2013/0237781 A1 | 9/2013 | Gyrn |
| 2013/0238067 A1 | 9/2013 | Baudino |
| 2013/0296880 A1 | 11/2013 | Kelley |
| 2013/0338707 A1 | 12/2013 | Killion |
| 2014/0005755 A1 | 1/2014 | Wolf, II |
| 2014/0018872 A1 | 1/2014 | Siejko |
| 2014/0180273 A1 | 6/2014 | Nair |
| 2014/0243844 A1 | 8/2014 | Clancy |
| 2014/0257421 A1 | 9/2014 | Sanghera |
| 2014/0330208 A1 | 11/2014 | Christie |
| 2014/0330248 A1 | 11/2014 | Thompson-Nauman |
| 2014/0330287 A1 | 11/2014 | Thompson-Nauman |
| 2014/0330325 A1 | 11/2014 | Thompson-Nauman |
| 2014/0330326 A1 | 11/2014 | Thompson-Nauman |
| 2014/0330327 A1 | 11/2014 | Thompson-Nauman |
| 2014/0330328 A1 | 11/2014 | Christie |
| 2014/0330329 A1 | 11/2014 | Thompson-Nauman |
| 2014/0330331 A1 | 11/2014 | Thompson-Nauman |
| 2015/0013689 A1 | 1/2015 | Shackelford |
| 2015/0051612 A1 | 2/2015 | Schmidt |
| 2015/0051615 A1 | 2/2015 | Schmidt |
| 2015/0088155 A1 | 3/2015 | Stahmann |
| 2015/0133954 A1 | 5/2015 | Seifert |
| 2015/0142069 A1 | 5/2015 | Sambelashvili |
| 2015/0151114 A1 | 6/2015 | Black |
| 2015/0157497 A1 | 6/2015 | Hufford |
| 2015/0223906 A1 | 8/2015 | O'Neill |
| 2015/0313633 A1 | 11/2015 | Gross |
| 2015/0328473 A1 | 11/2015 | Bodner |
| 2016/0051159 A1 | 2/2016 | Mazaeva |
| 2016/0067478 A1 | 3/2016 | McGeehan |
| 2016/0067479 A1 | 3/2016 | Marcovecchio |
| 2016/0067480 A1 | 3/2016 | Sanghera |
| 2016/0067488 A1 | 3/2016 | Sanghera |
| 2016/0144192 A1 | 5/2016 | Sanghera |
| 2016/0175007 A1 | 6/2016 | Valbuena |
| 2016/0175581 A1 | 6/2016 | Gordon |
| 2016/0184047 A1 | 6/2016 | Weir |
| 2017/0224995 A1 | 8/2017 | Sanghera |
| 2017/0259078 A1* | 9/2017 | Howard ............... A61N 5/0622 |
| 2017/0304019 A1 | 10/2017 | Sanghera |
| 2017/0304634 A1 | 10/2017 | Sanghera |
| 2018/0021572 A1 | 1/2018 | McGeehan |
| 2018/0028804 A1 | 2/2018 | Pianca |
| 2018/0050199 A1 | 2/2018 | Sanghera |
| 2018/0193060 A1 | 7/2018 | Reddy |
| 2019/0105489 A1 | 4/2019 | Thompson-Nauman |
| 2020/0376265 A1 | 12/2020 | Sanghera |
| 2020/0398044 A1 | 12/2020 | Sanghera |
| 2021/0113295 A1 | 4/2021 | Sanghera |

FOREIGN PATENT DOCUMENTS

| | | |
|---|---|---|
| EP | 2346419 | 7/2011 |
| EP | 2464418 | 6/2012 |
| EP | 2967644 | 1/2016 |
| EP | 2994193 | 3/2016 |
| EP | 2994194 | 3/2016 |
| EP | 3173043 | 5/2017 |
| EP | 3429686 | 1/2019 |
| WO | 2002026315 A1 | 4/2002 |
| WO | 2006115772 A2 | 11/2006 |
| WO | 2009148941 | 12/2009 |
| WO | 2013163267 A1 | 10/2013 |
| WO | 2015143327 | 9/2015 |
| WO | 2017198472 | 11/2017 |
| WO | 2018009913 | 1/2018 |

OTHER PUBLICATIONS

Brown, Charles G., et. al. 'Placement Accuracy of Percutaneous Transthoracic Pacemakers.' The American Journal of Emergency Medicine 3.3 (1985): 193-98.

International Search Report and Written Opinion dated Sep. 21, 2020, International Application No. PCT/US2020/035268; (10 pages).

Nagdev, Arun, and Daniel Mantuani. 'A Novel In-plane Technique for Ultrasound-guided Pericardiocentesis.' Tlie American Journal of Emergency Medicine 31.9 (2013): 1424.e5-1424.e9.

Notice of Allowance dated Apr. 13, 2020 for U.S. Appl. No. 15/644,714 (pp. 1-9).

Office Action dated Feb. 28, 2020 for U.S. Appl. No. 14/846,578 (pp. 1-8).

Office Action dated May 14, 2020 for U.S. Appl. No. 16/267,255 (pp. 1-8).

Office Action dated Nov. 10, 2020 for U.S. Appl. No. 16/409,200 (pp. 1-6).

Office Action dated Nov. 2, 2020 for U.S. Appl. No. 16/267,255 (pp. 1-12).

Pai, N. V., et. al. 'Relation of Internal Thoracic Artery to Lateral Sternal Border and Its Significance in Clinical Procedures.' International Journal of Biological & Medical Research 4.4 (2013): 3633-636.

PCT/US2017/041265; International Search Report and Written Opinion dated Sep. 25, 2017; 11 pages.

International Search Report and Written Opinion dated Jan. 24, 2022, International application No. PCT/IB2021/056065.

* cited by examiner

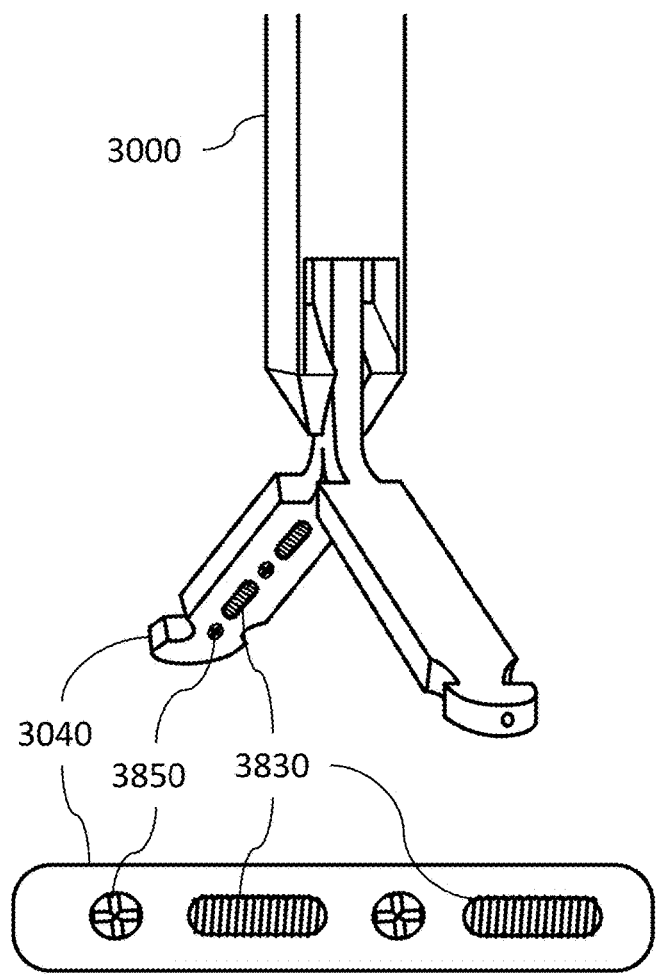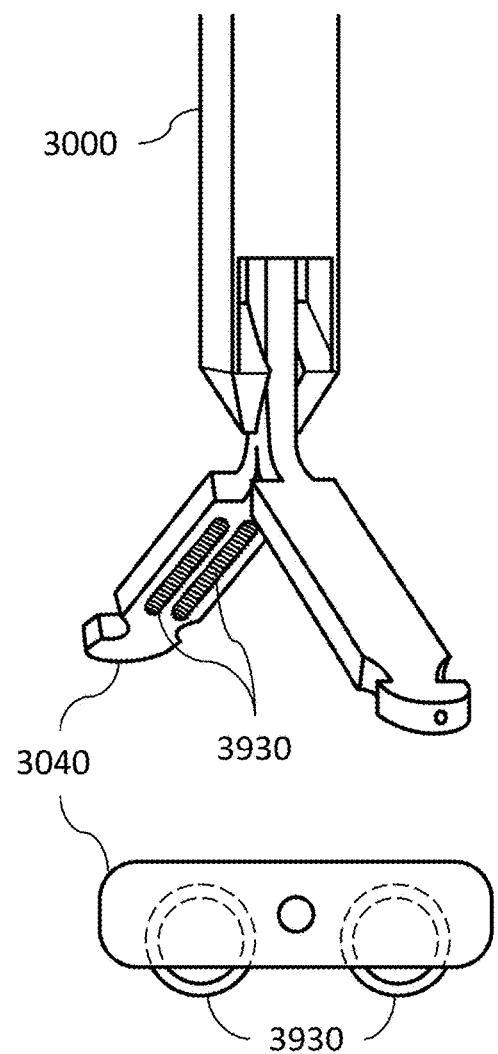
FIG. 38  FIG. 39

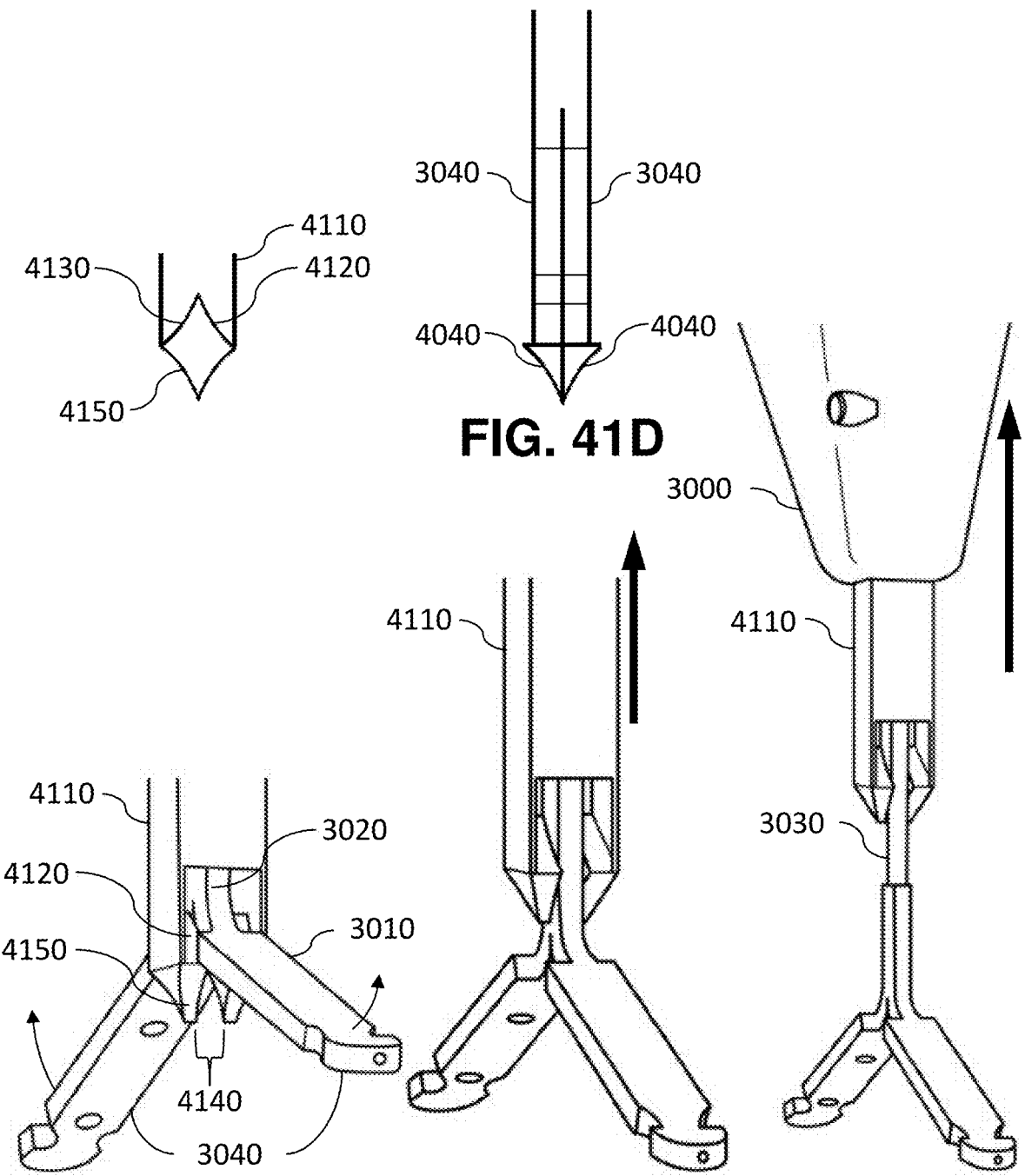

IMPLANTABLE ELECTRICAL LEADS AND ASSOCIATED DELIVERY SYSTEMS

CROSS-REFERENCE TO RELATED APPLICATIONS

This application is a continuation in part of and claims priority to U.S. patent application Ser. No. 16/888,462, filed May 29, 2020. This application also claims priority to U.S. Provisional Patent Application No. 63/049,561, filed Jul. 8, 2020. The disclosures of each are incorporated herein by reference in their entirety.

DESCRIPTION OF THE RELATED ART

Electrical leads can be implanted in patients for a variety of medical purposes. In one particular application, leads can be implanted to work in conjunction with a cardiac pacemaker or cardiac defibrillator. Pacemakers and cardiac defibrillators are medical devices that help control abnormal heart rhythms. A pacemaker uses electrical pulses to prompt the heart to beat at a normal rate. The pacemaker may speed up a slow heart rhythm, control a fast heart rhythm, and/or coordinate the chambers of the heart. Defibrillators can be provided in patients who are expected to, or have a history of, severe cardiac problems that may require electrical therapies up to and including the ceasing of ventricular fibrillation, otherwise known as cardiac arrest. Defibrillators may include leads that are physically inserted into the heart, including into the heart tissue (e.g., with screw-in lead tips) for the direct delivery of electrical current to the heart muscle.

The portions of pacemaker or ICD systems generally comprise three main components: a pulse generator, one or more wires called leads, and electrode(s) found on each lead. The pulse generator produces the electrical signals that help regulate the heartbeat. Most pulse generators also have the capability to receive and respond to signals that come from the heart. Leads are generally flexible wires that conduct electrical signals from the pulse generator toward the heart. One end of the lead is attached to the pulse generator and the other end of the lead, containing the electrode(s) is positioned on, in or near the heart.

When the exemplary embodiments discussed herein refer to cardiac pacing, it is contemplated that the embodiments and technologies disclosed may also be used in conjunction with defibrillation/ICD applications. Similarly, when exemplary embodiments discussed herein refer to defibrillation/ICD applications, it is contemplated that the embodiments and technologies disclosed may also be used in conjunction with cardiac pacing applications.

SUMMARY

Systems, methods, and devices to facilitate insertion of certain leads with electrode(s) into patients for a variety of medical purposes are described. In some implementations, an electrical lead for implantation in a patient can include a distal portion with electrodes that are configured to generate therapeutic energy for biological tissue of the patient. The electrical lead can have a proximal portion coupled to the distal portion and configured to engage a controller configured to cause the electrodes to generate the therapeutic energy. At least a portion of the distal portion of the lead can have two parallel planar surfaces that include the electrodes.

In some implementations, the electrodes can be thin metallic plates. In other implementations, the electrical lead can include an electrically insulating mask over a portion of the coil(s) on one of the parallel planar surfaces.

In some implementations, at least one electrode can be partially embedded in the portion of the distal portion of the lead, with the partially embedded electrode having an embedded portion and an exposed portion. In some implementations, the partially embedded electrode can be a circular helical coil or an elliptical helical coil.

Further disclosed is a method that can include placing a lead comprising both defibrillation and cardiac pacing electrodes at an extravascular location within a patient. The extravascular location can be in a region of a cardiac notch, or on or near the inner surface of an intercostal muscle. In some implementations, the placing can include inserting the lead through an intercostal space associated with the cardiac notch of a patient.

Also disclosed is a computer program product that can perform operations including receiving sensor data; determining, based at least on the sensor data, an initial set of electrodes on a defibrillation lead including more than two defibrillation electrodes, from which to deliver a defibrillation pulse; delivering the defibrillation pulse with the initial set of electrodes; receiving post-delivery sensor data; determining, based at least on the post-delivery sensor data whether the defibrillation pulse successfully defibrillated the patient; and, if necessary, determining an updated set of electrodes from which to deliver a subsequent defibrillation pulse.

Further disclosed is an electrical lead for implantation in a patient that can include a distal portion with electrodes that are configured to generate therapeutic energy for biological tissue of the patient. The electrical lead can have a proximal portion coupled to the distal portion and configured to engage a controller configured to cause the electrodes to generate the therapeutic energy. The distal portion can split apart into sub-portions that travel in multiple directions during implantation into the patient. The distal portion can split apart into two sub-portions of equal length. The electrodes can be wrapped around the sub-portions that travel in multiple directions during implantation and can include defibrillation electrodes and/or cardiac pacing electrodes.

In some implementations, the electrode(s) can be wrapped around a proximal part of the distal portion of the lead, which does not travel in a different direction during implantation. In some implementations, a pacing electrode extends between the sub-portions that travel in multiple directions during implantation.

In other implementations, electrodes can be partially embedded in the sub-portions that travel in multiple directions during implantation, and the partially embedded electrodes can have an embedded portion and an exposed portion. In some implementations, the exposed portions can be offset in order to avoid interference when the distal portion of the electrical lead is folded before it splits apart into sub-portions that travel in multiple directions during implantation. In some embodiments, the electrical lead can have concavities on the sub-portions such that exposed portions of the offset electrodes fit within the concavities when the electrical lead is folded.

In some implementations, the electrical lead can have suture holes in a proximal part of the distal portion of the lead, which does not travel in a different direction during implantation. In some implementations, the electrical lead can have grooves or notches on a proximal part of the distal portion of the lead, which does not travel in a different direction during implantation.

Also disclosed is a delivery system for a component that can be, for example, a splitting lead. The splitting lead can have a proximal portion configured to engage a controller and a distal portion configured to split apart into sub-portions that travel in multiple directions during implantation into a patient. The delivery system can include a handle configured to be actuated by an operator and a component advancer configured to advance the component into the patient. The component advancer can be configured to removably engage a portion of the component and may be coupled to the handle and configured to advance the component into the patient by applying a force to the portion of the component in response to actuation of the handle by the operator. The delivery system can also include an insertion tip having a first ramp configured to facilitate advancement of a first sub-portion into the patient in a first direction, and a second ramp configured to facilitate advancement of a second sub-portion into the patient in a second direction. In some implementations, the first direction can be opposite the second direction. In other implementations, the delivery system can include a third ramp configured to facilitate advancement of a third sub-portion into the patient in a third direction. The first ramp can include a gap configured to facilitate removal of the delivery system after implantation of the splitting lead.

In some implementations, the insertion tip can include a tissue-separating component. The tissue-separating component can be wedge-shaped or have a blunted distal end. In some implementations, the tissue-separating component can include a gap configured to facilitate removal of the delivery system after implantation of the splitting lead. The insertion tip may further include a movable cover configured to cover the gap. In some implementations, the delivery system can include the splitting lead, where a distal end of the splitting lead includes a gap-filling component configured to fill the gap of the tissue-separating component when the splitting lead is loaded into the delivery system.

Further disclosed is a method that can include inserting a lead delivery system into a patient; operating the lead delivery system to advance a lead so that a distal portion of the lead splits apart and travels in multiple directions within the patient.

In some implementations, the distal portion of the lead splits apart into two portions that travel in opposite directions parallel to a sternum of the patient. In other implementations, the distal portion of the lead splits apart into two portions that travel in directions approximately 100° apart and under a sternum of the patient. In some implementations, the distal portion splits apart into three portions that travel in directions approximately 90° apart and parallel or perpendicular to a sternum of the patient.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also contemplated that may include one or more processors and one or more memories coupled to the one or more processors. A memory, which can include a computer-readable storage medium, may include, encode, store, or the like, one or more programs that cause one or more processors to perform one or more of the operations described herein. Computer implemented methods consistent with one or more implementations of the current subject matter can be implemented by one or more data processors residing in a single computing system or across multiple computing systems. Such multiple computing systems can be connected and can exchange data and/or commands or other instructions or the like via one or more connections, including but not limited to a connection over a network (e.g., the internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to particular implementations, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 38 illustrates an exemplary splitting lead with multiple embedded electrodes, in accordance with certain aspects of the present disclosure;

FIG. 39 illustrates an exemplary splitting lead with multiple side-by-side embedded electrodes, in accordance with certain aspects of the present disclosure;

FIG. 41A illustrates an exemplary delivery system deploying a component, in accordance with certain aspects of the present disclosure;

FIG. 41B illustrates the delivery system of FIG. 41A at a later stage of deployment, in accordance with certain aspects of the present disclosure;

FIG. 41C illustrates the delivery system of FIG. 41A at a yet later stage of deployment, in accordance with certain aspects of the present disclosure;

FIG. 41D illustrates an exemplary gap-filling component of a splitting lead for use with a delivery system such as depicted in FIGS. 41A-C, in accordance with certain aspects of the present disclosure;

DETAILED DESCRIPTION

Implantable medical devices such as cardiac pacemakers or implantable cardioverter defibrillators (ICDs) may provide therapeutic electrical stimulation to the heart of a patient. The electrical stimulation may be delivered in the form of electrical pulses or shocks for pacing, cardioversion or defibrillation. This electrical stimulation is typically delivered via electrodes on one or more implantable leads that are positioned in, on or near the heart.

In one particular implementation discussed herein, a lead may be inserted in the region of the cardiac notch of a patient so that the distal end of the lead is positioned within the mediastinum, adjacent to the heart. For example, the distal end of the lead may be positioned in the anterior mediastinum, beneath the patient's sternum. The distal end of the lead can also be positioned so to be aligned with an intercostal space in the region of the cardiac notch. Other similar placements in the region of the cardiac notch, adjacent the heart, are also contemplated for this particular application of cardiac pacing.

Figure 1:
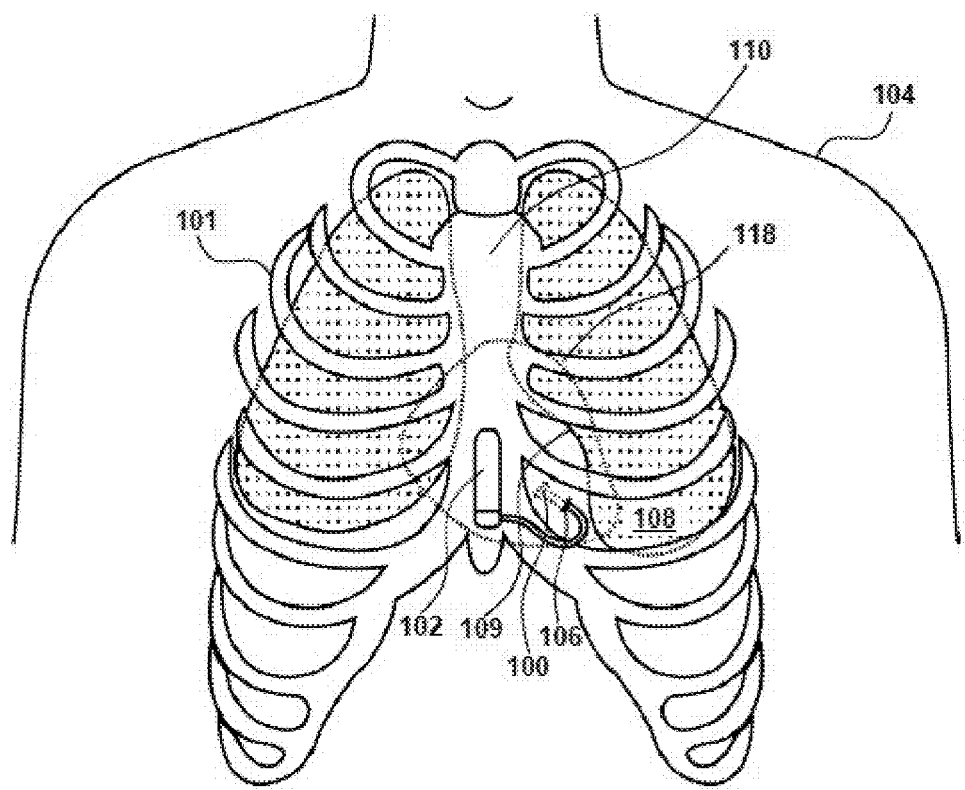
FIG. 1 is a diagram illustrating exemplary placements of elements of a cardiac pacing system, in accordance with certain aspects of the present disclosure.

In one exemplary procedure, as shown in FIG. 1, a cardiac pacing lead 100 may be inserted within the ribcage 101 of a patient 104 through an intercostal space 108 in the region of the cardiac notch. Lead 100 may be inserted through an incision 106, for example. The incision 106 may be made in proximity to the sternal margin to increase the effectiveness in finding the appropriate intercostal space 108 and avoiding certain anatomical features, for example the lung 109. The incision may be made lateral to the sternal margin, adjacent the sternal margin or any other direction that facilitates access to an appropriate intercostal space 108. A distal end of lead 100 can be positioned to terminate within the mediastinum of the thoracic cavity of the patient, proximate the heart 118. Lead 100 may then be connected to a pulse generator or controller 102, which may be placed above the patient's sternum 110. In alternative procedures, for temporary pacing, a separate controller may be used that is not implanted in the patient.

In some implementations, the pericardium is not invaded by the lead during or after implantation. In other implementations, incidental contact with the pericardium may occur, but heart 118 (contained within the pericardium) may remain untouched. In still further procedures, epicardial leads, or leads that reside within the pericardium, which do invade the pericardium, may be inserted.

Figure 2A:
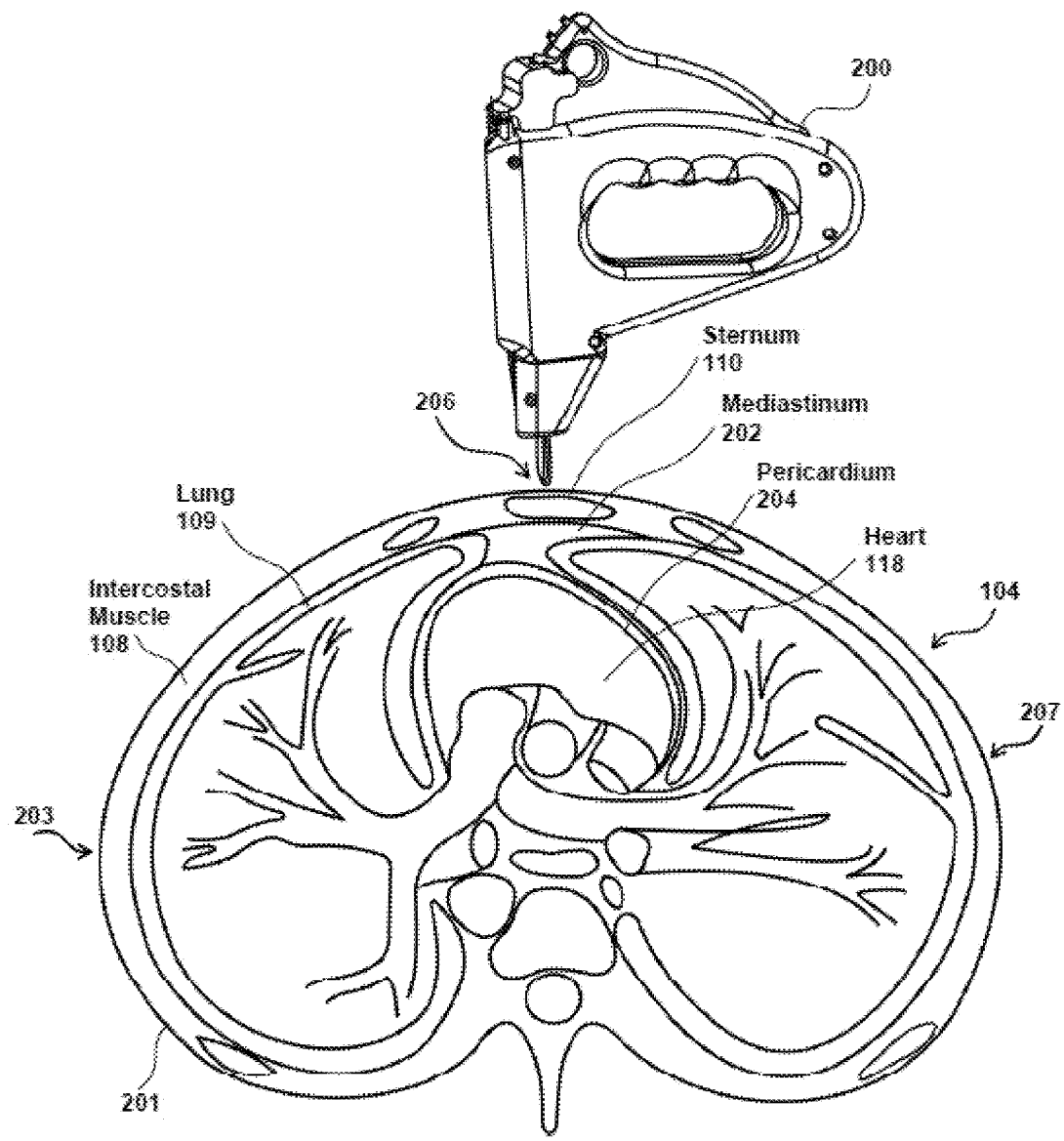
FIG. 2A is an illustration of an exemplary lead delivery system facilitating delivery of a cardiac pacing lead in the region of a cardiac notch, in accordance with certain aspects of the present disclosure.

FIG. 2A is an illustration of an exemplary lead delivery system 200 facilitating delivery of a lead in the region of a cardiac notch. FIG. 2A illustrates delivery system 200 and a cross section 201 (including left chest 203 and right chest 207) of a patient 104. FIG. 2A illustrates sternum 110, lung 109, intercostal muscle 108, heart 118, mediastinum 202, pericardium 204, and other anatomical features. As shown in FIG. 2A, lead delivery system 200 may be configured to allow for a distal end 206 of delivery system 200 to be pressed against the sternum 110 of patient 104.

Figure 2B:
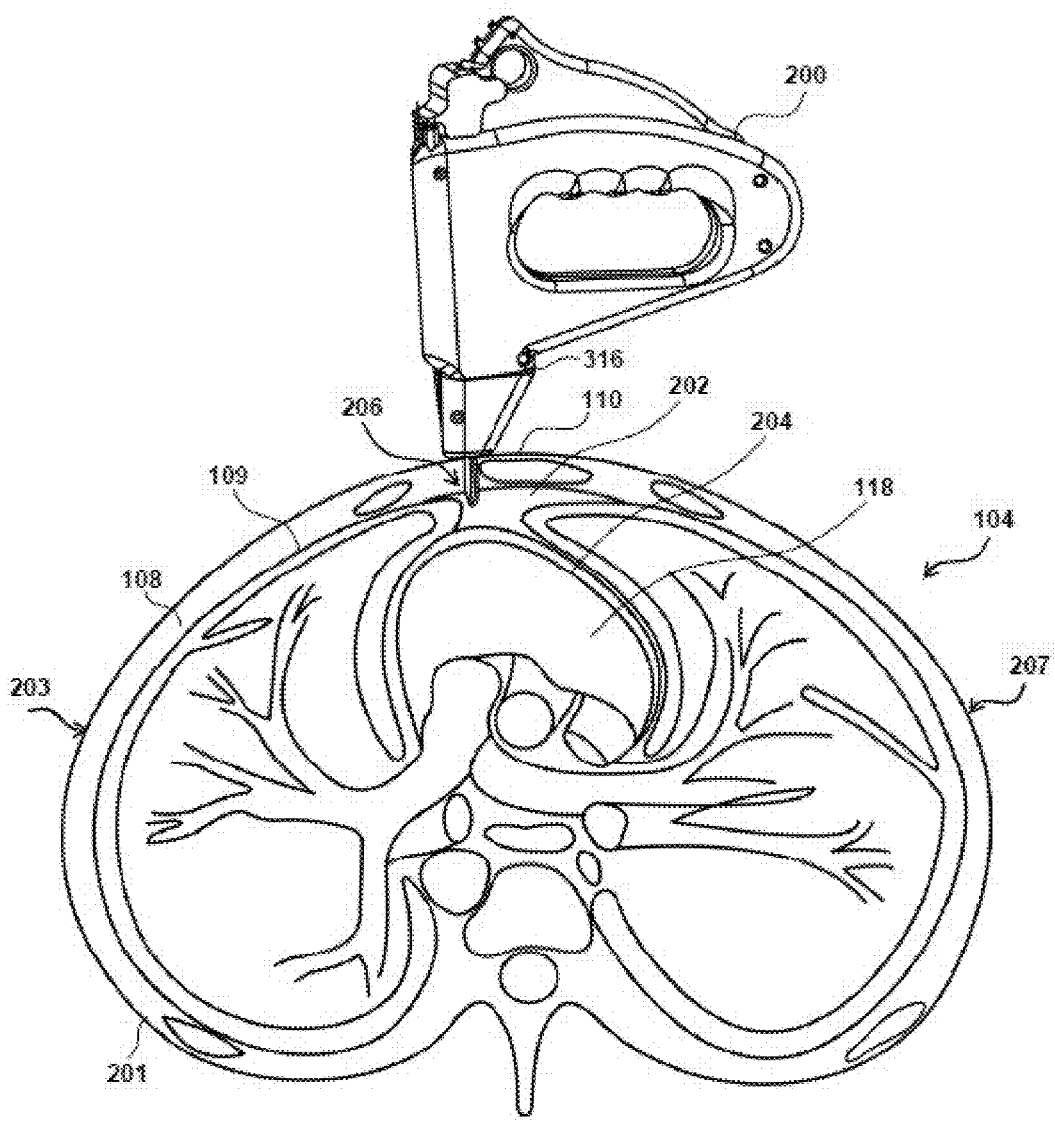
FIG. 2B illustrates a distal end of an exemplary lead delivery system having dropped into an intercostal space in the region of the cardiac notch, in accordance with certain aspects of the present disclosure.

In one implementation, a physician identifies an insertion point above or adjacent to a patient's sternum 110 and makes an incision. The distal end 206 of delivery system 200 can then be inserted through the incision, until making contact with sternum 110. The physician can then slide distal end 206 of delivery system 200 across sternum 110 toward the sternal margin until it drops through the intercostal muscle 108 in the region of the cardiac notch under pressure applied to the delivery system 200 by the physician. FIG. 2B illustrates the distal end 206 having dropped through the intercostal muscle in the region of the cardiac notch toward the pericardium.

In certain implementations, delivery system 200 may include an orientation or level guide 316 to aid the physician with obtaining the proper orientation and/or angle of delivery system 200 to the patient. Tilting delivery system 200 to the improper angle may negatively affect the deployment angle of lead 100 into the patient. For example, a horizontal level guide 316 on delivery system 200 helps to ensure that the physician keeps delivery system 200 level with the patient's sternum thereby ensuring lead 100 is delivered at the desired angle.

Figure 2C:
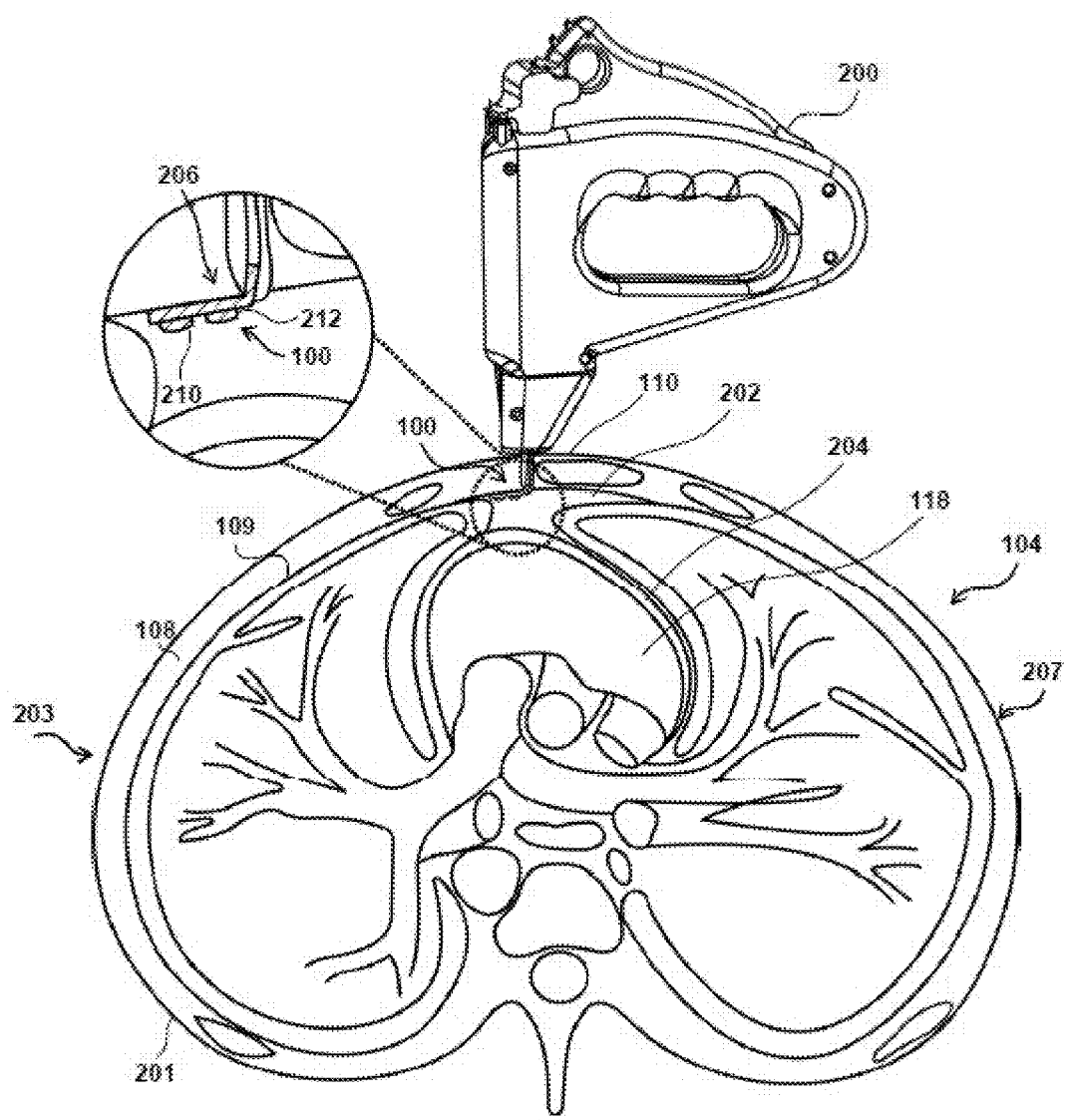
FIG. 2C illustrates an electrical lead exiting the exemplary delivery system with two electrodes positioned on a side of the lead facing the heart, in accordance with certain aspects of the present disclosure.

Following this placement of delivery system 200, the system may be actuated to insert an electrical lead 100 into the patient. FIG. 2C illustrates an exemplary electrical lead 100 exiting delivery system 200 with two electrodes 210, 212 positioned on one side of lead 100, within the mediastinum 202 and facing heart 118. FIG. 2C illustrates the lead 100 advancing in a direction away from sternum 110. This example is not intended to be limiting. For example, the lead 100 may also be advanced in a direction parallel to the sternum 110. In some implementations, delivery system 200 may be configured such that lead 100 advances in the opposite direction, under sternum 110, advances away from sternum 110 at an angle that corresponds to an angle of one or more ribs of patient 104, and/or advances in other orientations. Similarly, an exemplary device as shown in FIG. 2 may be flipped around so that the handle would be on the left side of FIG. 2, or held in other positions by the physician, prior to system actuation and insertion of lead 100.

Distal end 206 of delivery system 200 may be configured to move or puncture tissue during insertion, for example, with a relatively blunt tip (e.g., as described herein), to facilitate entry into the mediastinum without requiring a surgical incision to penetrate through intercostal muscles and other tissues. A blunt access tip, while providing the ability to push through tissue, can be configured to limit the potential for damage to the pericardium or other critical tissues or vessels that the tip may contact.

In an exemplary implementation, the original incision made by the physician above or adjacent to the sternum may also be used to insert a controller, pulse generator or additional electrode to which the implanted lead may be connected.

The delivery system and lead technologies described herein may be especially well suited for the cardiac pacing lead delivery example described above. While this particular application has been described in detail, and may be utilized throughout the descriptions below, it is contemplated that the delivery system(s) 200 and lead(s) 100 herein may be utilized in other procedures as well, such as the insertion of a defibrillation lead.

Figure 3:
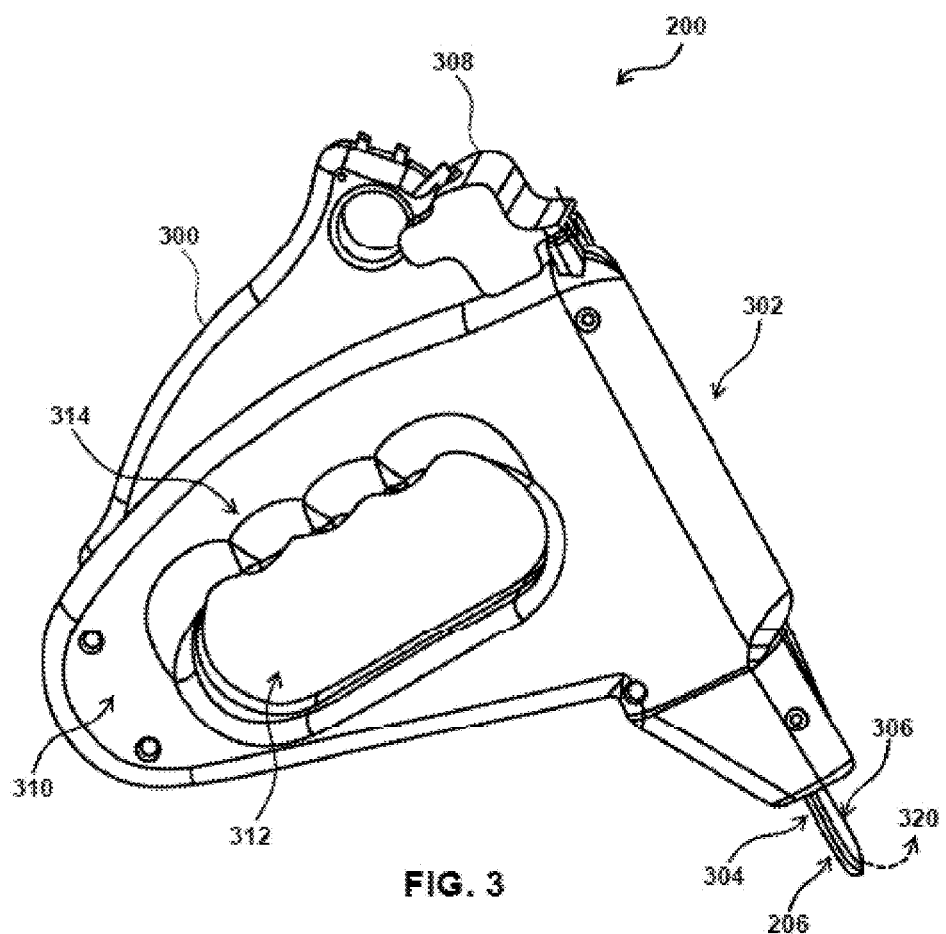
FIG. 3 illustrates an exemplary delivery system, in accordance with certain aspects of the disclosure.

FIG. 3 illustrates an exemplary delivery system 200. Delivery system 200 can include a handle 300, a component advancer 302, a first insertion tip 304, a second insertion tip 306, a lock 308, and/or other components. Handle 300 may be configured to be actuated by an operator. In some implementations, handle 300 may be coupled to a body 310 and/or other components of delivery system 200. Body 310 may include an orifice 312, finger depressions 314, a knurled surface, a lever arm, and/or other components configured to facilitate gripping of handle 300 by an operator. In some implementations, handle 300 and the body of the delivery system 200 may be coated with a material or their surfaces covered with a texture to prevent slippage of the physician's grasp when using delivery system 200.

Component advancer 302 may be coupled to handle 300 and configured to advance a component such as an electrical lead (as one example) into the patient by applying a force to the portion of the component in response to actuation of handle 300 by the operator.

First insertion tip 304 and second insertion tip 306 may be configured to close around a distal tip and/or segment of the component when the component is placed within component advancer 302. In some implementations, closing around a distal segment of the component may include blocking a path between the component and the environment outside delivery system 200. Closing around the distal segment of the component may also prevent the component from being unintentionally deployed and contacting biological tissue while delivery system 200 is being manipulated by the operator.

First insertion tip 304 and second insertion tip 306 may also be configured to fully enclose the distal segment of the component when the component is placed within component advancer 302. Fully enclosing the distal segment of the component may include covering, surrounding, enveloping, and/or otherwise preventing contact between the distal segment of the component and an environment around first insertion tip 304 and second insertion tip 306.

In still other implementations, first insertion tip 304 and second insertion tip 306 may be configured to only partially enclose the distal segment of the component when the component is placed within component advancer 302. For example, first insertion tip 304 and/or second insertion tip 306 may cover, surround, envelop, and/or otherwise prevent contact between one or more portions (e.g., surfaces, ends, edges, etc.) of the distal segment of the component and the environment around tips 304 and 306, but the tips 304 and 306 may also still block the path between the component and the environment outside the delivery system 200 during insertion.

In some implementations, first insertion tip 304 and second insertion tip 306 may be configured such that the component is held within component advancer 302 rather than within first insertion tip 304 and second insertion tip 306, prior to the component being advanced into the patient.

First insertion tip 304 and second insertion tip 306 may be further configured to push through biological tissue when in a closed position and to open (see, e.g., 320 in FIG. 3) to enable the component to exit from the component advancer 302 into the patient. In some implementations, opening may comprise second insertion tip 306 moving away from first insertion tip 304, and/or other opening operations. In some implementations, first and second insertion tips 304, 306 may be configured to open responsive to actuation of handle 300.

In some implementations, first insertion tip 304 and/or second insertion tip 306 may be configured to close (or re-close) after the component exits from the component advancer 302, to facilitate withdrawal of delivery system 200 from the patient. Thus, first insertion tip 304 and second insertion tip 306 may be configured to move, after the component exits from component advancer 302 into the patient, to a withdrawal position to facilitate withdrawal of first insertion tip 304 and second insertion tip 306 from the biological tissue. In some implementations, the withdrawal position may be similar to and/or the same as an original closed position. In some implementations, the withdrawal position may be a different position. In some implementations, the withdrawal position may be wider than the closed position, but narrower than an open position. For example, first insertion tip 304 and/or second insertion tip 306 may move to the open position to release the component, but then move to a different position with a narrower profile (e.g., the withdrawal position) so that when the tips 304, 306 are removed they are not met with resistance pulling through a narrow rib space, and/or other biological tissue.

In some implementations, first and second insertion tips 304, 306 may have blunt edges. Blunt edges may include rounded and/or otherwise dull edges, corners, surfaces, and/or other components of first and second insertion tips 304, 306. The blunt edges may be configured to prevent insertion tips 304 and 306 from rupturing any veins or arteries, the pericardial sac, the pleura of the lungs, and/or causing any other unintentional damage to biological tissue. The blunt edges may prevent, for example, rupturing veins and/or arteries by pushing these vascular items to the side during insertion. The blunt edges may also prevent, for example, the rupturing of the pericardium or pleura because they are not sharp.

Figure 4:
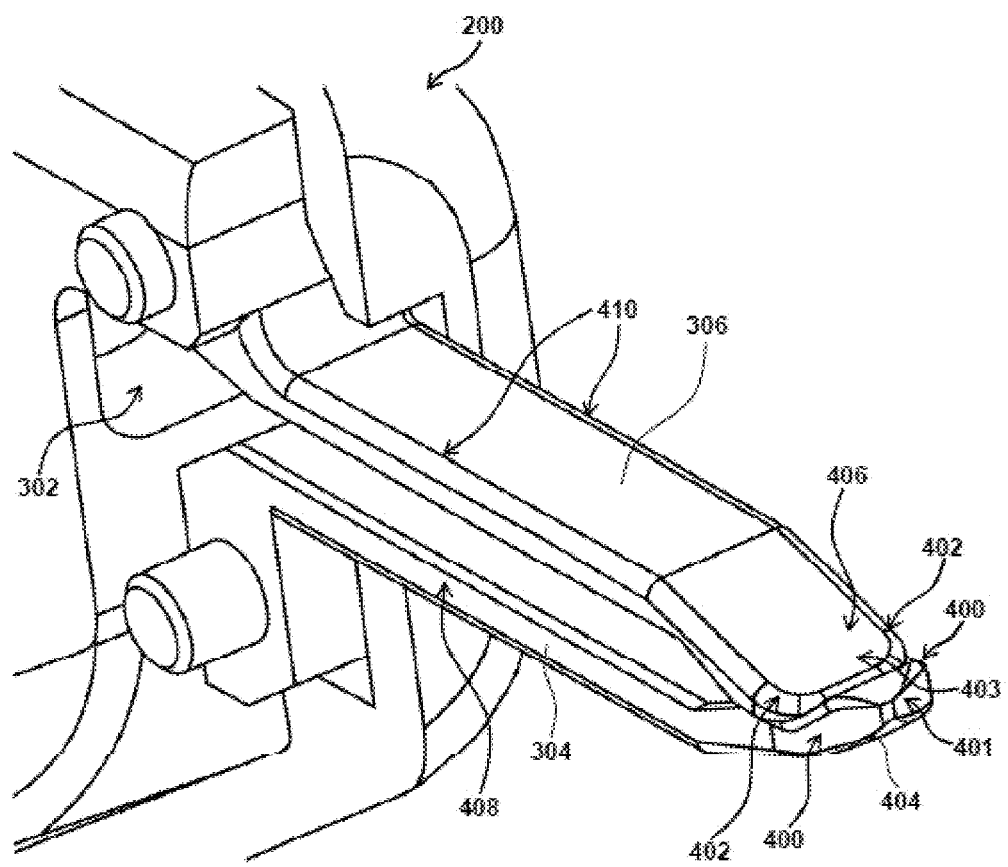
FIG. 4 illustrates an example of first and second insertion tips of the delivery system with blunt edges, in accordance with certain aspects of the disclosure.

FIG. 4 illustrates first and second insertion tips 304, 306 with exemplary implementations of such blunt edges. As shown in FIG. 4, first and second insertion tips 304, 306 may have rounded corners 400, 402 and/or end surfaces 401, 403 at their respective ends 404, 406. First and second insertion tips 304, 306 may have rounded edges 408, 410 that run along a longitudinal axis of tips 304, 306. However, this description is not intended to be limiting. In some implementations, first and second insertion tips 304, 306 may also have sharp edges, ends, and/or other features.

Figure 5:
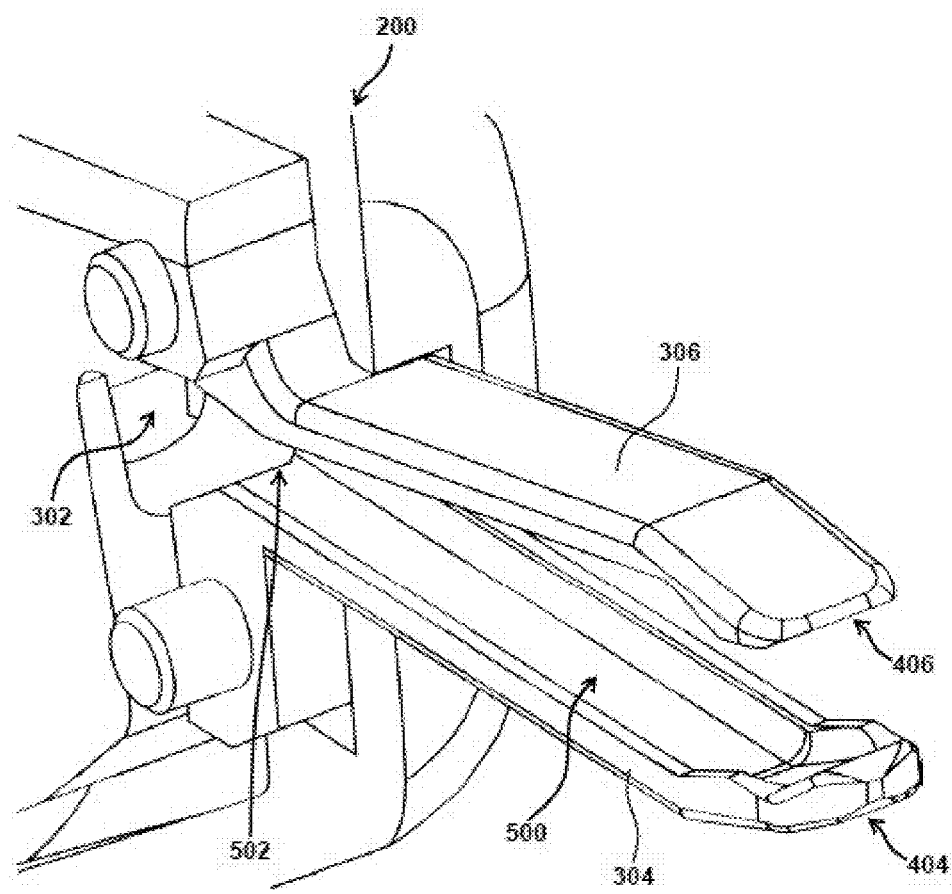
FIG. 5 illustrates an exemplary channel at least partially complimentary to a shape of the component and configured to guide the component into the patient, in accordance with certain aspects of the disclosure.

In some implementations, first and second insertion tips 304, 306 may each include a channel at least partially complimentary to a shape of the component and configured to guide the component into the patient. FIG. 5 illustrates an example of such a channel. As shown in FIG. 5, first insertion tip 304 may include a channel 500 at least partially complimentary to a shape of the component and configured to guide the component into the patient. Second insertion tip 306 may also include a channel similar to and/or the same as channel 500 (although the channel in insertion tip 306 is not visible in FIG. 5). Channel 500 may extend along a longitudinal axis of insertion tip 304 from an end 502 of insertion tip 304 configured to couple with component advancer 302 toward end 404.

In some implementations, channel 500 may be formed by a hollow area of insertion tip 304 that forms a trench, for example. The hollow area and/or trench may have one or more shapes and/or dimensions that are at least partially complimentary to a shape and/or dimension(s) of the component, and are configured to guide the component into the patient. In some implementations, the hollow area and/or trench may be configured such that the component may only slide within channel 500 inside the insertion tips 304, 306, and therefore prevent the component from advancing out one of the sides of the insertion tips 304, 306 when pushed by component advancer 302.

In some implementations, channel 500 may include a second channel and/or groove configured to engage alignment features included on a component. The second channel or groove may be located within channel 500, but be deeper and/or narrower than channel 500. The component may then include a rib and/or other alignment features configured to engage such a groove. The rib may be on an opposite side of the component relative to electrodes, for example. These features may enhance the guidance of a component through channel 500, facilitate alignment of a component in channel 500 (e.g., such that the electrodes are oriented in a specific direction in tips 304, 306, preventing the component from exiting tips 304, 306 to one side or the other (as opposed to exiting out ends 404, 406), and/or have other functionalities.

In some implementations, the second channel and/or groove may be sized to be just large enough to fit an alignment feature of the component within the second channel and/or groove. This may prevent an operator from pulling a component too far up into delivery system 200 (FIG. 3) when loading delivery system 200 with a component (e.g., as described below).

The channels and/or grooves may also provide a clinical benefit. For example, the channel and/or groove may allow for narrower insertion tips 304 and 306 that need not be configured to surround or envelop all sides of the component (e.g., they may not need sidewalls to keep the component in position during implantation). If surrounding or enveloping all sides of a component is necessary, the insertion tips would need to be larger, and would meet with greater resistance when separating tissue planes within intercostal spaces, for example. However, in other implementations (e.g., as described herein), insertion tips 304, 306 may completely surround and/or envelop the component.

Figure 6:
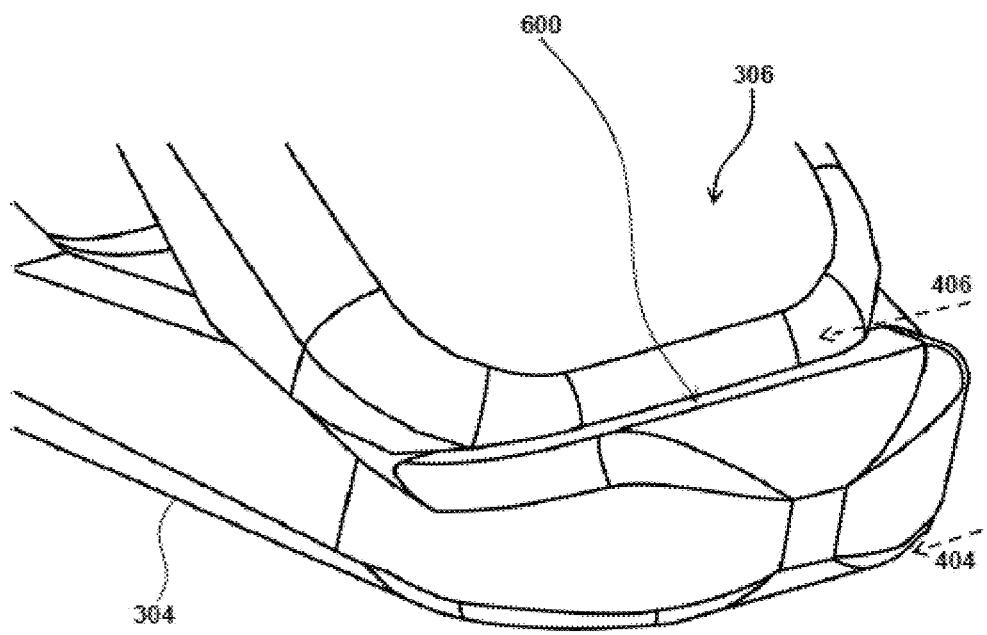
FIG. 6 illustrates a first insertion tip being longer than a second insertion tip, in accordance with certain aspects of the disclosure.

In some implementations, as shown in FIG. 6, a first insertion tip 304 may be longer than a second insertion tip 306 and the end 404 of first insertion tip 304 will extend beyond the end 406 of insertion tip 306. Such a configuration may assist with spreading of tissue planes and help to avoid pinching tissue, veins, arteries or the like while delivery system 200 is being manipulated through biological tissue.

In some implementations, both the first and second insertion tips 304, 306 may be moveable. In other implementations, the first insertion tip 304 may be fixed, and second insertion tip 306 may be moveable.

In one particular implementation, a fixed insertion tip 304 may be longer than a movable insertion tip 306. This configuration may allow more pressure to be exerted on the outermost edge (e.g., end 404 of tip 304) of delivery system 200 without (or with reduced) concern that tips 304 and 306 will open when pushing through biological tissue. Additionally, the distal ends 404 and 406 may form an underbite 600 that allows distal end 406 of movable insertion tip 306 (in this example) to seat behind fixed insertion tip 304, and thus prevent tip 406 from experiencing forces that may inadvertently open movable insertion tip 306 during advancement. However, this description is not intended to be limiting. In some implementations, a movable insertion tip 306 may be longer than a fixed insertion tip 304.

Figure 7:
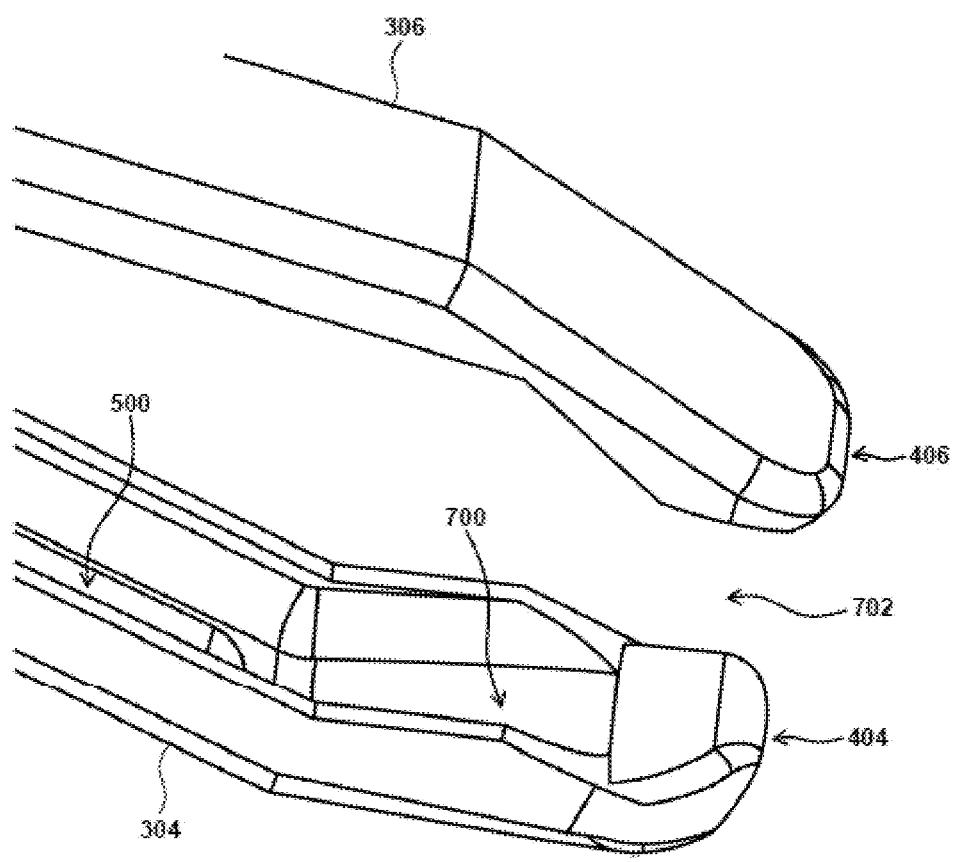
FIG. 7 illustrates an example of a ramped portion of an insertion tip, in accordance with certain aspects of the disclosure.

In some implementations, a fixed (e.g., and/or longer) insertion tip 304 may include a ramped portion configured to facilitate advancement of the component into the patient in a particular direction. FIG. 7 illustrates an example of a ramped portion 700 of insertion tip 304. Ramped portion 700 may be located on an interior surface 702 of insertion tip 304, between channel 500 and distal end 404 of insertion tip 304. Ramped portion 700 may be configured to facilitate advancement of the component into the patient in a particular direction. The particular direction may be a lateral direction relative to a position of insertion tip 304, for example. The lateral deployment of a component (e.g., an electrical lead) when it exits insertion tip 304 and moves into the anterior mediastinum of the patient may facilitate deployment without contacting the heart (e.g., as described relative to FIGS. 2A-2C above). Ramped portion 700 may also encourage the component to follow a preformed bias (described below) and help prevent the lead from deploying in an unintentional direction.

Figure 8:
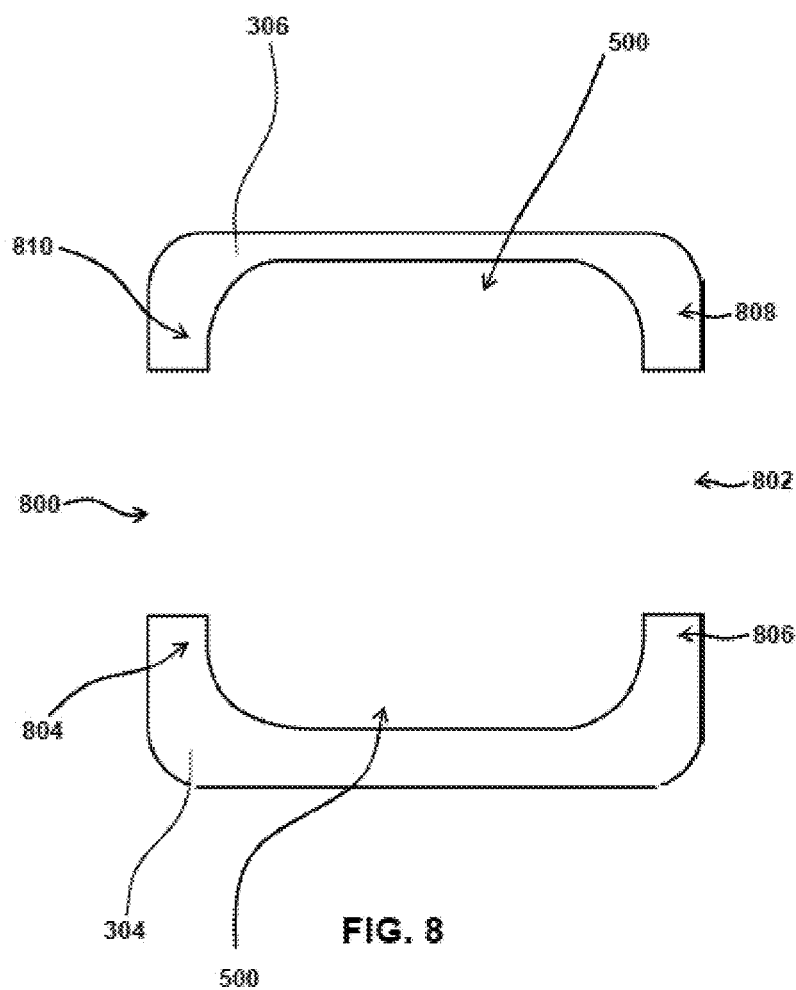
FIG. 8 illustrates an example of insertion tips with open side walls, in accordance with certain aspects of the disclosure.

In some implementations, insertion tips 304, 306 may have open side walls. FIG. 8 illustrates an example of insertion tips 304, 306 with open side walls 800, 802. FIG. 8 illustrates a cross sectional view of insertion tips 304, 306, looking at insertion tips 304, 306 from distal ends 404, 406 (as shown in FIG. 7). Open side walls 800, 802 may be formed by spaces between insertion tip 304 and insertion tip 306. In the example of FIG. 8, insertion tips 304 and 306 are substantially "U" shaped, with the ends 804, 806, 808, 810 extending toward each other, but not touching, such that open side walls 800 and 802 may be formed. Open side walls 800, 802 may facilitate the use of a larger component (e.g., a component that does not fit within channel(s) 500), without having to increase a size (e.g., a width, etc.) of insertion tips 304, 306. This may avoid effects larger insertion tips may have on biological tissue. For example, larger insertion tips are more invasive than smaller insertion tips. As such, larger insertion tips may meet with greater resistance when separating tissue planes within intercostal spaces during deployment and may cause increased trauma than insertion tips having a reduced cross sectional size.

Figure 9A:
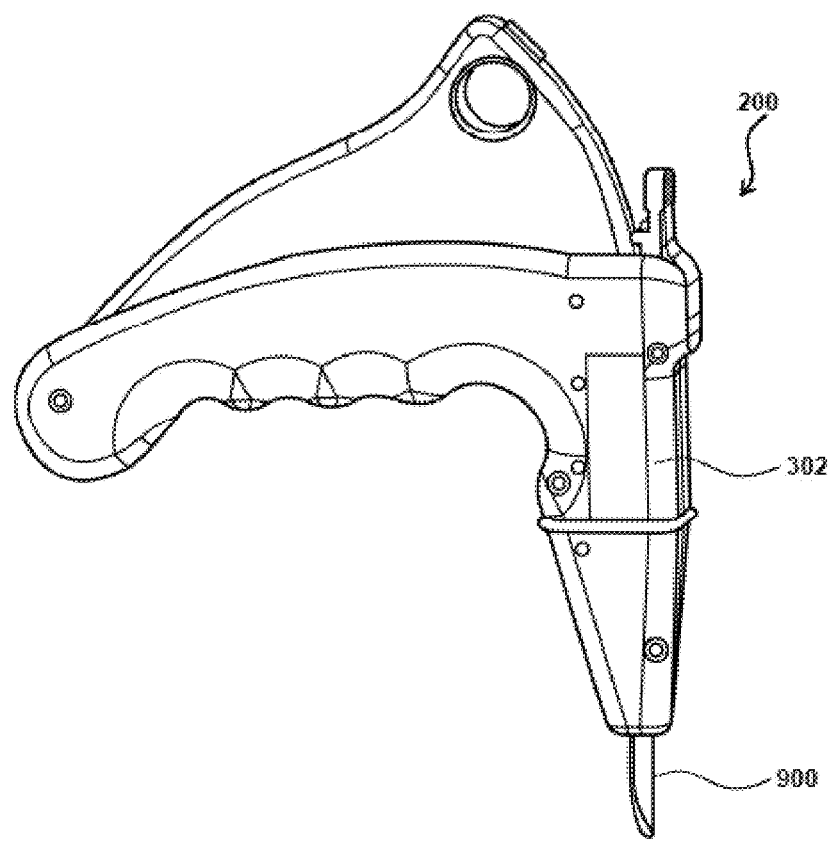
FIG. 9A illustrates one possible example of a delivery system having a unitary insertion tip, in accordance with certain aspects of the disclosure.

In some implementations, delivery system 200 (FIG. 3) may include a handle 300 (FIG. 3), a component advancer 302 (FIG. 3), and a unitary insertion tip (e.g., instead of first and second insertion tips 304 and 306). FIG. 9A illustrates one possible example of a delivery system 200 having a unitary insertion tip 900. Insertion tip 900 may be coupled to a component advancer 302 similar to and/or in the same manner that insertion tips 304 and 306 (FIG. 7) may be coupled to component advancer 302.

Figure 9B:
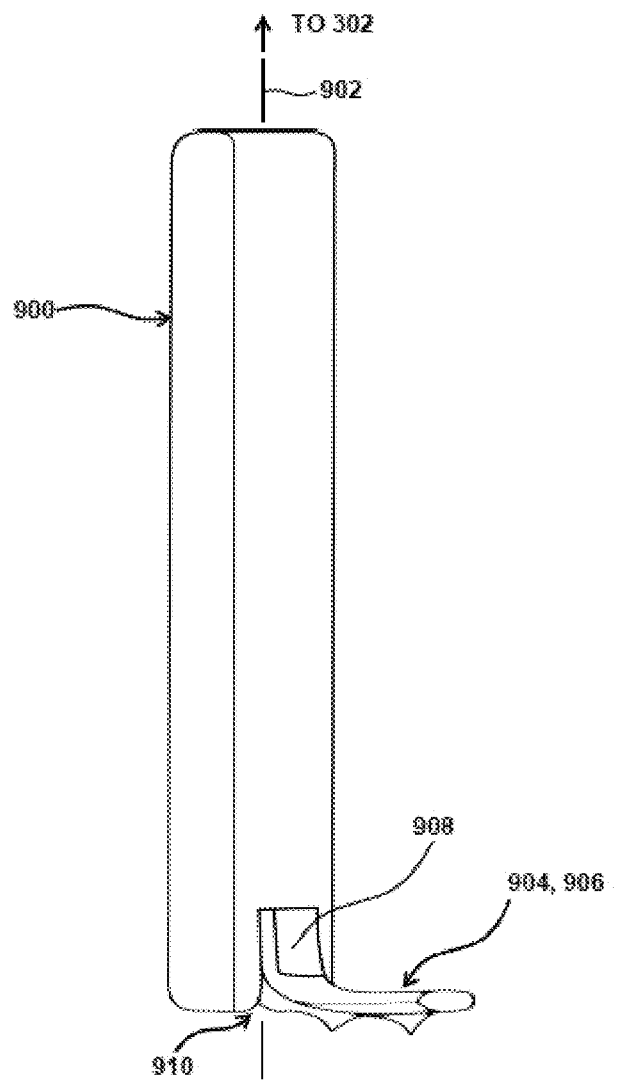
FIG. 9B illustrates one possible example of a unitary insertion tip, in accordance with certain aspects of the disclosure.

Unitary insertion tip 900 may have a circular, rectangular, wedge, square, and/or other cross sectional shape(s). In some implementations, insertion tip 900 may form a (circular or rectangular, etc.) tube extending along a longitudinal axis 902 (FIG. 9B) of insertion tip 900. Referring to FIG. 9B, in some implementations, insertion tip 900 may be configured to hold the component (labeled as 904) when the component is placed within component advancer 302. In some implementations, insertion tip 900 may be configured to hold a distal end (labeled as 906) and/or tip of component 904 when component 904 is placed within component advancer 302.

Insertion tip 900 may be configured to push through biological tissue and may include a distal orifice 908 configured to enable component 904 to exit from component advancer 302 into the patient.

Figure 9C:
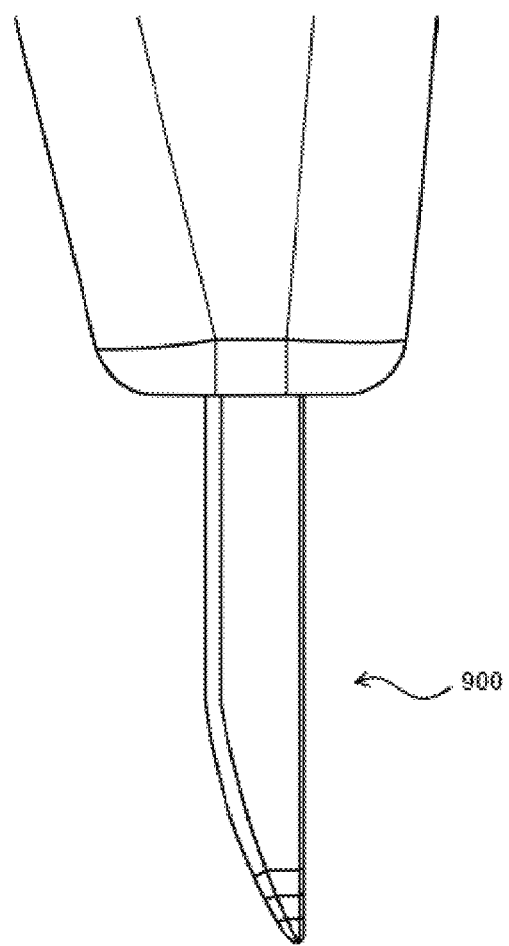
FIG. 9C illustrates an alternative insertion tip design having a wedge shape, in accordance with certain aspects of the disclosure.

FIG. 9C illustrates an alternative insertion tip 900 design having a wedge shape. A wedge-shaped insertion tip 900 reduces and/or eliminates the exposure of distal orifice 908 to the surrounding tissue during insertion. This design prevents tissue coring since only the leading edge of insertion tip 900 is exposed and thereby separates tissues rather than coring or cutting tissue during insertion. Accordingly, the present disclosure contemplates an insertion tip that may be configured to reduce the exposure of the distal orifice during insertion.

Figure 9D:
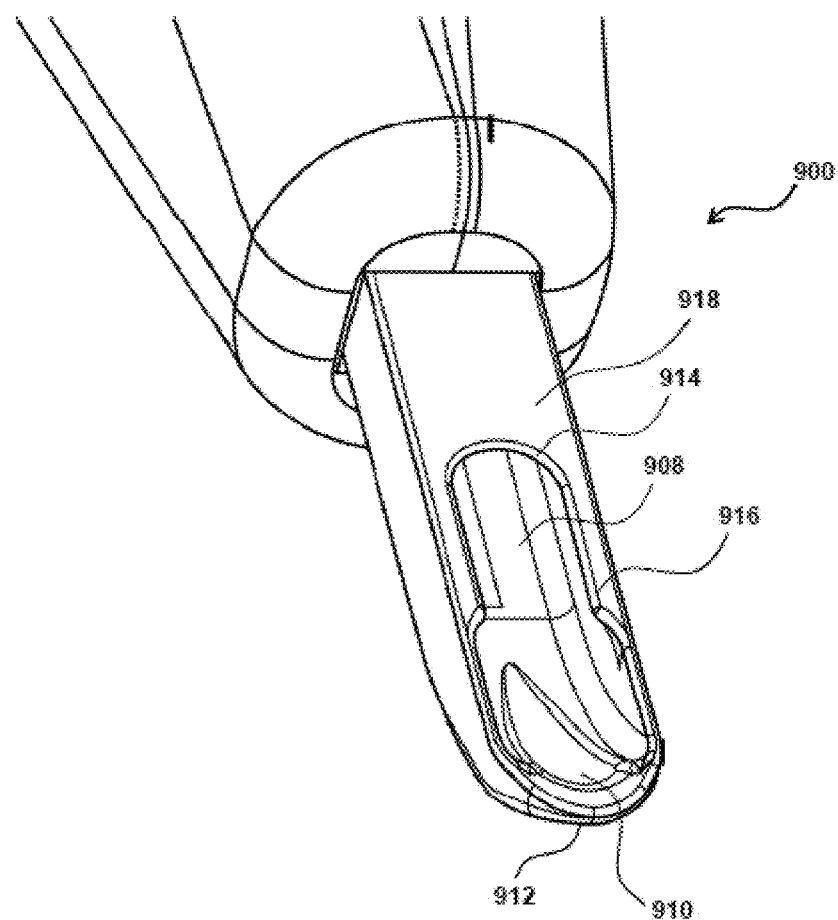
FIG. 9D illustrates certain features applicable to a unitary insertion tip design, in accordance with certain aspects of the disclosure.

Referring to FIG. 9D, distal tip 912 may be rounded into an arc so the deployment force exerted by the physician during insertion concentrates in a smaller area (the distalmost portion of distal tip 912). Additionally, the distalmost portion of distal tip 912 may be blunted to minimize trauma and damage to surrounding tissue during insertion. Notch 914 provides additional room for the proximal end of lead 100 having a rigid electrical connector to more easily be inserted when loading lead 100 in delivery system 200. Rails 916 overlap lead 100 and hold lead 100 flat when the lead is retracted and held within delivery system 200. In some implementations, the inner edge of rails 916 gradually widen as rails 916 advance toward distal tip 912.

FIG. 9D illustrates certain features applicable to a unitary insertion tip design.

In some implementations, insertion tip 900 may include a movable cover 918 configured to prevent the biological tissue from entering distal orifice 908 when insertion tip 900 pushes through the biological tissue. The moveable cover may move to facilitate advancement of component 904 into the patient.

It is contemplated that many of the other technologies disclosed herein can also be used with the unitary tip design. For example, insertion tip 900 may include a ramped portion 910 configured to facilitate advancement of the component into the patient in a particular direction and to allow the protruding electrodes 210, 212 to pass easier through the channel created within insertion tip 900.

In some implementations, delivery system 200 (FIG. 3) may include a dilator. In some implementations, insertion tips 304, 306, and/or insertion tip 900 may operate in conjunction with such a dilator. Use of a dilator may allow an initial incision to be smaller than it may otherwise be. The dilator may be directionally oriented to facilitate insertion of a component (e.g., an electrical lead) through the positioned dilator manually, and/or by other means. The dilator may comprise a mechanism that separates first and second insertion tips 304, 306. For example, relatively thin first and second insertion tips 304, 306 may be advanced through biological tissue. An actuator (e.g., a handle, and/or a device couple to the handle operated by the user) may insert a hollow, dilating wedge that separates first and second insertion tips 304, 306. The actuator (operated by the user) may advance a lead through the hollow dilator into the biological tissue. The dilator may also be used to separate the first and second insertion tips 304, 306 such that they lock into an open position. The dilator can then be removed and the lead advanced into the biological tissue.

Figure 10:
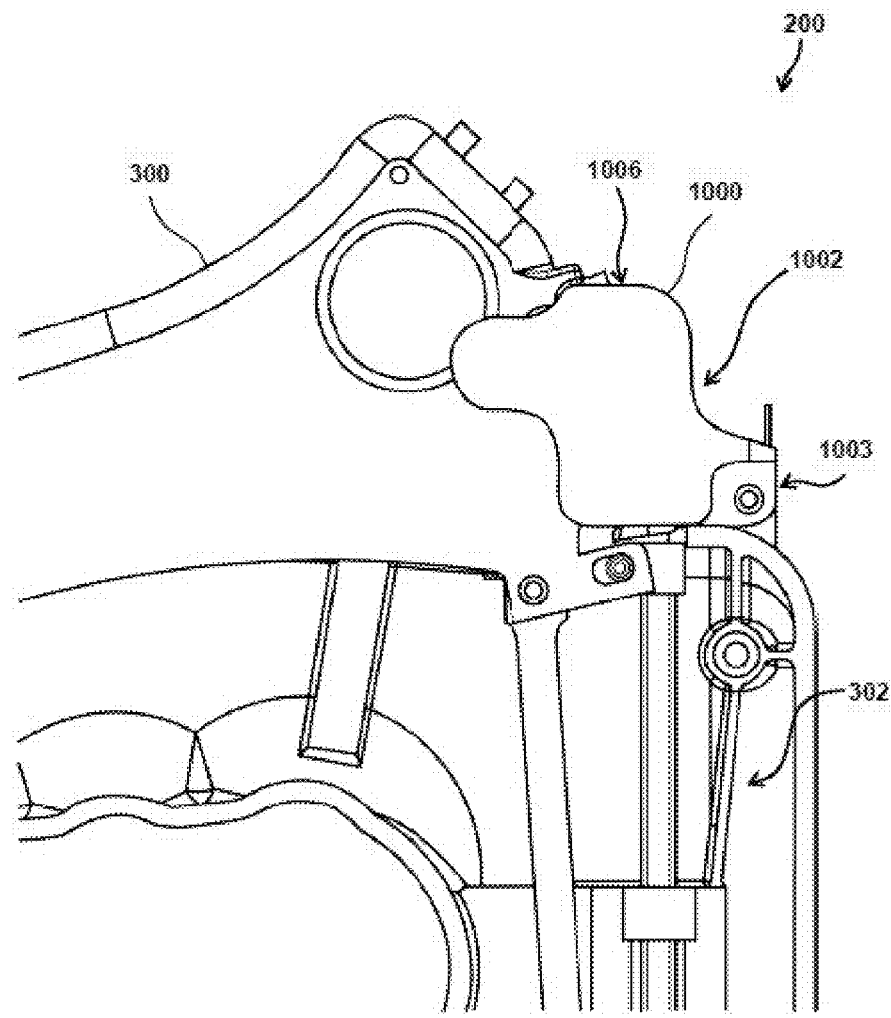
FIG. 10 illustrates an exemplary lock for a delivery system, in a locked position, in accordance with certain aspects of the disclosure.
Figure 11:
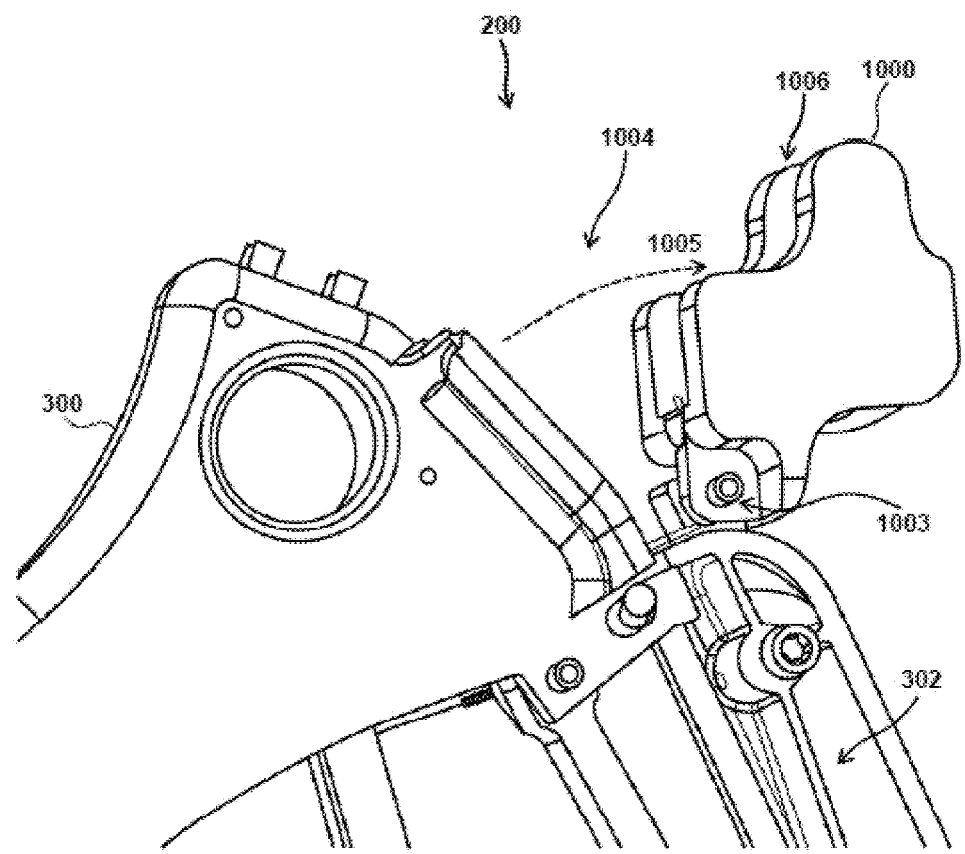
FIG. 11 illustrates the lock in an unlocked position, in accordance with certain aspects of the disclosure.

FIGS. 10 and 11 illustrate an exemplary lock 1000 that may be included in delivery system 200. A lock 1000 may be similar to and/or the same as lock 308 shown in FIG. 3. In some implementations, lock 1000 may be configured to be moved between an unlocked position that allows actuation of handle 300 (and in turn component advancer 302) by the operator and a locked position that prevents actuation, and prevents first insertion tip 304 (FIG. 7) and second insertion 306 tip (FIG. 7) from opening.

FIG. 10 illustrates lock 1000 in a locked position 1002. FIG. 11 illustrates lock 1000 in an unlocked position 1004. Lock 1000 may be coupled to handle 300 and/or component advancer 302 via a hinge 1003 and/or other coupling mechanisms. In some implementations, lock 1000 may be moved from locked position 1002 to unlocked position 1004, and vice versa, by rotating and/or otherwise moving an end 1006 of lock 1000 away from handle 300 (see, e.g., 1005 in FIG. 11). Lock 1000 may be moved from locked position 1002 to unlocked position 1004, and vice versa, by the operator with thumb pressure, trigger activation (button/lever, etc.) for example, and/or other movements. Additionally, the mechanism may also include a safety switch such that a trigger mechanism must be deployed prior to unlocking the lock with the operator's thumb.

When lock 1000 is engaged or in locked position 1002, lock 1000 may prevent an operator from inadvertently squeezing handle 300 to deploy the component. Lock 1000 may prevent the (1) spreading of the distal tips 304, 306, and/or (2) deployment of a component while delivery system 200 is being inserted through the intercostal muscles.

Lock 1000 may be configured such that deployment of the component may occur only when lock 1000 is disengaged (e.g., in the unlocked position 1004 shown in FIG. 11). Deployment may be prevented, for example, while an operator is using insertion tips 304, 306 of delivery system 200 to slide between planes of tissue in the intercostal space as pressure is applied to delivery system 200. Lock 1000 may be configured such that, only once system 200 is fully inserted into the patient can lock 1000 be moved so that handle 300 may be actuated to deliver the component through the spread (e.g., open) insertion tips 304, 306. It should be noted that the specific design of lock 1000 shown in FIGS. 10 and 11 is not intended to be limiting. Other locking mechanism designs are contemplated. For example, the lock 1000 may be designed so that lock 1000 must be fully unlocked to allow the handle 300 to be deployed. A partial unlocking of lock 1000 maintains the handle in the locked position as a safety mechanism. Furthermore, the lock 1000 may be configured such that any movement from its fully unlocked position will relock the handle 300.

Returning to FIG. 3, component advancer 302 may be configured to advance a component into a patient. The component may be an electrical lead (e.g., as described herein), and/or other components.

The component advancer 302 may be configured to removably engage a portion of the component, and/or to deliver the component into the patient through insertion tips 304 and 306. In some implementations, component advancer 302 and/or other components of system 200 may include leveraging components configured to provide a mechanical advantage or a mechanical disadvantage to an operator such that actuation of handle 300 by the operator makes advancing the component into the patient easier or more difficult. For example, the leveraging components may be configured such that a small and/or relatively light actuation pressure on handle 300 causes a large movement of a component (e.g., full deployment) from component advancer 302. Or, in contrast, the leveraging components may be configured such that a strong and/or relatively intense actuation pressure is required to deliver the component. In some implementations, the leveraging components may include levers, hinges, wedges, gears, and/or other leveraging components (e.g., as described herein). In some implementations, handle 300 may be advanced in order to build up torque onto component advancer 302, without moving the component. Once sufficient torque has built up within the component advancer, the mechanism triggers the release of the stored torque onto the component advancer, deploying the component.

In some implementations, component advancer 302 may include a rack and pinion system coupled to handle 300 and configured to grip the component such that actuation of handle 300 by the operator causes movement of the component via the rack and pinion system to advance the component into the patient. In some implementations, the rack and pinion system may be configured such that movement of handle 300 moves a single or dual rack including gears configured to engage and rotate a single pinion or multiple pinions that engage the component, so that when the single pinion or multiple pinions rotate, force is exerted on the component to advance the component into the patient.

Figure 12A:
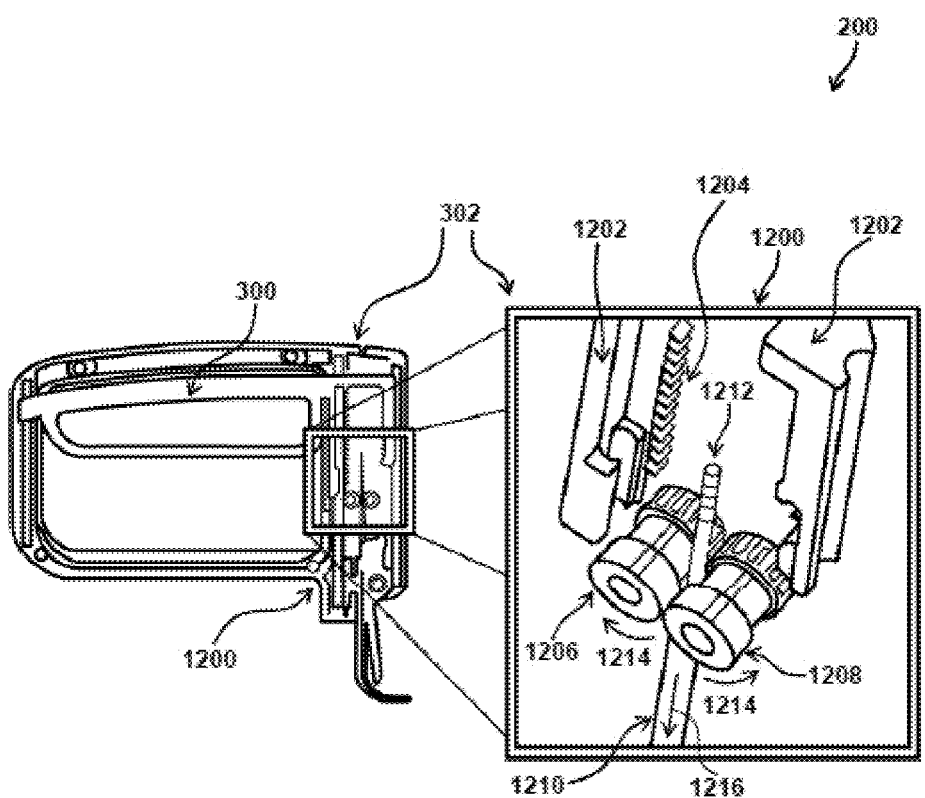
FIG. 12A illustrates an example rack and pinion system that may be included in a component advancer of the delivery system, in accordance with certain aspects of the disclosure.

FIG. 12A illustrates an exemplary rack and pinion system 1200. Rack and pinion system may include rack(s) 1202 with gears 1204. Example system 1200 includes two pinions 1206, 1208. Pinions 1206 and 1208 may be configured to couple with a component 1210 (e.g., an electrical lead), at or near a distal end 1212 of component 1210, as shown in FIG.

12A. Rack and pinion system 1200 may be configured such that movement of handle 300 moves rack 1202 comprising gears 1204 configured to engage and rotate pinions 1206, 1208 that engage component 1210, so that when pinions 1206, 1208 rotate 1214, force is exerted 1216 on component 1210 to advance component 1210 into the patient.

Figure 12B:
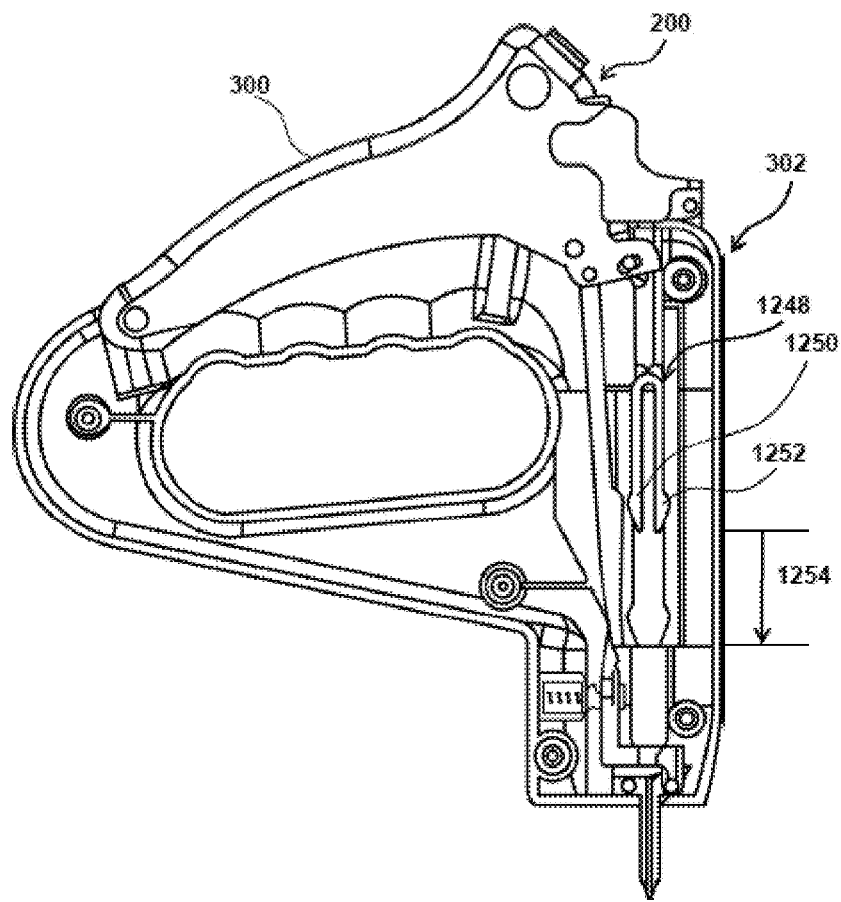
FIG. 12B illustrates an example clamp system that may be included in a component advancer of the delivery system, in accordance with certain aspects of the disclosure.

In some implementations, responsive to handle 300 being actuated, a component (e.g., component 1210) may be gripped around a length of a body of the component, as shown in FIG. 12B. The body of the component may be gripped by two opposing portions 1250, 1252 of component advancer 302 that engage either side of the component, by two opposing portions that engage around an entire circumferential length of a portion of the body, and/or by other gripping mechanisms.

Once gripped, further actuation of handle 300 may force the two opposing portions within component advancer 302 to traverse toward a patient through delivery system 200. Because the component may be secured by these two opposing portions, the component may be pushed out of delivery system 200 and into the (e.g., anterior mediastinum) of the patient. By way of a non-limiting example, component advancer 302 may comprise a clamp 1248 having a first side 1250 and a second side 1252 configured to engage a portion of the component. Clamp 1248 may be coupled to handle 300 such that actuation of handle 300 by the operator may cause movement of the first side 1250 and second side 1252 of clamp 1248 to push on the portion of the component to advance the component into the patient. Upon advancing the component a fixed distance (e.g., distance 1254) into the patient, clamp 1248 may release the component. Other gripping mechanisms are also contemplated.

Returning to FIG. 3, in some implementations, component advancer 302 may include a pusher tube coupled with handle 300 such that actuation of handle 300 by the operator causes movement of the pusher tube to push on the portion of the component to advance the component into the patient. In some implementations, the pusher tube may be a hypo tube, and/or other tubes. In some implementations, the hypo tube may be stainless steel and/or be formed from other materials. However, these examples are not intended to be limiting. The pusher tube may be any tube that allows system 200 to function as described herein.

Figure 13:
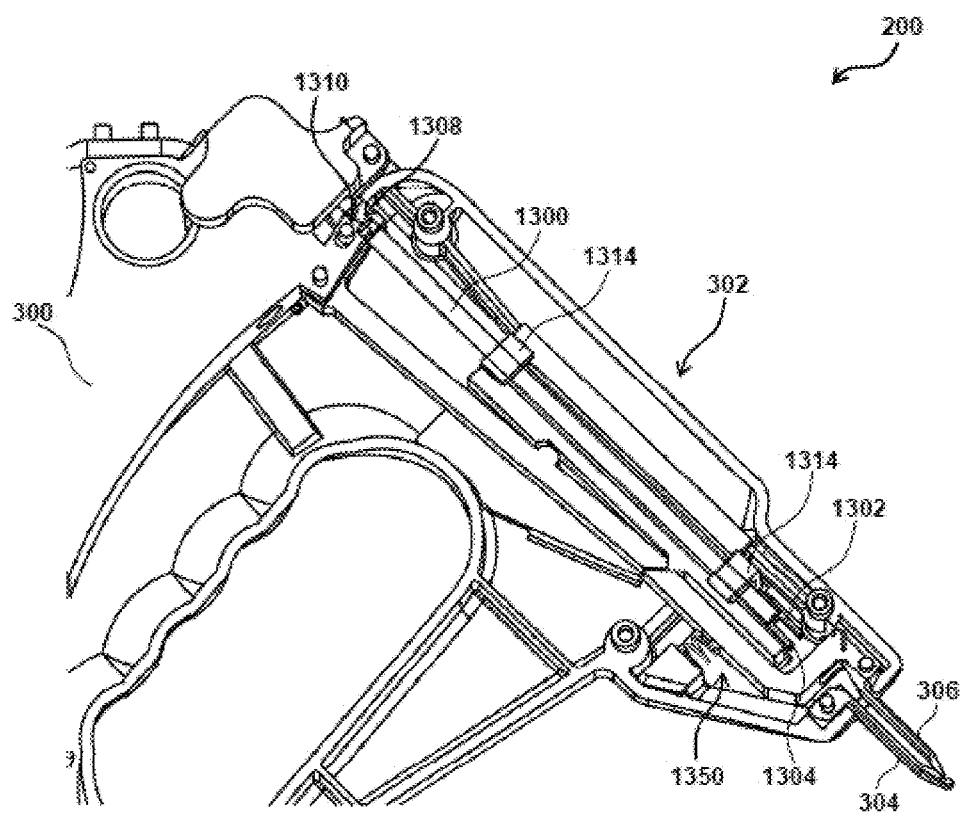
FIG. 13 illustrates a view of an exemplary implementation of a component advancer including a pusher tube coupled with the handle of a delivery system, in accordance with certain aspects of the disclosure.
Figure 14:
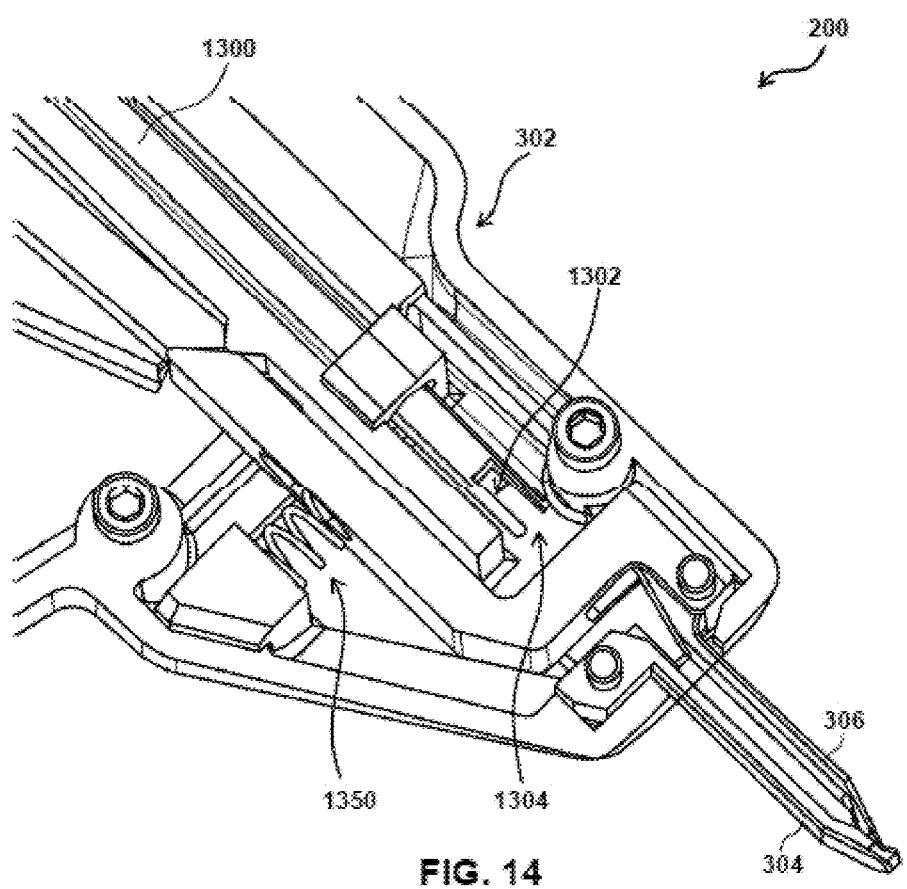
FIG. 14 illustrates another view of the exemplary implementation of the component advancer including the pusher tube coupled with the handle of the delivery system, in accordance with certain aspects of the disclosure.

FIGS. 13 and 14 illustrate different views of an exemplary implementation of a component advancer 302 including a pusher tube 1300 coupled with handle 300. As shown in FIG. 13, in some implementations, pusher tube 1300 may include a notch 1302 having a shape complementary to a portion of a component and configured to maintain the component in a particular orientation so as to avoid rotation of the component within system 200. FIG. 13 shows notch 1302 formed in a distal end 1304 of pusher tube 1300 configured to mate and/or otherwise engage with an end of a distal portion of a component (not shown in FIG. 13) to be implanted. Pusher tube 1300 may be configured to push, advance, and/or otherwise propel a component toward and/or into a patient via notch 1302 responsive to actuation of handle 300.

In some implementations, the proximal end 1308 of pusher tube 1300 may be coupled to handle 300 via a joint 1310. Joint 1310 may be configured to translate articulation of handle 300 by an operator into movement of pusher tube 1300 toward a patient. Joint 1310 may include one or more of a pin, an orifice, a hinge, and/or other components. In some implementations, component advancer 302 may include one or more guide components 1314 configured to guide pusher tube 1300 toward the patient responsive to the motion translation by joint 1310. In some implementations, guide components 1314 may include sleeves, clamps, clips, elbow shaped guide components, and/or other guide components. Guide components 1314 may also add a tensioning feature to ensure the proper tactile feedback to the physician during deployment. For example, if there is too much resistance through guide components 1314, then the handle 300 will be too difficult to move. Additionally, if there is too little resistance through the guide components 1314, then the handle 300 will have little tension and may depress freely to some degree when delivery system 200 is inverted.

FIG. 14 provides an enlarged view of distal end 1304 of pusher tube 1300. As shown in FIG. 14, notch 1302 is configured with a rectangular shape. This rectangular shape is configured to mate with and/or otherwise engage a corresponding rectangular portion of a component (e.g., as described below). The rectangular shape is configured to maintain the component in a specific orientation. For example, responsive to a component engaging pusher tube 1300 via notch 1302, opposing (e.g., parallel in this example) surfaces, and/or the perpendicular (in this example) end surface of the rectangular shape of notch 1302 may be configured to prevent rotation of the component. This notch shape is not intended to be limiting. Notch 1302 may have any shape that allows it to engage a corresponding portion of a component and prevent rotation of the component as described herein. For example, in some implementations, pusher tube 1300 may include one or more coupling features (e.g., in addition to or instead of the notch) configured to engage the portion of the component and configured to maintain the component in a particular orientation so as to avoid rotation of the component within system 200. These coupling features may include, for example, mechanical pins on either side of the pusher tube 1300 configured to mate with and/or otherwise engage receptacle features on a corresponding portion of a component.

Figure 15:
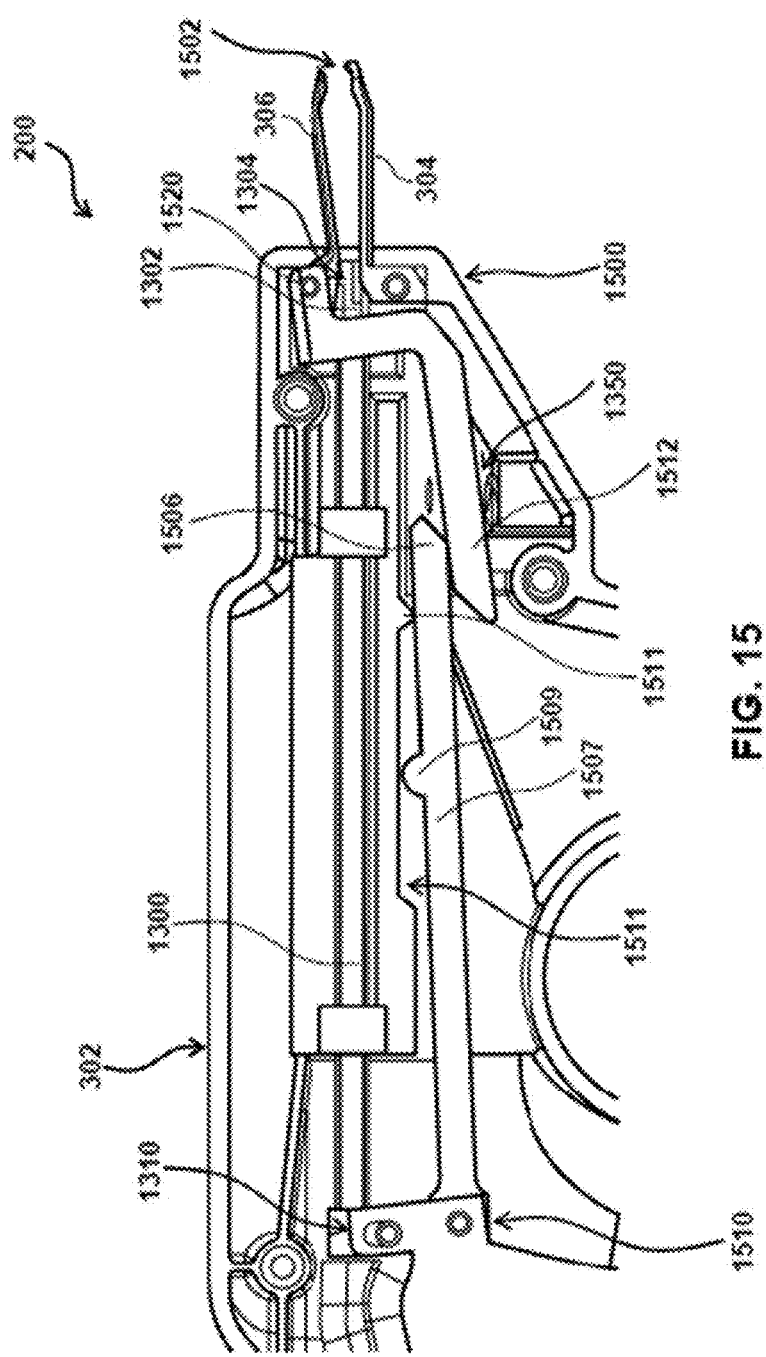
FIG. 15 illustrates the exemplary insertion tips in an open position, in accordance with certain aspects of the disclosure.

FIG. 15 illustrates insertion tips 304 and 306 in an open position 1502. FIG. 15 also illustrates pusher tube 1300 in an advanced position 1500, caused by actuation of handle 300 (not shown). Advanced position 1500 of pusher tube 1300 may be a position that is closer to insertion tips 304, 306 relative to the position of pusher tube 1300 shown in FIG. 14.

In some implementations, the component advancer 302 may include a wedge 1506 configured to move insertion tip 304 and/or 306 to the open position 1502. In some implementations, wedge 1506 may be configured to cause movement of the moveable insertion tip 306 and may or may not cause movement of insertion tip 304.

Wedge 1506 may be coupled to handle 300, for example, via a joint 1510 and/or other components. Joint 1510 may be configured to translate articulation of handle 300 by an operator into movement of the wedge 1506. Joint 1510 may include one or more of a pin, an orifice, a hinge, and/or other components. Wedge 1506 may be designed to include an elongated portion 1507 configured to extend from joint 1510 toward insertion tip 306. In some implementations, wedge 1506 may include a protrusion 1509 and/or other components configured to interact with corresponding parts 1511 of component advancer 302 to limit a travel distance of wedge 1506 toward insertion tip 306 and/or handle 300.

Wedge 1506 may also be slidably engaged with a portion 1512 of moveable insertion tip 306 such that actuation of handle 300 causes wedge 1506 to slide across portion 1512 of moveable insertion tip 306 in order to move moveable insertion tip 306 away from fixed insertion tip 304. For example, insertion tip 306 may be coupled to component advancer 302 via a hinge 1520. Wedge 1506 sliding across portion 1512 of moveable insertion tip 306 may cause moveable insertion tip to rotate about hinge 1520 to move moveable insertion tip 306 away from fixed insertion tip 304 and into open position 1502. In some implementations, moveable insertion tip 306 may be biased to a closed position. For example, a spring mechanism 1350 (also labeled in FIGS. 13 and 14) and/or other mechanisms may perform such biasing for insertion tip 306. Spring mechanism 1350 may force insertion tip 306 into the closed position until wedge 1506 is advanced across portion 1512, thereby separating insertion tip 306 from insertion tip 304.

In some implementations, as described above, first insertion tip 304 and second insertion tip 306 may be moveable. In some implementations, first insertion tip 304 and/or second insertion tip 306 may be biased to a closed position. For example, a spring mechanism similar to and/or the same as spring mechanism 1350 and/or other mechanisms may perform such biasing for first insertion tip 304 and/or second insertion tip 306. In such implementations, system 200 may comprise one or more wedges similar to and/or the same as wedge 1506 configured to cause movement of first and second insertion tips 304, 306. The one or more wedges may be coupled to handle 300 and slidably engaged with first and second insertion tips 304, 306 such that actuation of handle 300 may cause the one or more wedges to slide across one or more portions of first and second insertion tips 304, 306 to move first and second insertion tips 304, 306 away from each other.

In some implementations, system 200 may comprise a spring/lock mechanism or a rack and pinion system configured to engage and cause movement of moveable insertion tip 306. The spring/lock mechanism or the rack and pinion system may be configured to move moveable insertion tip 306 away from fixed insertion tip 304, for example. A spring lock design may include design elements that force the separation of insertion tips 304 and 306. One such example may include spring forces that remain locked in a compressed state until the component advancer or separating wedge activate a release trigger, thereby releasing the compressed spring force onto insertion tip 306, creating a separating force. These spring forces must be of sufficient magnitude to create the desired separation of tips 304 and 306 in the biological tissue. Alternatively, the spring compression may forceable close the insertion tips until the closing force is released by the actuator. Once released, the tips are then driven to a separating position by the advancement wedge mechanism, as described herein.

In some implementations, the component delivered by delivery system 200 (e.g., described above) may be an electrical lead for implantation in the patient. The lead may comprise a distal portion, one or more electrodes, a proximal portion, and/or other components. The distal portion may be configured to engage component advancer 302 of delivery system 200 (e.g., via notch 1302 shown in FIGS. 13 and 14). The distal portion may comprise the one or more electrodes. For example, the one or more electrodes may be coupled to the distal portion. The one or more electrodes may be configured to generate therapeutic energy for biological tissue of the patient. The therapeutic energy may be, for example, electrical pulses and/or other therapeutic energy. The biological tissue may be the heart (e.g., heart 118 shown in FIG. 1-FIG. 2C) and/or other biological tissue. The proximal portion may be coupled to the distal portion. The proximal portion may be configured to engage a controller when the lead is implanted in the patient. The controller may be configured to cause the one or more electrodes to generate the therapeutic energy, and/or perform other operations.

Figure 16:
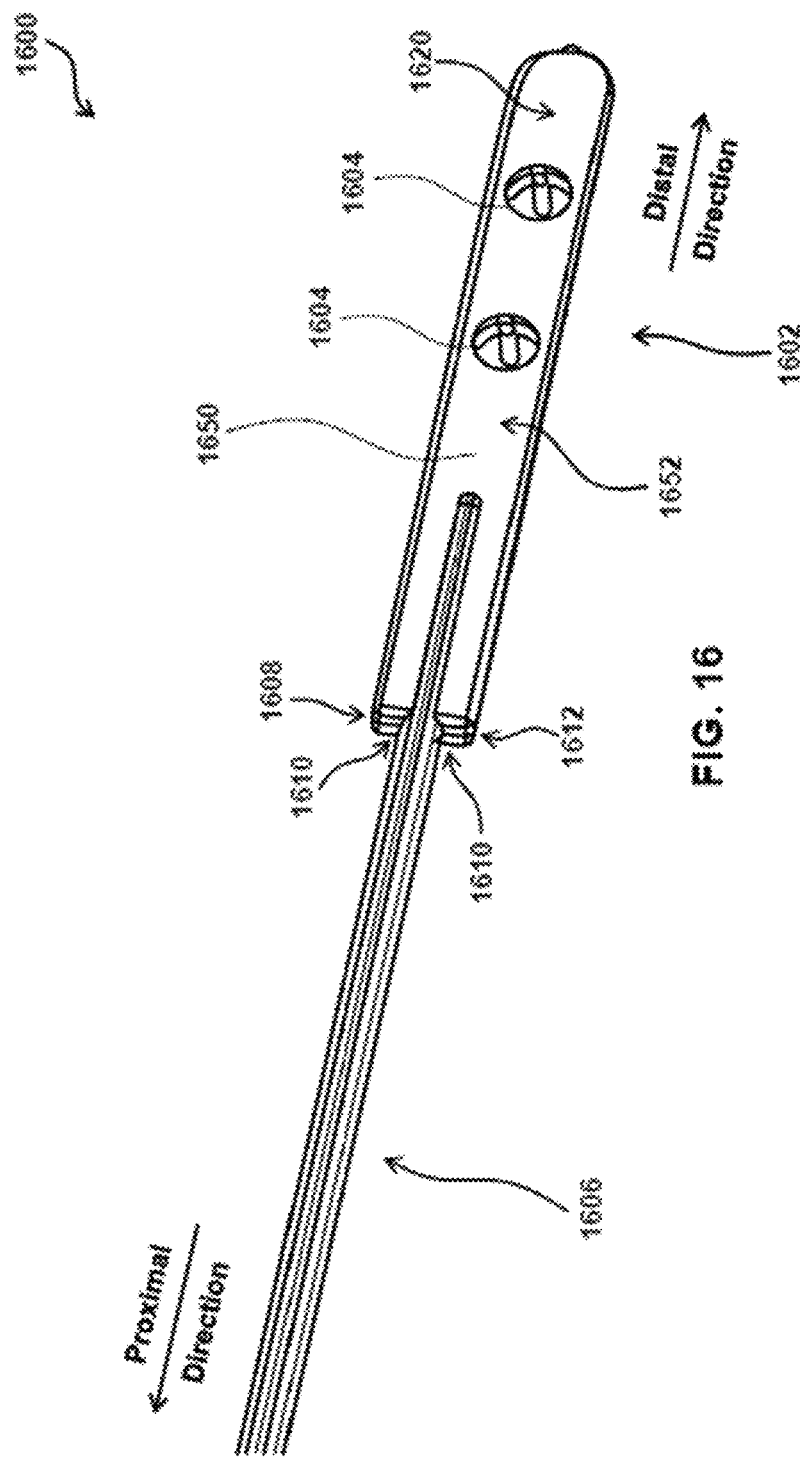
FIG. 16 illustrates an example implementation of an electrical lead, in accordance with certain aspects of the disclosure.

FIG. 16 illustrates an example implementation of an electrical lead 1600. Lead 1600 may comprise a distal portion 1602, one or more electrodes 1604, a proximal portion 1606, and/or other components. Distal portion 1602 may be configured to engage component advancer 302 of delivery system 200 (e.g., via notch 1302 shown in FIGS. 13 and 14). In some implementations, distal portion 1602 may comprise a proximal shoulder 1608. Proximal shoulder may be configured to engage component advancer 302 (e.g., via notch 1302 shown in FIGS. 13 and 14) such that lead 1600 is maintained in a particular orientation when lead 1600 is advanced into the patient. For example, in some implementations, proximal shoulder 1608 may comprise a flat surface 1610 (e.g., at a proximal end of distal portion 1602). In some implementations, proximal shoulder 1608 may comprise a rectangular shape 1612. Flat surface 1610 and/or rectangular shape 1612 may be configured to correspond to a (e.g., rectangular) shape of notch 1302 shown in FIGS. 13 and 14. In some implementations, transition surfaces between flat surface 1610 and other portions of distal portion 1602 may be chamfered, rounded, tapered, and/or have other shapes.

In some implementations, proximal shoulder 1608 may include one or more coupling features configured to engage component advancer 302 to maintain the lead in a particular orientation so as to avoid rotation of the lead when the lead is advanced into the patient. In some implementations, these coupling features may include receptacles for pins included in pusher tube 1300, clips, clamps, sockets, and/or other coupling features.

In some implementations, proximal shoulder 1608 may comprise the same material used for other portions of distal portion 1602. In some implementations, proximal shoulder may comprise a more rigid material, and the material may become less rigid across proximal shoulder 1608 toward distal end 1620 of distal portion 1602.

In some implementations, proximal shoulder 1608 may function as a fixation feature configured to make removal of lead 1600 from a patient (and/or notch 1302) more difficult. For example, when lead 1600 is deployed into the patient, lead 1600 may enter the patient led by a distal end 1620 of the distal portion 1602. However, retracting lead 1600 from the patient may require the retraction to overcome the flat and/or rectangular profile of flat surface 1610 and/or rectangular shape 1612, which should be met with more resistance. In some implementations, delivery system 200 (FIG. 3) may include a removal device comprising a sheath with a tapered proximal end that can be inserted over lead 1600 so that when it is desirable to intentionally remove lead 1600, the flat and/or rectangular profile of shoulder 1608 does not interact with the tissue on the way out.

Figure 17:
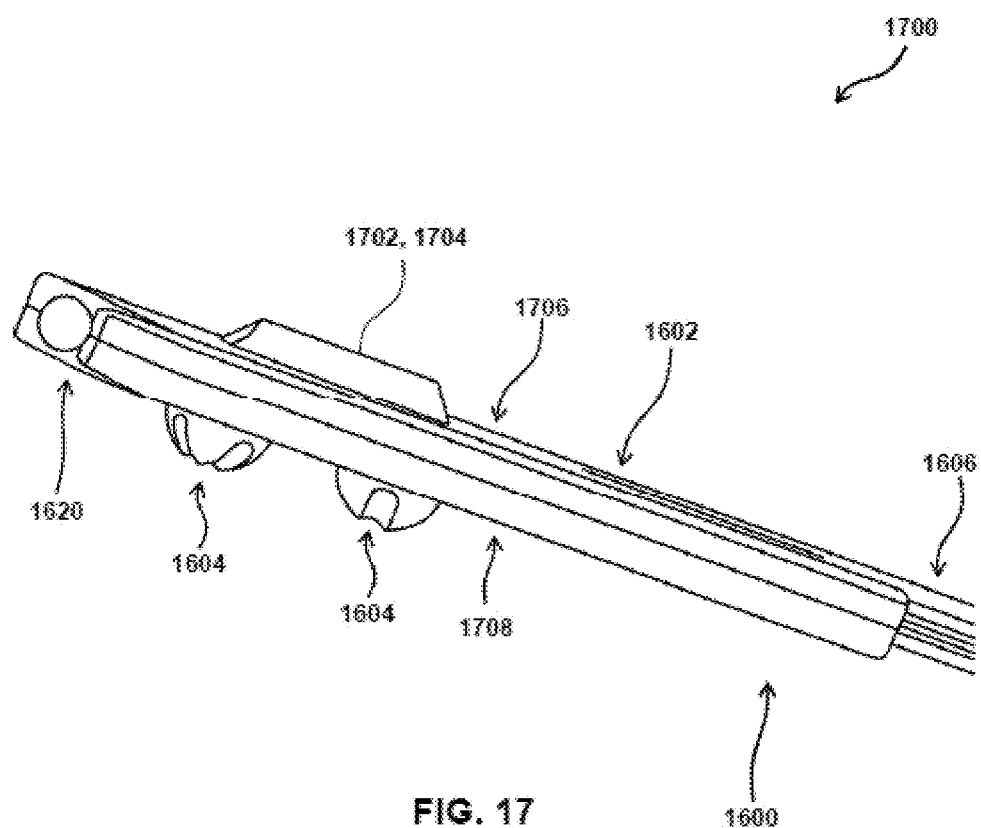
FIG. 17 illustrates another example implementation of an electrical lead, in accordance with certain aspects of the disclosure.

FIG. 17 illustrates another example implementation 1700 of electrical lead 1600. In some implementations, as shown in FIG. 17, distal portion 1602 may include one or more alignment features 1702 configured to engage delivery system 200 (FIG. 3) in a specific orientation. For example, alignment features 1702 of lead 1600 may include a rib 1704 and/or other alignment features configured to engage a groove in a channel (e.g., channel 500 shown in FIG. 5) of insertion tip 304 and/or 306 (FIG. 5). Rib 1704 may be on an opposite side 1706 of the lead 1600 relative to a side 1708 with electrodes 1604, for example. These features may enhance the guidance of lead 1600 through channel 500, facilitate alignment of lead 1600 in channel 500 (e.g., such that electrodes 1604 are oriented in a specific direction in tips 304, 306), prevent lead 1600 from exiting tips 304, 306 to one side or the other (as opposed to exiting out ends 404, 406 shown in FIG. 4), and/or have other functionality.

In some implementations, rib 1704 may be sized to be just large enough to fit within the groove in the channel 500. This may prevent the lead from moving within the closed insertion tips 304, 306 while the insertion tips are pushed through the intercostal muscle tissue. Additionally, rib 1704 may prevent an operator from pulling lead 1600 too far up into delivery system 200 (FIG. 3) when loading delivery system 200 with a lead (e.g., as described below). This may provide a clinical benefit, as described above, and/or have other advantages.

Figure 18:
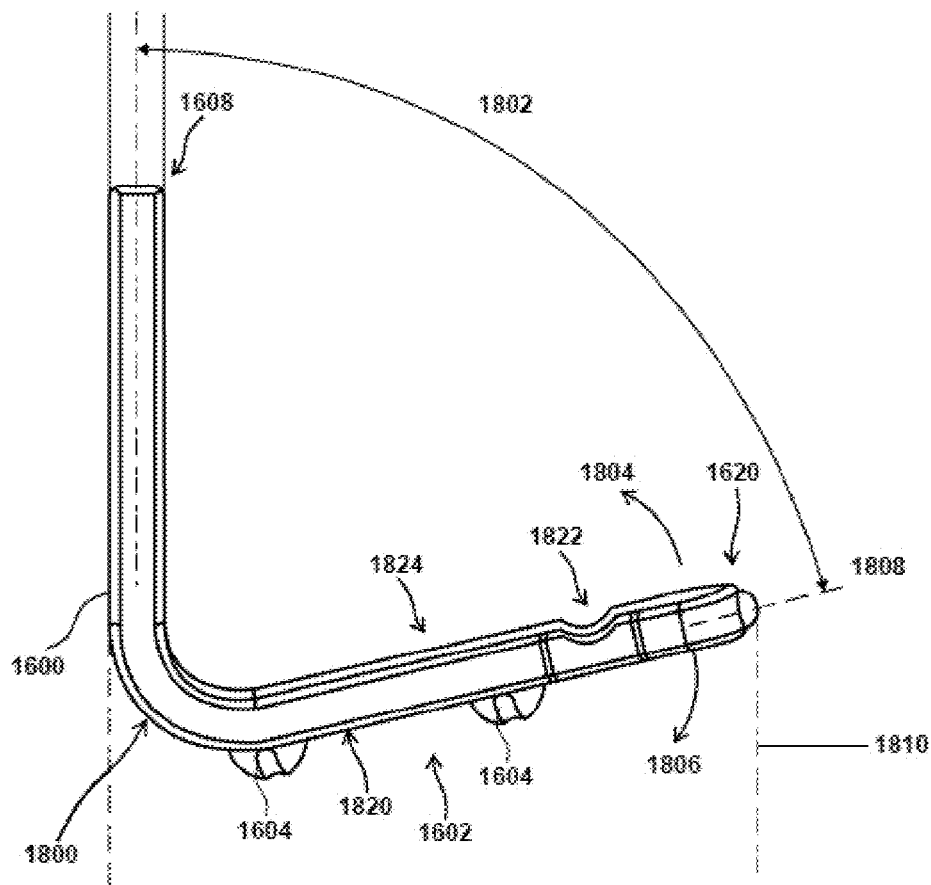
FIG. 18 illustrates a distal portion of an exemplary electrical lead bent in a predetermined direction, in accordance with certain aspects of the disclosure.

FIG. 18 illustrates distal portion 1602 of lead 1600 bent 1800 in a predetermined direction 1804. In some implementations, distal portion 1602 may be pre-formed to bend in predetermined direction 1804. The pre-forming may shape set distal portion 1602 with a specific shape, for example. In the example, shown in FIG. 18, the specific shape may form an acute angle 1802 between ends 1620, 1608 of distal portion 1602. The pre-forming may occur before lead 1600 is loaded into delivery system 200 (FIG. 3), for example. In some implementations, distal portion 1602 may comprise a shape memory material configured to bend in predetermined direction 1804 when lead 1600 exits delivery system 200. The shape memory material may comprise nitinol, a shape memory polymer, and/or other shape memory materials, for example. The preforming may include shape setting the shape memory material in the specific shape before lead 1600 is loaded into delivery system 200.

Distal portion 1602 may be configured to move in an opposite direction 1806, from a first position 1808 to a second position 1810 when lead 1600 enters the patient. In some implementations, first position 1808 may comprise an acute angle 1802 shape. In some implementations, the first position may comprise a ninety degree angle 1802 shape, or an obtuse angle 1802 shape. In some implementations, the second position may comprise a ninety degree angle 1802 shape, or an obtuse angle 1802 shape. Distal portion 1602 may be configured to move from first position 1808 to second position 1810 responsive to the shape memory material being heated to body temperature or by removal of an internal wire stylet, for example. In some implementations, this movement may cause an electrode side of distal portion 1602 to push electrodes 1604 into tissues toward a patient's heart, rather than retract away from such tissue and the heart. This may enhance electrical connectivity and/or accurately delivering therapeutic energy toward the patient's heart, for example.

Figure 19:
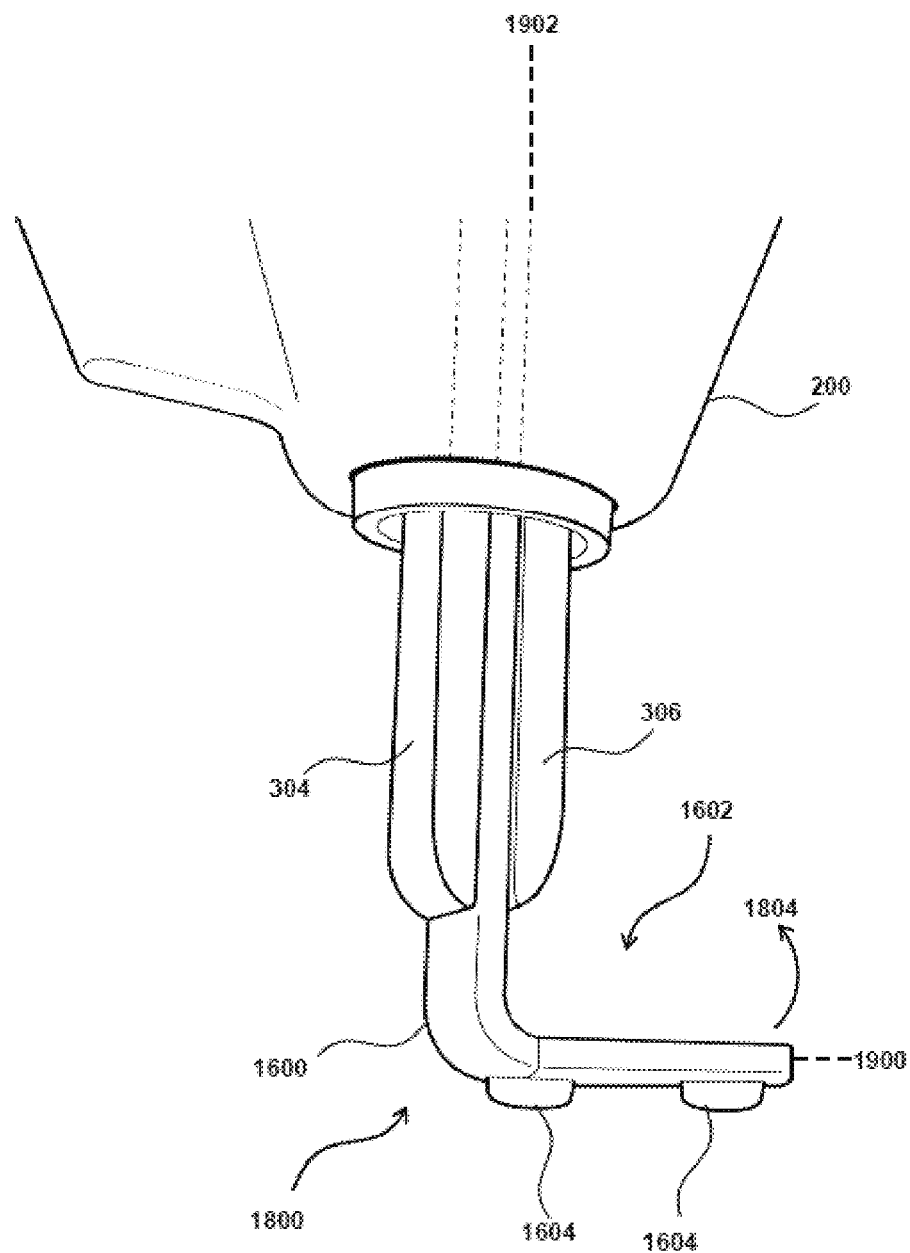
FIG. 19 illustrates the distal portion bending in the predetermined direction when the lead exits the delivery system, in accordance with certain aspects of the disclosure.

FIG. 19 illustrates distal portion 1602 bending 1800 in the predetermined direction 1804 when lead 1600 exits delivery system 200. In some implementations, as shown in FIG. 19, the predetermined direction may comprise a lateral and/or transverse direction 1900 relative to an orientation 1902 of insertion tips 304 and/or 306, a sternum of the patient, and/or other reference points in delivery system 200 and/or in the patient.

Figure 20:
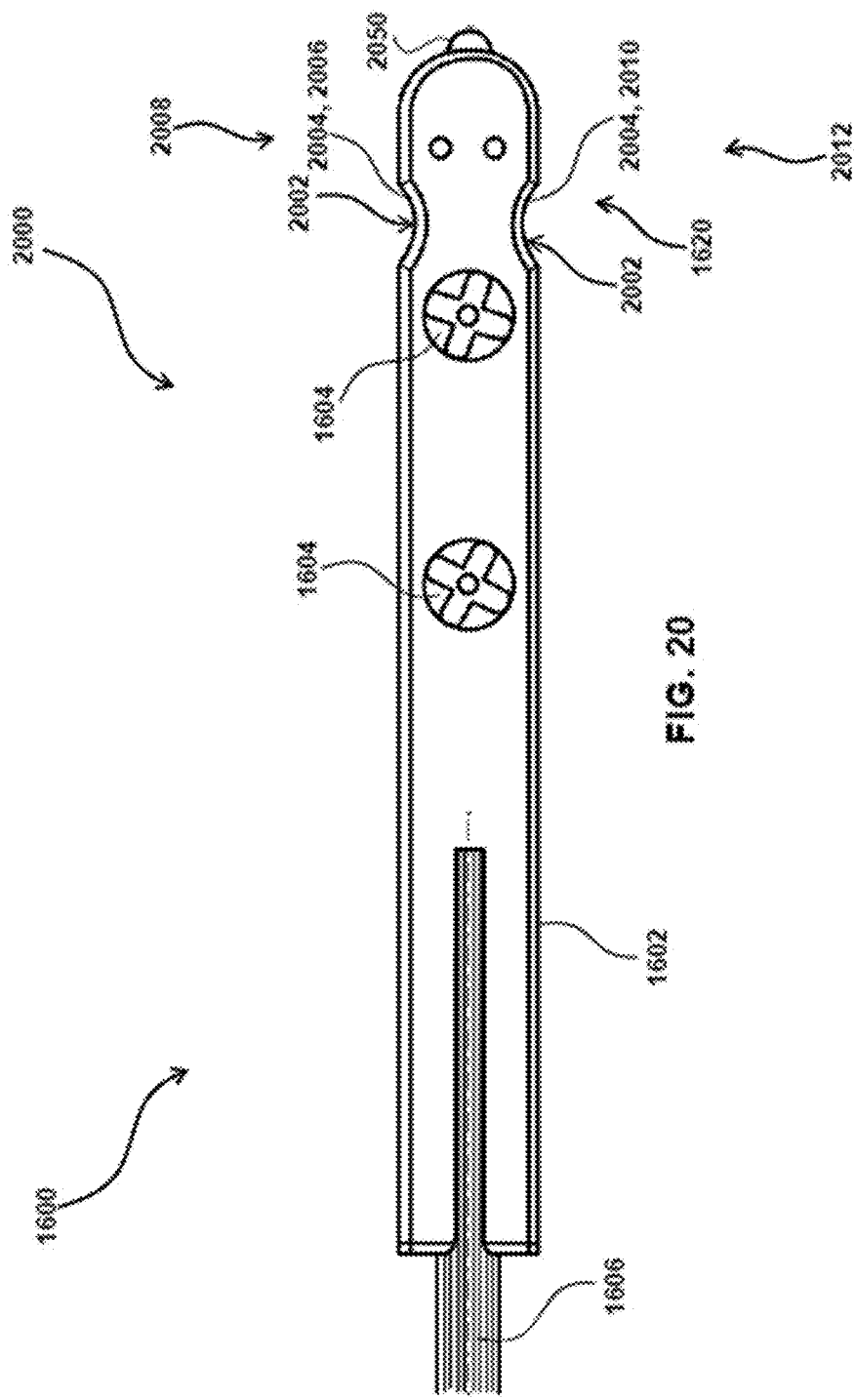
FIG. 20 illustrates an exemplary implementation of the distal portion of a lead, in accordance with certain aspects of the disclosure.
Figure 21:
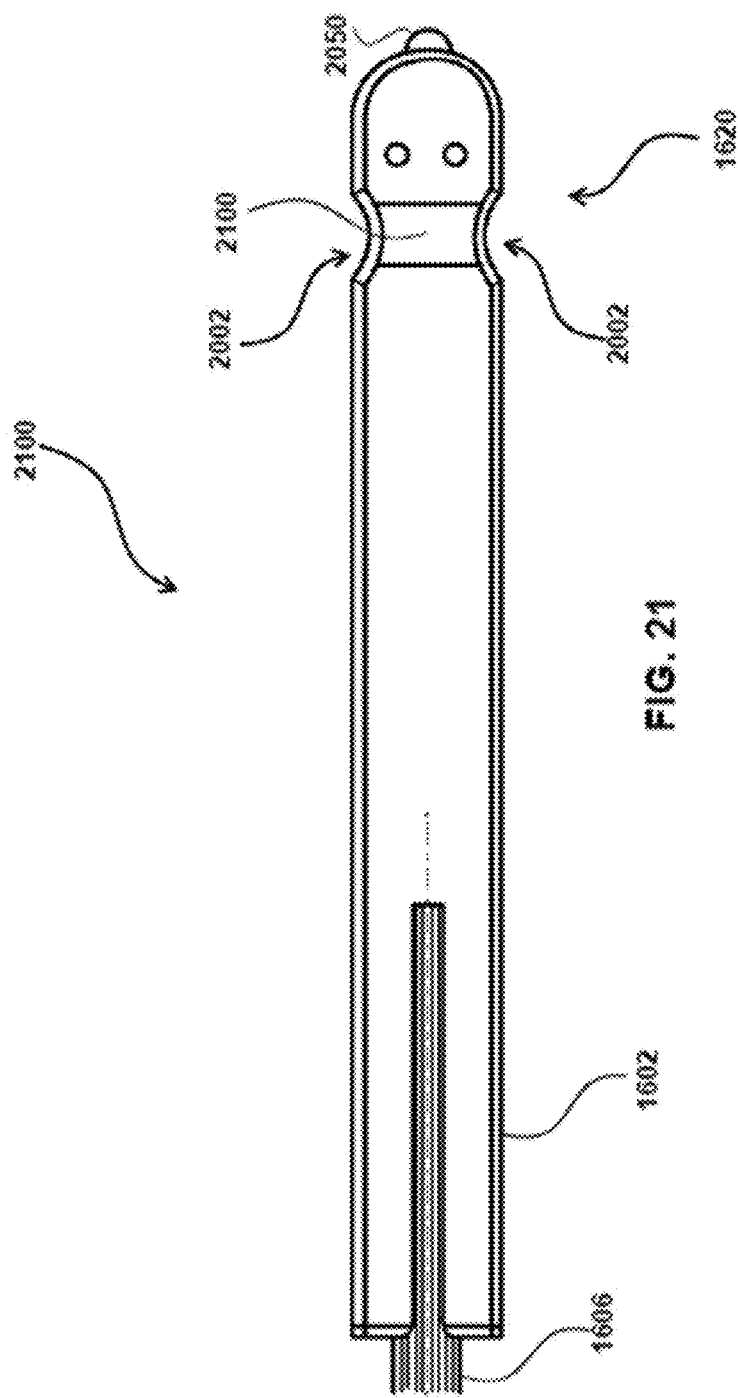
FIG. 21 illustrates another exemplary implementation of the distal portion of a lead, in accordance with certain aspects of the disclosure.

FIGS. 20 and 21 illustrate implementations 2000 and 2100 of distal portion 1602 of lead 1600. In some implementations, distal portion 1602 may include distal end 1620 and distal end 1620 may include a flexible portion 2002 so as to allow distal end 1620 to change course when encountering sufficient resistance traveling through the biological tissue of the patient. In some implementations, distal end 1620 may be at least partially paddle shaped, and/or have other shapes. The paddle shape may allow more surface area of distal end 1620 to contact tissue so the tissue is then exerting more force back on distal end 1620, making distal end 1620 bend and flex via flexible portion 2002. In some implementations, flexible portion 2002 may comprise a material that flexes more easily relative to a material of another area of distal portion 1602. For example, flexible portion 2002 may comprise a different polymer relative to other areas of distal portion 1602, a metal, and/or other materials.

In some implementations, flexible portion 2002 may comprise one or more cutouts 2004. The one or more cutouts 2004 may comprise one or more areas having a reduced cross section compared to other areas of distal portion 1602. The one or more cutouts 2004 may be formed by tapering portions of distal portion 1602, removing material from distal portion 1602, and/or forming cutouts 2004 in other ways. The cutouts may increase the flexibility of distal end 1620, increase a surface area of distal end 1620 to drive distal end 1620 in a desired direction, and/or have other purposes. Cutouts 2004 may reduce a cross-sectional area of distal end 1620, making distal end 1620 more flexible, and making distal end 1620 easier to deflect. Without such cutouts, for example, distal end 1620 may be too rigid or strong, and drive lead 1600 in a direction that causes undesirable damage to organs and/or tissues within the anterior mediastinum (e.g., the pericardium or heart).

In some implementations, the one or more areas having the reduced cross section (e.g., the cutouts) include a first area (e.g., cutout) 2006 on a first side 2008 of distal end 1620. The one or more areas having the reduced cross section (e.g., cutouts) may include first area 2006 on first side 2008 of distal end 1620 and a second area 2010 on a second, opposite side 2012 of distal end 1620. This may appear to form a neck and/or other features in distal portion 1602, for example.

In some implementations, as shown in FIG. 21, the one or more areas having the reduced cross section may include one or more cutouts 2100 that surround distal end 1620. Referring back to FIG. 18, in some implementations, distal portion 1602 may have a surface 1820 that includes one or more electrodes 1604, and a cut out 1822 in a surface 1824 of distal end 1620 opposite surface 1820 with one or more electrodes 1604. This positioning of cutout 1822 may promote a bias of distal end 1620 back toward proximal shoulder 1608 (FIG. 16) of lead 1600. In some implementations, cutout 1822 may create a bias (depending upon the location of cutout 2100) acutely in direction 1804 or obtusely in direction 1806. Similarly, alternative cutouts 2100 may be inserted to bias distal end 1620 in other directions.

Returning to FIGS. 20 and 21, in some implementations, flexible portion 2002 may be configured to cause distal end 1620 to be biased to change course in a particular direction. Distal end 1620 may change course in a particular direction responsive to encountering resistance from biological tissue in a patient, for example. In some implementations, biasing distal end 1620 to change course in a particular direction may comprise biasing distal end 1620 to maintain electrodes 1604 on a side of distal portion 1602 that faces the heart of the patient. For example, distal end 1620 may be configured to flex or bend to push through a resistive portion of biological material without twisting or rotating to change an orientation of electrodes 1604.

In some implementations, distal portion 1602 may include a distal tip 2050 located at a tip of distal end 1620. Distal tip 2050 may be smaller than distal end 1620. Distal tip 2050 may be more rigid compared to other portions of distal end 2050. For example, distal tip 2050 may be formed from metal (e.g., that is harder than other metal/polymers used for other portions of distal end 1620), hardened metal, a ceramic, a hard plastic, and/or other materials. In some implementations, distal tip 2050 may be blunt, but configured to push through biological tissue such as the endothoracic fascia, and/or other biological tissue. In some implementations, distal tip 2050 may have a hemispherical shape, and/or other blunt shapes that may still push through biological tissue.

In some implementations, distal tip 2050 may be configured to function as an electrode (e.g., as described herein). This may facilitate multiple sense/pace vectors being programmed and used without the need to reposition electrical lead 1600. For example, once the electrical lead 1600 is positioned, electrical connections can be made to the electrodes 1604 and cardiac pacing and sensing evaluations performed. If unsatisfactory pacing and/or sensing performance is noted, an electrical connection may be switched from one of the electrodes 1604 to the distal electrode 2050. Cardiac pacing and/or sensing parameter testing may then be retested between one of the electrodes 1604 and the distal electrode 2050. Any combination of two electrodes can be envisioned for the delivery of electrical therapy and sensing of cardiac activity, including the combination of multiple electrodes to create one virtual electrode, then used in conjunction with a remaining electrode or electrode pairing. Additionally, electrode pairing may be selectively switched for electrical therapy delivery vs. physiological sensing.

Returning to FIG. 16, in some implementations, at least a portion of distal portion 1602 of lead 1600 may comprise two parallel planar surfaces 1650. One or more electrodes 1604 may be located on one of the parallel planar surfaces, for example. Parallel planar surfaces 1650 may comprise elongated, substantially flat surfaces, for example. (Only one parallel planar surface 1650 is shown in FIG. 16. The other parallel planar surface 1650 may be located on a side of distal portion 1602 opposite electrodes 1604, for example.) In some implementations, at least a portion 1652 of distal portion 1602 of lead 1600 may comprise a rectangular prism including the two parallel planar surfaces 1650.

Because the proximal end of the distal portion 1602 may be positioned within the intercostal muscle tissue (while the distal end of the distal portion 1602 resides in the mediastinum), the elongated, substantially flat surfaces of proximal end of the distal portion 1602 may reduce and/or prevent rotation of distal portion 1602 within the muscle tissue and within the mediastinum. In contrast, a tubular element may be free to rotate. In some implementations, distal portion 1602 may include one or more elements configured to engage and/or catch tissue to prevent rotation, prevent egress and/or further ingress of distal portion 1602, and/or prevent other movement. Examples of these elements may include tines, hooks, and/or other elements that are likely to catch and/or hold onto biological tissue. In some implementations, the bending of distal portion 1602 (e.g., as described above related to FIG. 18) may also function to resist rotation and/or other unintended movement of distal portion 1602 in a patient. Distal portion 1602 may also be designed with multiple segments, with small separating gaps between each segment, designed to increase stability within the tissue, increase the force required for lead retraction or to promote tissue ingrowth within the distal portion 1602.

Figure 22:
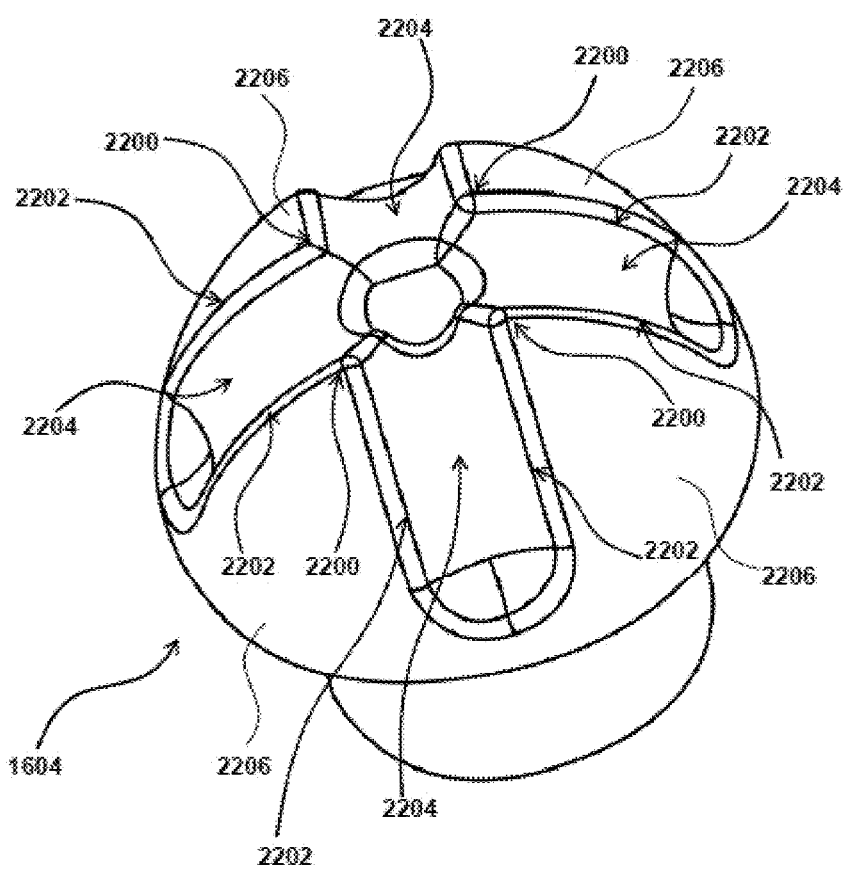
FIG. 22 illustrates an example of an electrode, in accordance with certain aspects of the disclosure.

FIG. 22 illustrates an example of an electrode 1604. In some implementations, an electrode 1604 may be formed from a conductive metal and/or other materials. Electrodes 1604 may be configured to couple with distal portion 1602 of lead 1600, proximal portion 1606 (e.g., wiring configured to conduct an electrical signal from a controller) of lead 1600, and/or other portions of lead 1600. In some implementations, distal portion 1602 may comprise a rigid material, with an area of distal portion 1602 around electrodes 1604 comprising a relatively softer material. One or more electrodes 1604 may protrude from distal portion 1602 of lead 1600 (e.g., as shown in FIG. 16). Electrodes 1604 may be configured to provide electrical stimulation to the patient or to sense electrical or other physiologic activity from the patient (e.g., as described above). In some implementations, one or more electrodes 1604 may include one or both of corners 2200 and edges 2202 configured to enhance a current density in one or more electrodes 1604. In some implementations, at least one of the electrodes 1604 may comprise one or more channels 2204 on a surface 2206 of the electrode 1604. In some implementations, at least one of the one or more electrodes 1604 may comprise two intersecting channels 2204 on surface 2206 of the electrode 1604. In some implementations, the channels 2204 may be configured to increase a surface area of an electrode 1604 that may come into contact with biological tissue of a patient. Other channel designs are contemplated.

Figure 23:
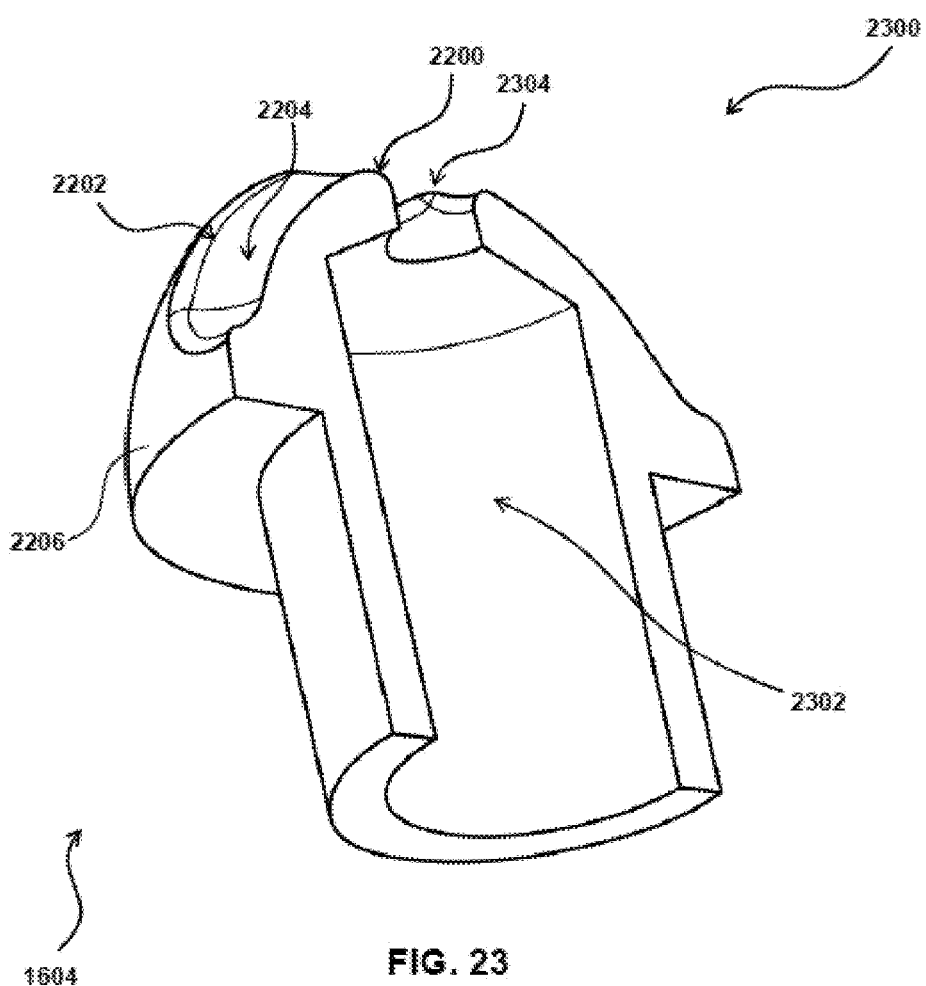
FIG. 23 illustrates a cross section of the example electrode, in accordance with certain aspects of the disclosure.

FIG. 23 illustrates a cross section 2300 of example electrode 1604. In some implementations, as shown in FIG. 23, at least one of the one or more electrodes 1604 may be at least partially hollow 2302. In such implementations, an electrode 1604 may include a hole 2304 configured to allow the ingress of fluid. In some implementations, an electrode 1604 may include a conductive mesh (not shown in FIG. 23) within hollow area 2302. The conductive mesh may be formed by conductive wiring, a porous sheet of conductive material, and/or other conductive meshes electrically coupled to electrode 1604. In some implementations, an electrode 1604 may include electrically coupled scaffolding within hollow area 2302. The scaffolding may be formed by one or more conductive beams and/or members placed in and/or across hollow area 2302, and/or other scaffolding.

These and/or other features of electrodes 1604 may be configured to increase a surface area and/or current density of an electrode 1604. For example, channels in electrodes 1604 may expose more surface area of an electrode 1604, and/or create edges and corners that increase current density, without increasing a size (e.g., the diameter) of an electrode 1604. The corners, hollow areas, conductive mesh, and/or scaffolding may function in a similar way.

In some implementations, an anti-inflammatory agent may be incorporated by coating or other means to electrode 1604. For example, a steroid material may be included in hollow area 2302 to reduce the patient's tissue inflammatory response.

Figure 24:
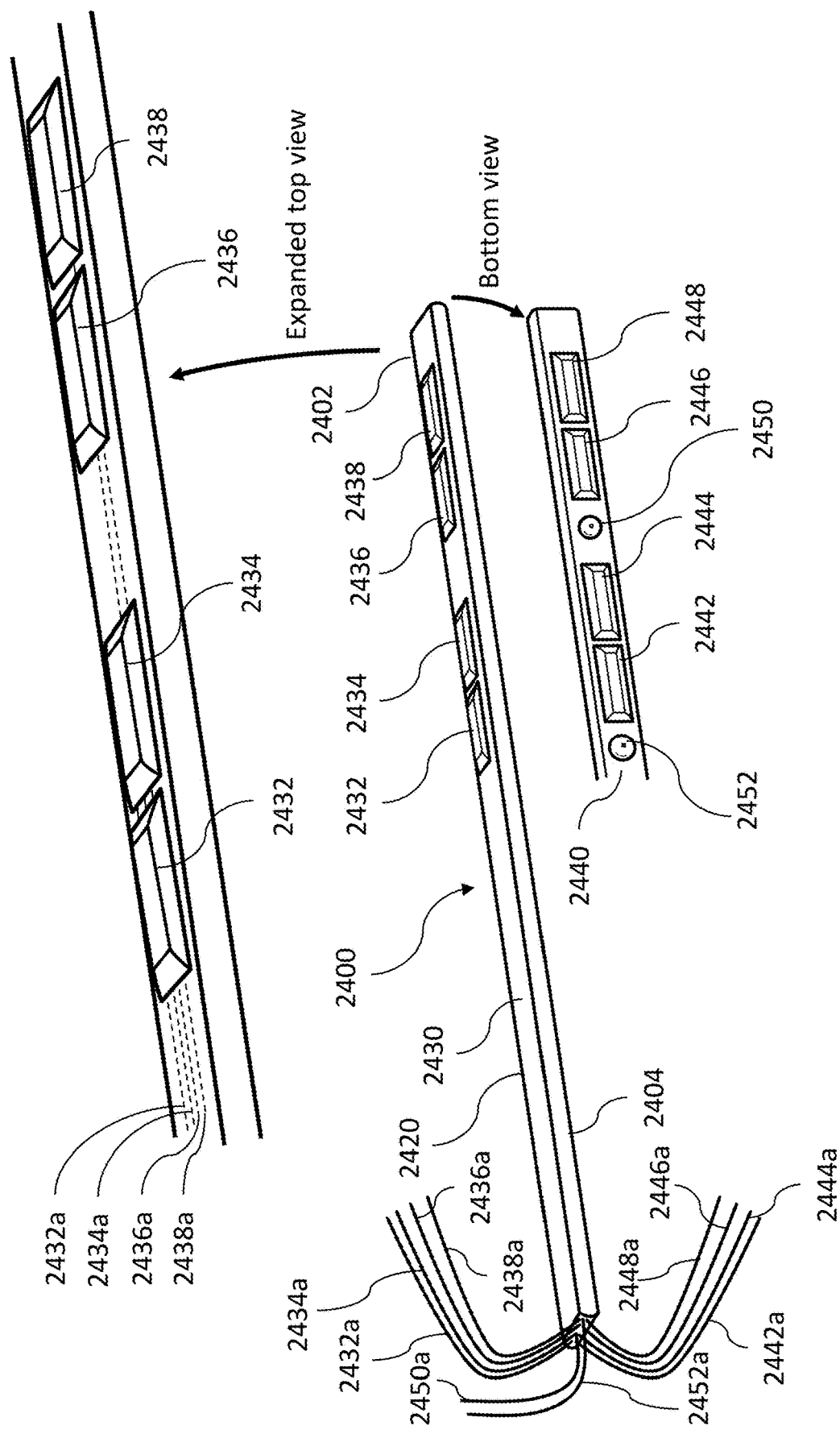
FIG. 24 is a diagram illustrating a simplified perspective view of an exemplary directional lead with panel electrodes in accordance with certain aspects of the present disclosure.
Figure 25:
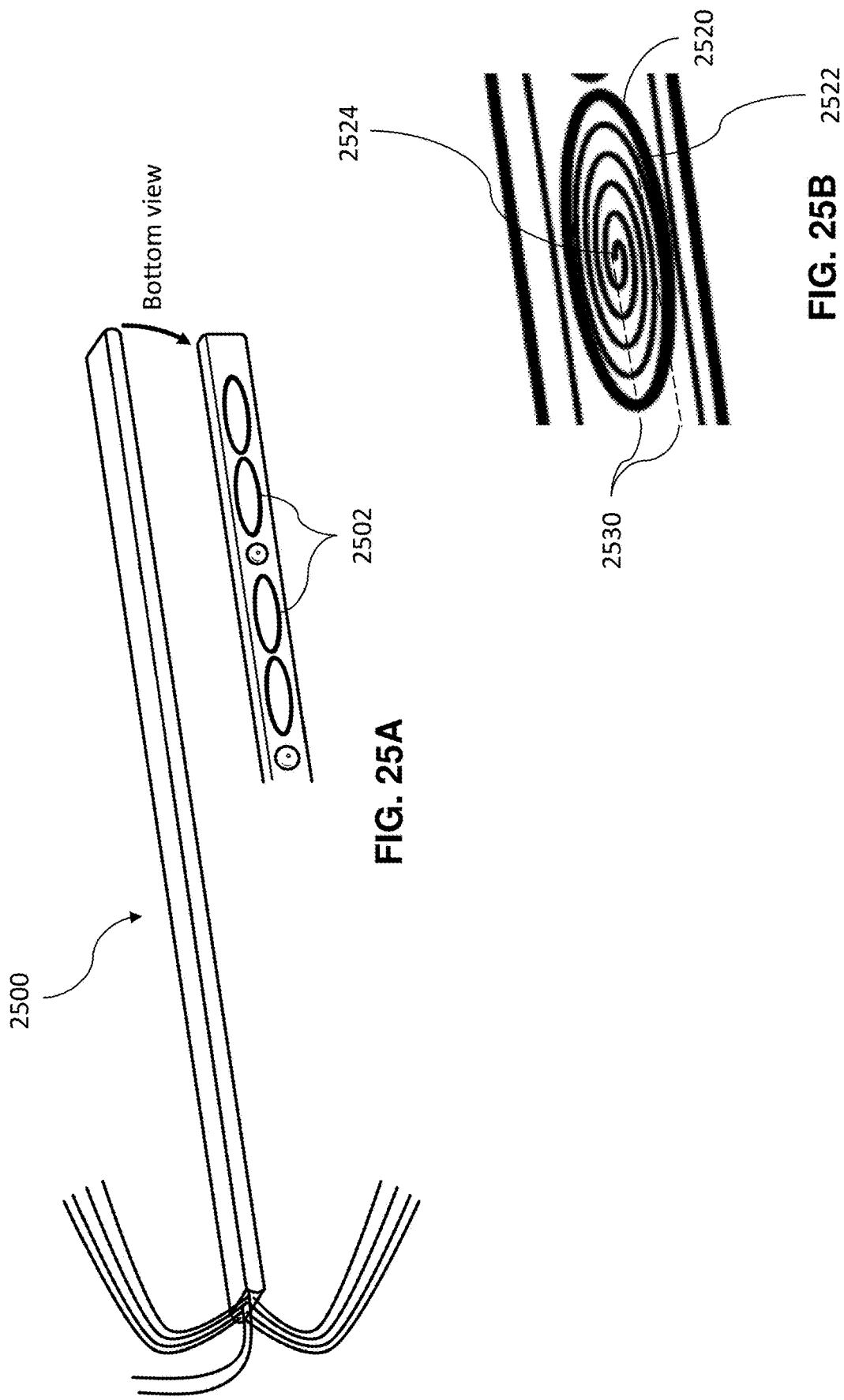
FIG. 25A is a diagram illustrating a simplified perspective view of an exemplary directional lead with elliptical panel electrodes in accordance with certain aspects of the present disclosure.
FIG. 25B is a diagram illustrating a simplified perspective view of an exemplary directional lead with elliptical coil electrodes in accordance with certain aspects of the present disclosure.

FIG. 24 illustrates an embodiment of a lead 2400 with parallel planar surfaces that include one or more electrodes. This electrical lead (or simply "lead") for implantation in a patient is shown as having a distal portion 2402 (e.g., a portion deployed in a patient) and a proximal portion 2404. The distal portion can include one or more electrodes that are configured to generate therapeutic energy for biological tissue of a patient. The proximal portion can be coupled to the distal portion and configured to engage a controller that can be configured to cause the one or more electrodes to generate therapeutic energy.

At least a portion of the lead (e.g., the distal portion) may include two parallel planar surfaces that can form a rectangular prism. Various embodiments of the leads described herein can thus provide a distal portion configured for extravascular implantation. For example, these planar surfaces are well-suited for implantation near and/or along a patient's sternum. As used herein, the term "rectangular prism" refers to a lead having rectangular sides and/or cross section. Some sides/cross-sections may be square, as such is a type of rectangle. Also, a "rectangular prism" allows for small deviations from being perfectly rectangular. For example, edges may be rounded to prevent damage to patient tissues and some rectangular faces may have a slight degree of curvature (e.g., less than 30°).

The distal portion of the lead may include defibrillation electrodes or cardiac pacing electrodes. In some embodiments, the electrodes on the lead may include both defibrillation electrodes and cardiac pacing electrodes. One embodiment, depicted in FIG. 24, shows a lead body 2420 with a top side 2430, which may include electrodes 2432, 2434, 2436, 2438. Also shown as an inset is part of the bottom side 2440 of the lead (which would normally be obscured by the perspective view). The bottom side can have a similar, or identical, set of electrodes (2442, 2444, 2446, 2448). In the embodiments described herein, particularly those referencing FIGS. 24-27, electrodes are may described with reference to a particular "side" of a lead. However, it is contemplated that electrodes can be configured to provide directional stimulation from any side of the lead body. For example, rather than having electrodes present on the top side and the bottom side of a directional lead, there may be electrodes present on a top side and a left side of the directional lead. Accordingly, no particular combination, disposition, or shape of the disclosed electrodes should be considered essential to the present disclosure, other embodiments not specifically described are contemplated.

As shown in FIG. 24, the electrodes can be thin metallic plates (e.g., stainless steel, copper, other conductive materials, etc.) of a generally planar shape. The thin metallic plates can be rectangular (as shown in FIG. 24) but may also be elliptical (as shown in FIG. 25A). The panel electrodes may have rounded corners or edges to avoid damaging patient tissue. Certain embodiments of the thin metallic plates can be on one or both of the two parallel planar surfaces.

The embodiment of FIG. 24 depicts defibrillation panel electrodes along with a pacing anode 2450 and pacing cathode 2452. Although the embodiments depicted in the figures include pacing electrodes only on the bottom of the lead, it is contemplated that the lead may alternatively include pacing electrodes on either or both sides of the lead. In addition, the location of the anode and cathode may be reversed or moved to different locations on the lead. Additionally, multiple pacing anodes 2450 or pacing cathodes 2452 may be included on the same side of the lead.

While the embodiment of FIG. 24 depicts four top defibrillation electrodes and four bottom defibrillation electrodes, it is contemplated that various other arrangements and placements may be utilized, for example, two defibrillation electrodes on top and two defibrillation electrodes on bottom, etc. Also, it is contemplated that any of the corresponding top and bottom defibrillation electrodes may be connected, thereby delivering directional electrical energy simultaneously away from the top side and the bottom side of the lead body (e.g., electrodes 2432 and 2442 may be connected or formed as a single conductive element that extends through the lead body).

Figure 29:
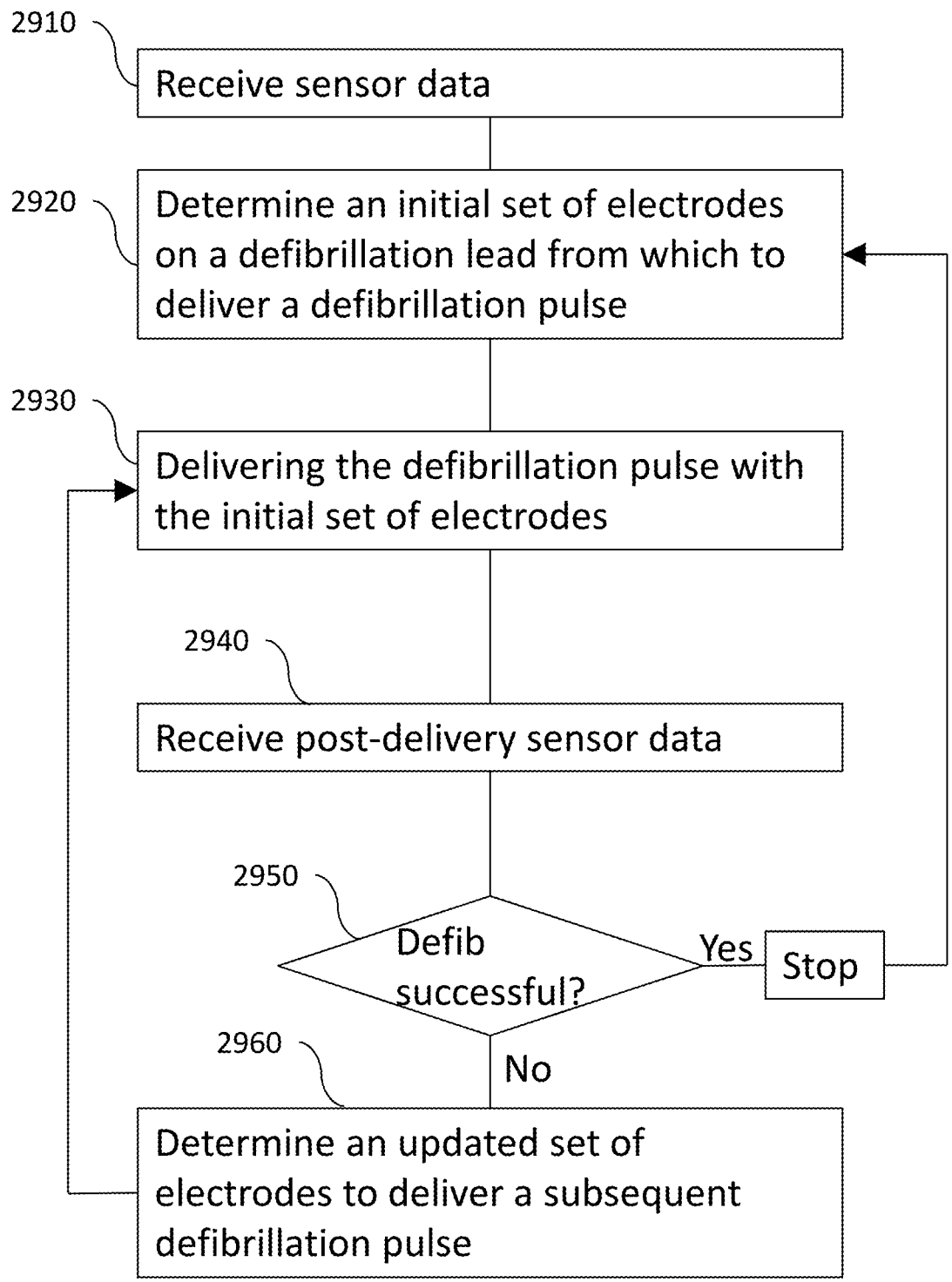
FIG. 29 is a flow chart illustrating an exemplary process for performing defibrillation in accordance with certain aspects of the present disclosure.

FIG. 24 also depicts leads wires (2432a, 2434a, 2436a, 2438a, 2442a, 2444a, 2446a, 2448a, 2450a, 2452a) that extend through or along the lead body and connect to their respective electrodes. The expanded top view illustrates the lead wires (2432a, 2434a, 2436a, 2438a) for the electrodes (2432, 2434, 2436, 2438) on the top of the lead. The lead wires can conduct defibrillation and pacing pulses and/or sensing signals to and/or from a connected pulse generator or computer that controls or processes signals. Similar to other embodiments described herein, the illustrated defibrillation electrodes can be energized in any combination to provide specific defibrillation vectors for delivering defibrillation pulses. Such energization can include varying the current through the defibrillation electrodes and thereby varying the defibrillation energy delivered to the heart. Aspects of such functionality are further described with reference to FIG. 29. Furthermore, multiple or all electrodes may be electrically tied together within the lead body such that only one lead wire emerges at the distal portion 2404. In some embodiments, the pacing cathode and anode are independently routed to the distal portion of the lead along with one defibrillation lead wire that is connected to all of the defibrillation electrodes. Alternatively, the pacing cathode may be independent; however, the pacing anode and defibrillation electrodes are electrically tied together within the lead body. In some instances, the defibrillation electrodes can act as the pacing anode for cardiac sensing and pacing therapies, while also serving as the defibrillation electrodes during defibrillation energy delivery. Additionally, redundant wires may be placed to ensure electrical connection with the various electrodes in the even that one wire is compromised.

While the depicted components (e.g., directional lead, lead body, electrodes, anode, cathode, etc.) can be designed to various dimensions, in an exemplary implementation, the lead body may have a width of approximately 5 mm and a thickness of approximately 2 mm, with panel electrodes being approximately 20 mm in length by 5 mm in width. Also, the pacing anodes and/or cathodes can have an approximately a 2-5 mm diameter. As used herein, the term "approximately," when describing dimensions, means that small deviations are permitted such as typical manufacturing tolerances but may also include variations such as within 30% of stated dimensions.

The embodiments described herein are not intended to be limited to two opposite sides of a planar lead body. The teachings can apply similarly to a lead body that is round, with electrodes located at different angles around the circumference of the lead body.

FIG. 25A illustrates an embodiment of a lead 2500 with elliptical electrodes 2502. Such elliptical electrodes can be similar in many respects to the rectangular thin metallic plate electrodes described above but can have the benefit of providing a different current distribution to the patient than rectangular electrodes.

FIG. 25B illustrates an embodiment similar to the embodiment described with reference to FIG. 25A but instead of the electrodes being planar (e.g., a continuous sheet or plate) the defibrillation electrodes may be constructed as elliptical spiral coils 2520. Such spiral electrodes can have electrical current passed along the conductor in a spiral pattern. The conductors forming the spiral may have cross-sections that are round (e.g., wire), rectangular (e.g., flat), etc. The dimensions of the overall spiral can be similar to those described above with regard to the planar electrodes of FIG. 24. The configuration of the spiral can be such that there is a sufficient spacing (e.g., approximately 0.05 mm) to allow for flexibility which eases the delivery of the lead as compared to rigid panels. It is contemplated that the spiral can be constructed such that most of the area of the electrode is occupied by conductor, though in some implementations, the central portion may not be fully covered or may be covered in a looser spiral to manufacturing constraints. In some embodiments, the surface area of the spiral coil can be greater than 50%, 60 to 70%, 80 to 90%, or greater than 95% of the surface area enclosed by the largest perimeter of the spiral.

As shown in the magnified inset, spiral electrodes may have an inner termination 2522 and an outer termination 2524. The inner and outer terminations can be connected to corresponding connecting lead wires 2530 and such lead wires may extend through the lead body similarly to the configuration described with respect to FIG. 24. Pairs of leads (i.e., a lead for the inner termination and a lead for the outer termination) may be braided to reduce electrical interference. However, in some implementations, there may be a single lead connected to either the inner termination or the outer termination of the spiral. In such implementations, only the patient tissue acts as a return for the delivered current.

Figure 26:
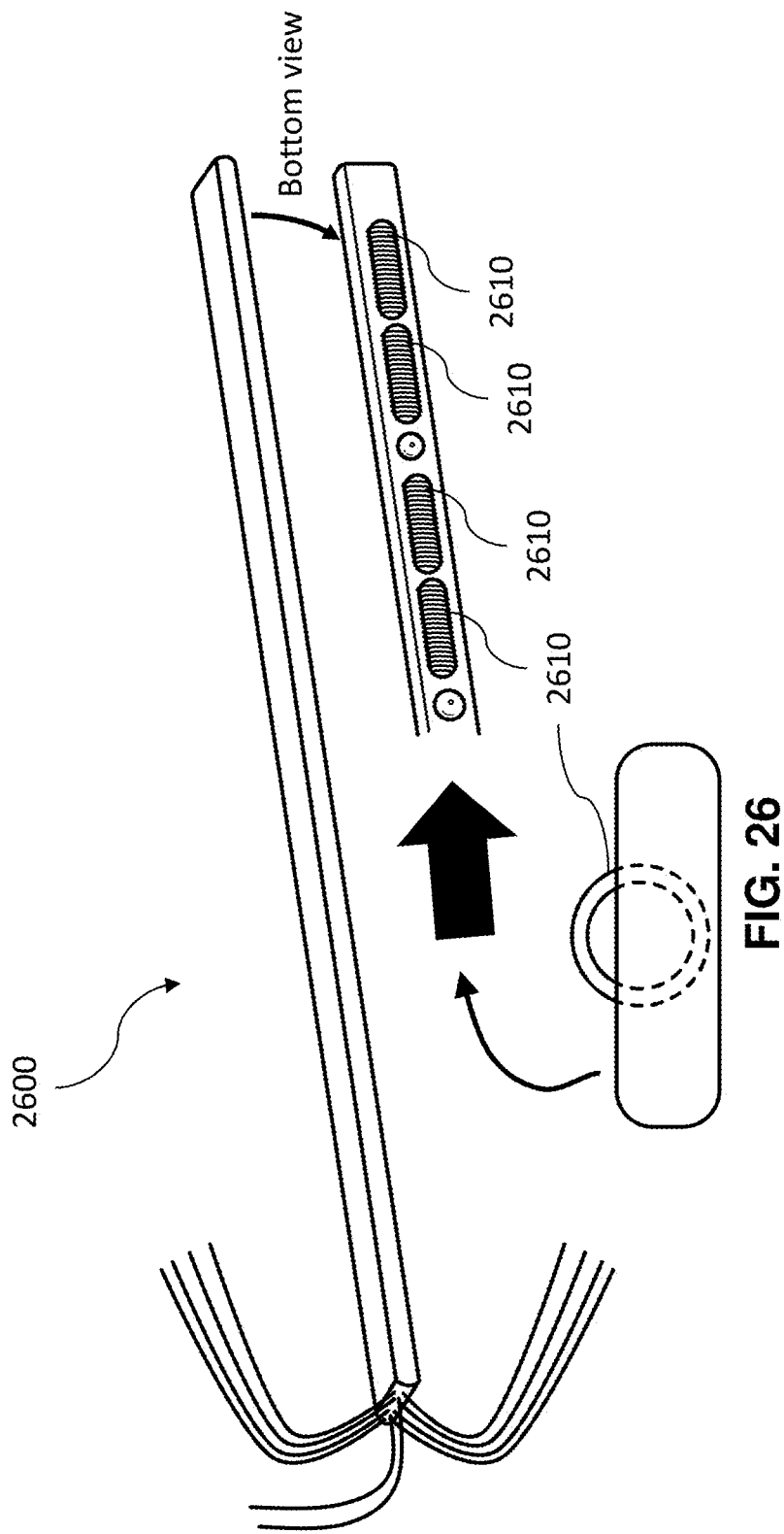
FIG. 26 is a diagram illustrating a simplified perspective view of an exemplary directional lead with embedded directional electrodes in accordance with certain aspects of the present disclosure.

FIG. 26 illustrates an embodiment of a lead 2600 that has embedded electrodes 2610. Such embedded electrodes 2610 can be similar to previous embodiments in that they provide directional stimulation. To provide this directional stimulation, electrical energy from the embedded electrodes may be partially blocked by the insulating lead body. As shown in the depicted embodiment, embedded electrodes can be partially embedded in the portion of the distal portion of the lead having the two planar parallel surfaces. In this way, the partially embedded electrodes can have an embedded portion and an exposed portion.

In the embodiment of FIG. 26, the embedded electrodes are shown as helical coils that are oriented in the longitudinal direction (i.e., along the lengthwise direction of the lead body). The inset of FIG. 26 shows a simplified end view of the lead body with a portion of the embedded electrode being outside the lead body and the remainder of the embedded electrode being inside the lead body (as indicated by the dashed lines). As can be seen, the portion of the embedded electrode outside the lead body can thus have a similar surface area to the previously described planar electrodes. However, due to the helical shape of the embedded electrode, the portion that is extending from the lead body can have a greater vertical extent (i.e., can bulge outward) as compared to a thin metallic plate electrode and thus increase the available surface area.

The electrodes depicted in FIG. 26 are configured such that the exposed portion is on only one of the two planar parallel surfaces. However, it is contemplated that in other embodiments the electrodes may have portions that extend from more than one face. For example, were the electrode larger in diameter and/or shifted downward in the inset, there could be portions extending from both of the two planar parallel surfaces. In this way, the embedded electrode can provide directional stimulation, but in multiple directions, similar to embodiments where there may be top and bottom electrodes (e.g., in FIG. 24). In some embodiments, the degree of embeddedness can vary. For example, the exposed portion can include at least 25%, 50%, 75%, etc. of the partially embedded electrode.

As shown, the embedded electrode can be a circular helical coil (i.e., as if wrapped around a cylindrical object), however, other embodiments can have the embedded electrode be an elliptical helical coil (i.e., as if the object around which the wire was wrapped had an elliptical rather than circular cross-section). Yet other embodiments can have the embedded electrode be a solid electrode having a circular, elliptical, or rectangular cross-section. Some elliptical or rectangular embodiments can beneficially provide greater surface area while keeping the thickness of the coil (e.g., in the semimajor direction or in a thinner direction) at a minimum to reduce the overall thickness of the directional lead.

Some embodiments of partially embedded electrodes can include additional structural feature(s) to increase surface area beyond that provided by their cross-section. Examples of additional structural features can include conductive mesh. The conductive mesh may be formed by conductive wiring, a porous sheet of conductive material, and/or other conductive meshes electrically coupled to partially embedded electrode. These and/or other features of partially embedded electrodes may be configured to increase a surface area and/or current density of an electrode. For example, channels in partially embedded electrodes may expose more surface area, and/or create ridges, edges, and corners that increase current density, without increasing a size (e.g., the diameter) of an electrode. Implementations having such corners, hollow areas, conductive mesh, and/or scaffolding may function in a similar way.

Other embodiments of the partially embedded electrode can include an additional structural feature to increase current density beyond that provided by its cross-section and may also include a feature to increase current density at particular location(s). For example, as described above, ridges, edges, and corners may also have the effect of increasing current density due to charge accumulation. Other embodiments that may have increased surface area and/or current density can include electrodes with surfaces that have been treated by a sputtering process to create conductive microstructures or coatings that impart a texture to the electrode surface.

Figure 27:
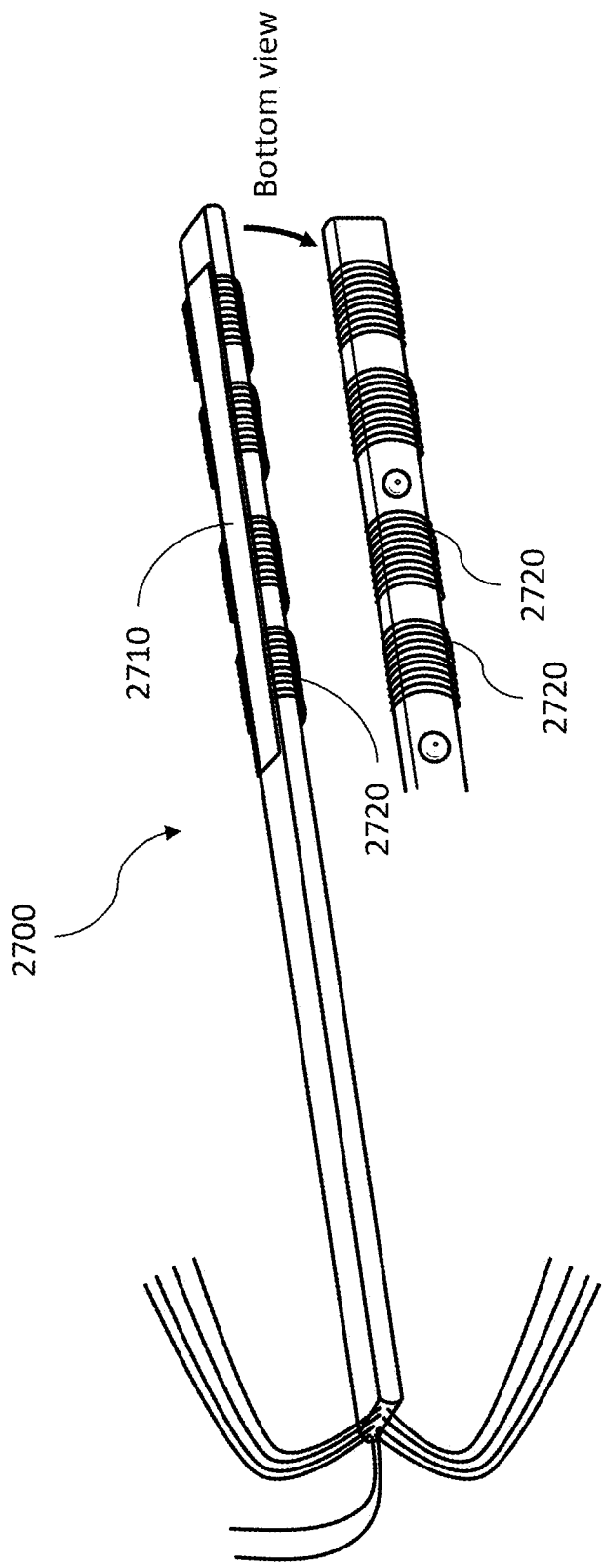
FIG. 27 is a diagram illustrating a simplified perspective view of an exemplary directional lead with masked circumferential defibrillation coil electrodes in accordance with certain aspects of the present disclosure.

FIG. 27 illustrates an embodiment of a lead 2700 including coil electrodes 2720 that are wrapped around the lead. As shown, the electrodes can be coils wrapped around a portion of the distal portion of a lead that has two parallel planar surfaces. As used herein, the term "wrapped" means that the conductor (e.g., wire) is wound in a somewhat helical manner around the lead. The wrapping may have deviations from being a perfect helix in that the wrapping may be looser in some places and tighter others, for example, to facilitate flexible portions of the lead or to avoid obstruction or contact of other elements such as other electrodes. It is contemplated that while most implementations involve winding a conductor around the lead, it is also possible that equivalent structures can be used such as hollow bands, connected plates, etc. that can provide substantially the same circumferential coverage.

To provide directional stimulation capability consistent with the present disclosure, as shown in FIG. 27, there may be an insulating mask 2710 over a portion of the coils(s) on one of the parallel planar surfaces. Such a mask can be, for example, an electrically insulating or absorbing material (e.g., rubber, plastic, etc.) to prevent or reduce the transmittal of electrical energy. Such masking can be continuous as shown or can be segmented to only cover one or more individual electrodes. The masks need not be on the same side of the directional lead. For example, some electrodes may be masked on the top side, and other electrodes may be masked on the bottom side, thereby providing options for directional stimulation. Similarly, some implementations can have masking on multiple sides. For example, masking could be applied to three of the four sides of the depicted directional lead thus exposing the portion of the electrode on only one side.

While the embodiments of FIGS. 24-27 depict specific numbers and disposition of electrodes, it is contemplated that various other arrangements and dispositions may be utilized, for example, 1, 2, 3, 5, etc. electrodes arranged with varying spaces, etc.

In accordance with certain disclosed embodiments, the present disclosure contemplates methods that include placing a lead having both defibrillation and cardiac pacing electrodes at an extravascular location within a patient. The extravascular location can be in a mediastinum of the patient, and specifically may be in a region of the cardiac notch or on or near the inner surface of a patient's intercostal muscle. As such, some placement methods can also include inserting the lead through an intercostal space associated with the cardiac notch of the patient.

Figure 28:
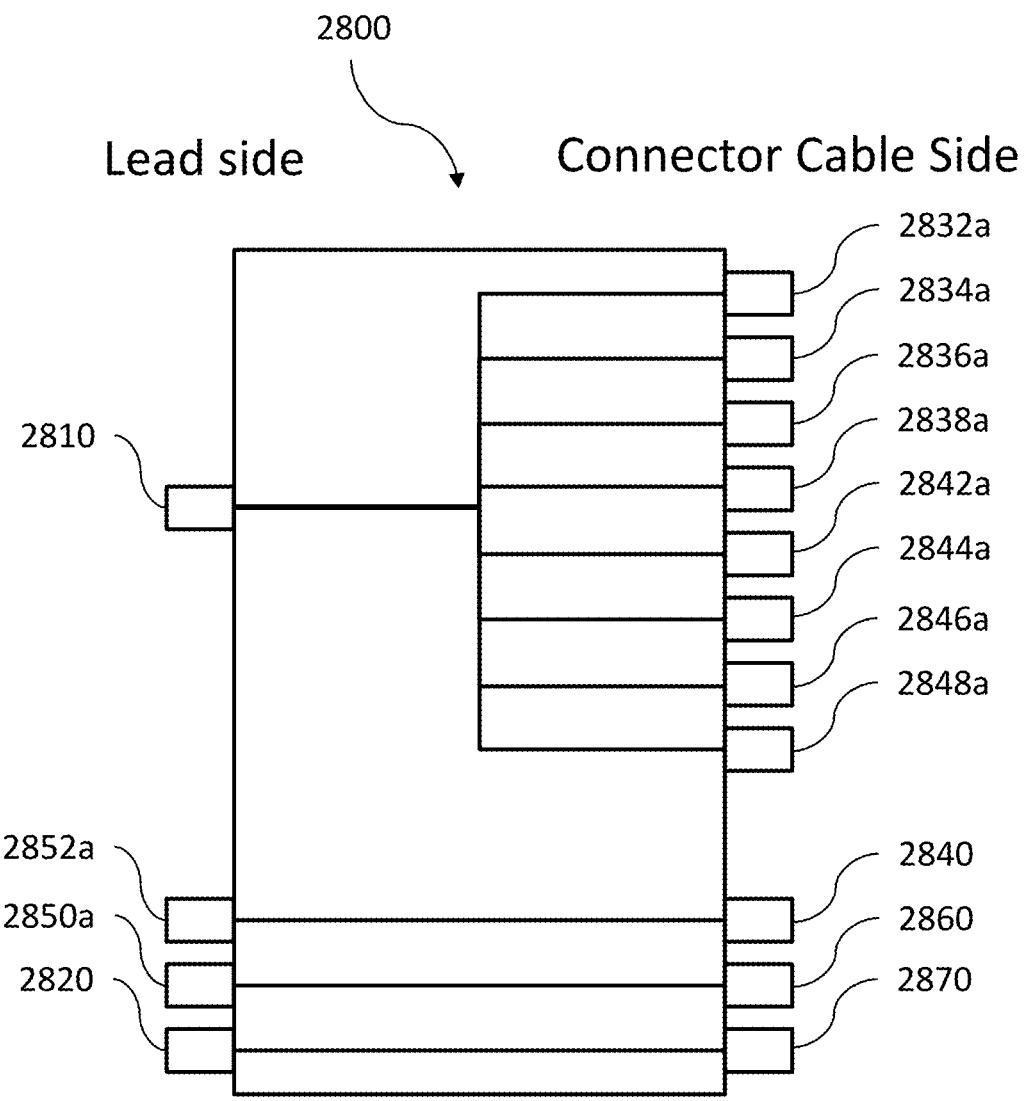
FIG. 28 is a diagram illustrating a simplified junction box in accordance with certain aspects of the present disclosure.

FIG. 28 depicts an exemplary junction box 2800 that can facilitate connections between the lead and its control and sensing systems. Such connections can be provided to provide pass through between the various pacing and defibrillation electrodes on the lead and the various input connections on the defibrillation source, one example being to an implantable ICD with a DF-4 connector. In the example implementation shown, the previously described leads can have corresponding junction box connections (2832a, 2834a, 2836a, 2838a, 2842a, 2844a, 2846a, 2848a) on the lead side of the junction box. The electrodes can be connected via a single lead 2810 (e.g., a multi-wire cable) at the connector cable side of the junction box. There can also be dedicated connections 2850a, 2852a for a pacing anode and cathode. The junction box can also have a lead side connection 2820 to the coil body itself (e.g., to a housing or grounding mesh) and corresponding SVC connection 2870. Cathode connection 2852a can be connected to a corresponding "tip" connection 2840. Anode connection 2850a can be connected to a corresponding "ring" connection 2860.

An exemplary method utilizing the leads described above is shown in the flowchart of FIG. 29. In implementations where defibrillation electrodes are disposed on different locations of a lead, as described above, defibrillation pulses will propagate in different directions. In such implementations, the electrodes can also provide sensing information allowing determination of which defibrillation electrodes are directed at the heart in a manner to optimize defibrillation. With such a determination, the defibrillation pulses can be delivered through the optimal electrodes.

One exemplary method can include, at 2910, receiving sensor data at a sensor (e.g., any disclosed electrode or other separate sensor), where the sensor data can be representative of electrical signals (e.g., from a heartbeat). At 2920, an algorithm can determine, based on the sensor data, an initial set of electrodes on a defibrillation lead including more than two defibrillation electrodes, from which to deliver a defibrillation pulse. The initial electrode set can be one estimated to be most directed toward the heart and thereby most appropriate for defibrillation (for example, based on determining relative strengths of the signals detected by different sensing electrodes). At 2930, a defibrillation pulse can be delivered with the initial set of electrodes. At 2940, post-delivery sensor data can be received, such as by the sensor(s) described above. At 2950, a determination can be made, based at least on the post-delivery sensor data whether the defibrillation pulse successfully defibrillated the patient. At 2960, if necessary, an updated set of electrodes which to deliver a subsequent defibrillation pulse can be determined, with the process optionally repeating starting at 2930 with the delivery of the subsequent defibrillation pulse.

In step 2950, the determination as to whether defibrillation was successful may include receiving signals representative of the current heart rhythm and comparing to an expected or desired heart rhythm that would be reflective of a successful defibrillation. In step 2960, determining a new set of electrodes may include, for example, switching to some electrodes on the opposite side of the lead. The determination may also result in using a different set of electrodes on the same side of the lead. In fact, any combination of defibrillation electrodes on the lead, or in combination with electrodes located off of the lead (for example, on the housing of an associated pulse generator) may be utilized, including reversing the electrical polarity of the defibrillation shock. The process of delivering defibrillation energy and selecting different electrode pairings can repeat, cycling through different combinations, until a successful defibrillation is detected. Again referring to step 2950, once a defibrillation configuration is determined that successfully defibrillates the heart, the system can retain that configuration so that it can be used for the first defibrillation delivery during a subsequent episode with the patient, thereby increasing the likelihood of successful defibrillation with the first delivered shock for future events.

Figures 30A, 30B:
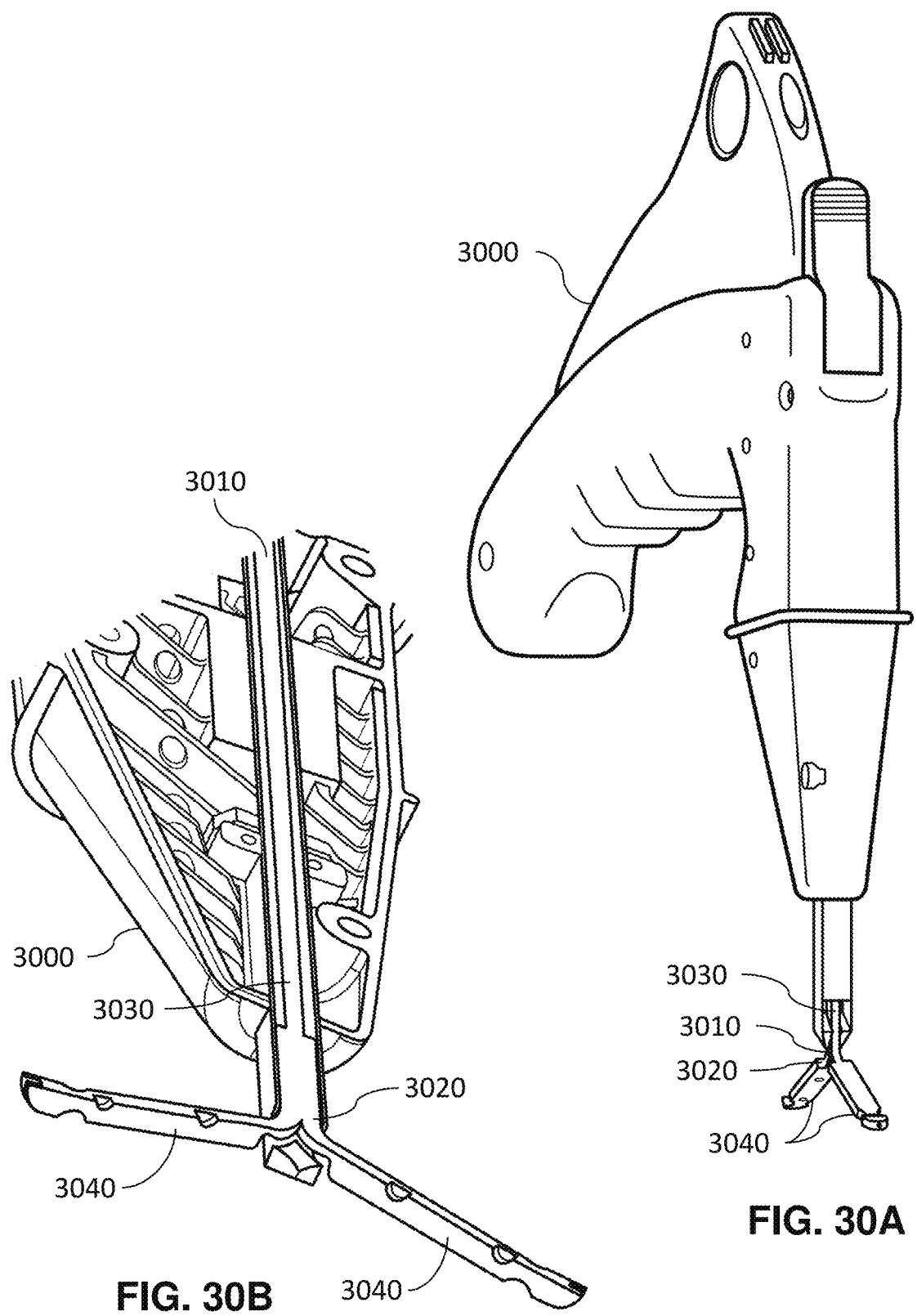
FIGS. 30A and 30B illustrate an exemplary splitting lead exiting a delivery system, in accordance with certain aspects of the present disclosure.

In another lead embodiment, depicted in FIGS. 30A and 30B, an electrical lead 3010 may be configured to have its distal portion split apart and travel in different directions during implantation in a patient. Such designs are referred to herein as "splitting leads." FIGS. 30A and 30B depicts one exemplary embodiment of a splitting lead.

Similar to other leads of the present disclosure, the splitting lead can have a distal portion 3020 having electrode(s) that are configured to generate therapeutic energy for biological tissue of the patient. The electrodes can include any combination of defibrillation electrodes and/or cardiac pacing electrodes. Also, as partially shown in FIG. 30B, the lead can have a proximal portion 3030 coupled to the distal portion and configured to engage a controller. The controller can be configured to cause the electrode(s) to generate the therapeutic energy, e.g., via transmitting current through wires to the various electrodes similar to other disclosed embodiments such as that of FIG. 24.

In the depicted embodiment, the distal portion is configured to split apart into sub-portions 3040 that travel in multiple directions during implantation into the patient. In this example, a delivery system 3000 is inserted into a patient (e.g., through an intercostal space in the region of the cardiac notch) and, after insertion, lead 3010 is advanced and sub-portions 3040 of the lead split off in different directions. While the example of FIGS. 30A and 30B depicts the lead splitting off in two different directions, the present disclosure contemplates designs following the teachings herein that split off in more directions (e.g., three directions, four directions, etc.).

The splitting lead designs disclosed herein may be particularly useful for ICD/defibrillation applications as they can provide for additional lead length and thus additional area for electrode surface. However, the present disclosure contemplates the use of splitting lead designs in pacing applications as well. In some applications, the splitting lead designs disclosed herein can include both pacing and defibrillation electrodes, as taught throughout this disclosure.

Figure 31A:
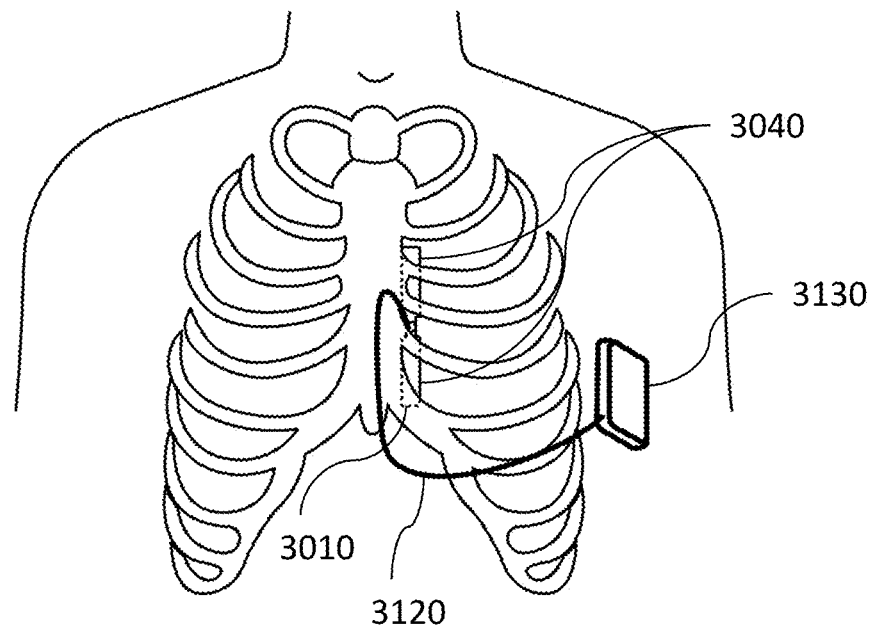
FIGS. 31A and 31B illustrate exemplary implantation locations/orientations for exemplary splitting leads, in accordance with certain aspects of the present disclosure.

FIG. 31A depicts an exemplary placement for a splitting lead 3010 in which a lead delivery system (or merely "delivery system") can be inserted into the patient, for example, through an intercostal space associated with or in the region of the cardiac notch of the patient. Exemplary methods of placing the splitting lead can include operating the delivery system to place the distal portion of the lead in an extravascular location of the patient. For example, the extravascular location can be in a mediastinum of the patient, in the region of the cardiac notch, and/or on or near the inner surface of an intercostal muscle. The lead's wires 3120 can extend to a controller 3130, which may be implanted in the patient.

After insertion, the delivery system 3000 can be operated such that lead 3010 can be advanced so that the distal portion of lead 3010 splits apart into two portions that travel in multiple directions within the patient. As shown in FIG. 31A, the distal portion of lead 3010 can split so that sub-portions 3040 travel in opposite directions parallel to a sternum of the patient.

Figure 31B:
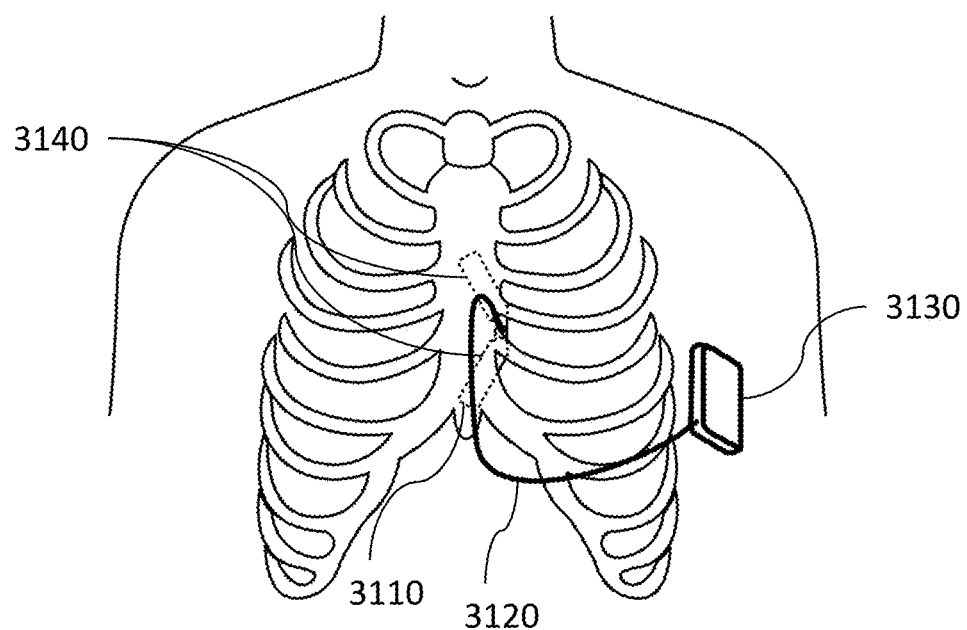

FIG. 31B depicts another exemplary placement for a splitting lead 3110 where the distal portion of the lead splits apart into two sub-portions 3140 that travel in directions approximately 100° apart and under the sternum of the patient. Additional extravascular placements are contemplated and can include the distal portion of the lead splitting into more sub-portions (e.g., the distal portion of the lead may split into three portions that travel in directions approximately 90° apart and parallel or perpendicular to the sternum of the patient.

Figure 32:
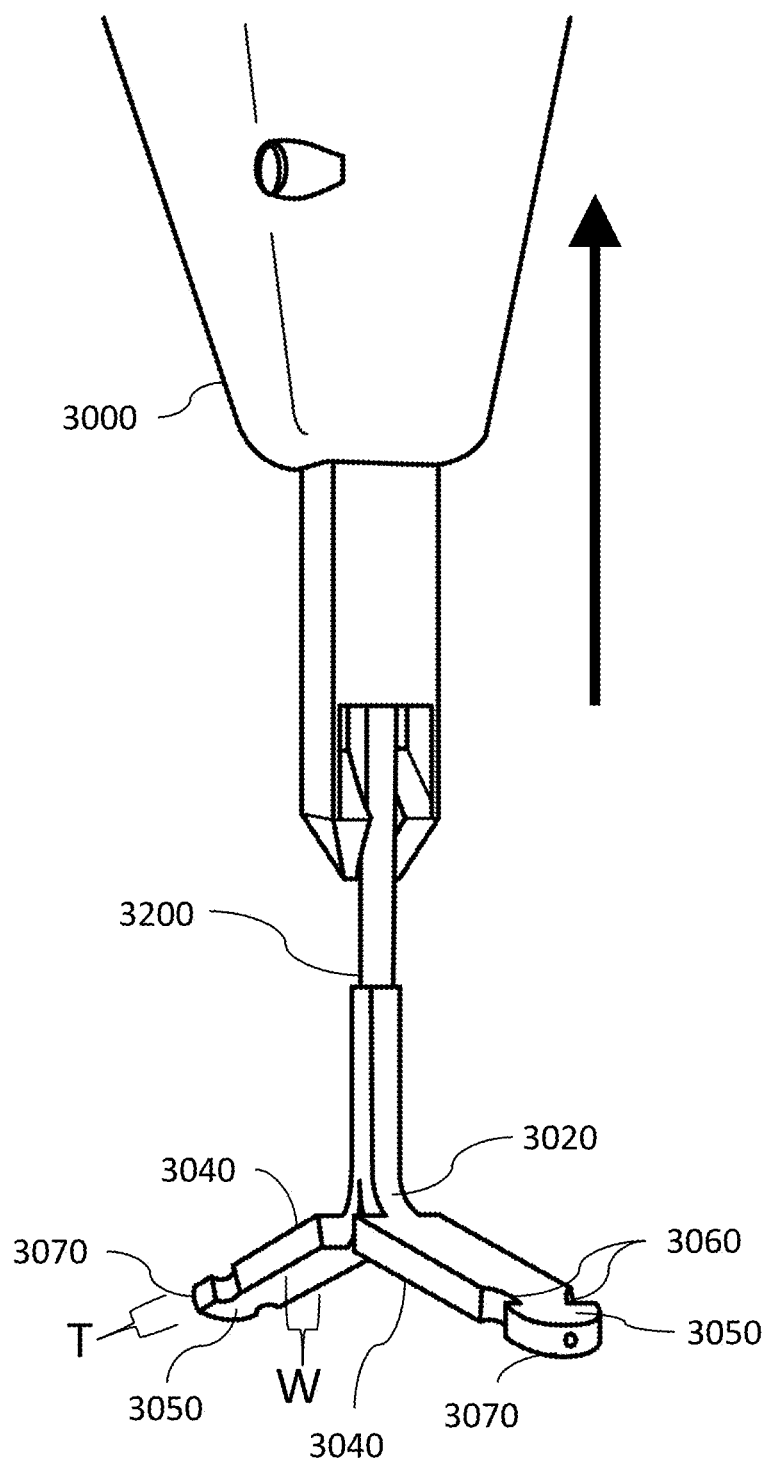
FIG. 32 illustrates an exemplary splitting lead exiting an exemplary delivery system, in accordance with certain aspects of the present disclosure.

FIG. 32 illustrates another view of an exemplary splitting lead, exiting an exemplary delivery system 3000. Such splitting leads can allow for increased total length and electrode surface area while facilitating implantation.

In one embodiment, the distal portion of the lead can be configured to split apart into two sub-portions having a combined length of approximately 6 cm (e.g., ±up to 1 cm). Numerous other lengths are contemplated, for example, approximately 4, 5, 7, 10, etc., centimeters. The two sub-portions can be of equal length or may have different lengths, for example, the distal portion can be configured to split apart into two sub-portions comprising 60% and 40% respectively of their total combined length. Other implementations can include those with approximately 55%/45%, 65%/35%, 70%/30%, etc., ratios of lengths and the ratios can be determined in order to provide optimal anatomical coverage given the implantation location.

Similar to the embodiments described with reference to FIG. 24, the sub-portions can include parallel planar surfaces. Similar to other embodiments, these sub-portions can then form rectangular prisms including the two parallel planar surfaces. As shown in FIG. 32, the distal portion can be wider (W) than it is thick (T).

During deployment, the lead is advanced through the tip of the delivery system (described further below). After placement of the lead in the patient, the delivery system can then be withdrawn (e.g., as indicated by the direction of the arrow in FIG. 32). To facilitate withdrawal of the delivery system after the lead has been implanted, the proximal portion of the lead can be configured to be thinner than the distal portion of the lead (see, e.g., location 3200 in FIG. 32, identifying the location where the proximal portion of the lead thins compared to the distal portion of the lead). In this manner, the lead can proceed directly through the tip of the delivery system 3000.

It is contemplated that each of the split distal portions of the splitting lead designs disclosed herein may incorporate features described above in conjunction with non-splitting lead designs.

For example, the sub-portions can include distal ends 3050 having flexible portions so as to allow the distal ends to change course when encountering sufficient resistance traveling through the biological tissue of the patient. For example, if the distal ends encounter bone, muscle, etc., the flexible portions can allow the distal ends to still deploy within the patient without necessarily affecting or damaging the resisting biological tissue. Such flexible portions can include a material that flexes more easily relative to material of other areas of the sub-portions. The material can be rubber, soft plastic, etc., which may be more flexible than the materials used for the rest of the sub-portions (e.g., metal, hard plastic, etc.). The flexible portions can include one or more cutouts 3060, which can be one or more areas having a reduced cross section compared to other areas of the sub-portions. In other embodiments, the flexible portions can be configured to cause the distal ends to be biased to change course in a particular direction. For example, such biasing can include using flexible materials having different flexibility in different portions, reinforcements such as rods that prevent flexing in certain directions, etc.

The particular shape of the distal ends can vary but, as shown in FIG. 32, the distal ends can be at least partially paddle shaped. In other embodiments, they may be more pointed to have a triangular or wedge shape or may be more rectangular to form a rectangular prism similar to the majority of the distal portion as shown.

Some embodiments of splitting leads can implement the use of shape memory material to enable deployment in a particular manner or in particular directions. For example, the sub-portions can include a shape memory material configured to bend in a predetermined direction when the sub-portions exit the delivery system. In this way, the delivery system can contain the sub-portions until they clear the internal structure of the delivery system and they will then deploy in their respective predetermined directions. Examples of such predetermined directions can result in creating an acute angle shape between the sub-portions and the proximal portion.

In some embodiments, the sub-portions can be further configured to move in a direction opposite the predetermined direction responsive to the shape memory material being heated to body temperature. For example, some implementations can benefit from having the lead held at a lower temperature for ease of loading into the delivery system and/or deployment. Once introduced into the body, after an appropriate length of time, the sub-portions would then heat to body temperature and as such would become deployed in a direction opposite the predetermined directions (e.g., toward the heart). In some implementations, movement in the direction opposite the predetermined direction can create a ninety degree shape, or an obtuse angle shape between the sub-portions and the proximal portion.

In some embodiments, for example, to assist in deployment through tissue that may provide resistance, the sub-portions of a splitting lead can include distal ends with distal tips 3070 that can be smaller than the distal ends (e.g., can be pointed or wedged-shaped, or have a ball shape, etc.). Some such implementations can also benefit by having distal tips configured to be more rigid compared to other portions of the distal end.

Figure 33:
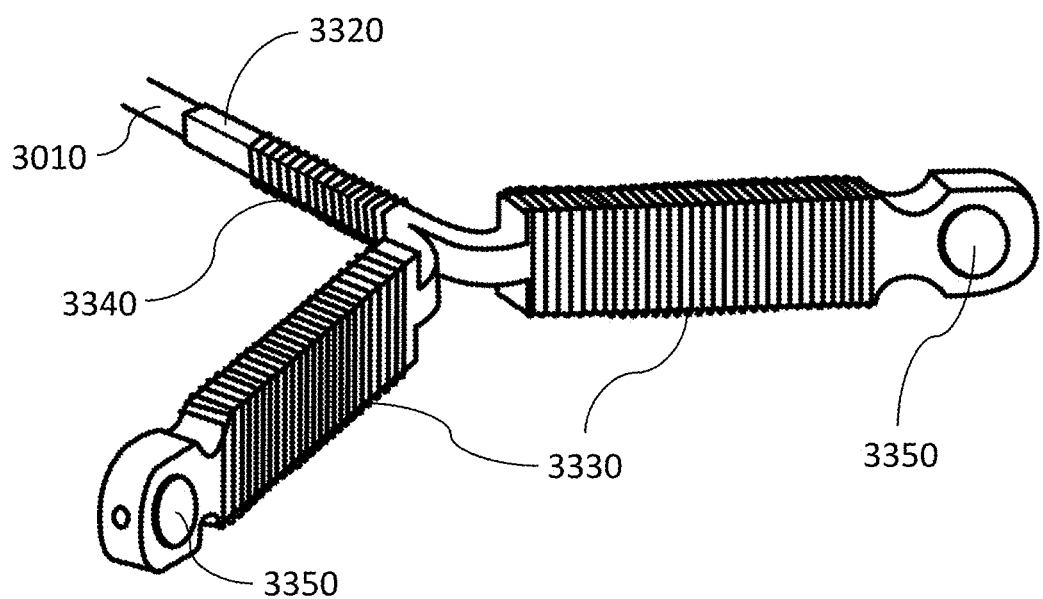
FIG. 33 illustrates an exemplary splitting lead with wrapped electrodes, in accordance with certain aspects of the present disclosure.

FIG. 33 illustrates an embodiment of a splitting lead that includes electrodes wrapped around the distal portion of the lead. A splitting lead 3010 may, for example, have electrodes 3330 wrapped around the sub-portions 3040 of the lead that travel in multiple directions during implantation. In an embodiment where the sub-portions are rectangular prisms, the one or more electrodes wrapped around the sub-portions may be elliptical in shape. When an electrode is wrapped in such a way, the present disclosure refers to its shape as elliptical, even though the wrapped electrode may not be purely oval in shape—since such electrodes are still somewhat oval and are longer in one dimension (e.g., width dimension of the sub-portion) than in another dimension (e.g., thickness dimension of the sub-portion). See FIG. 32 for examples of the width W and thickness T of a sub-portion.

In addition to electrodes being wrapped around the sub-portions 3040, electrode(s) may also be wrapped around a proximal part 3320 of the distal portion of the lead, specifically, the part of the distal portion that does not travel in different directions during implantation. Such wrapped electrodes 3340 can provide additional electrode surface area and may also be separately energized to deliver therapeutic energy along additional vectors. The present disclosure contemplates that such wrapped electrodes may be utilized for defibrillation and/or pacing.

The exemplary embodiment of FIG. 33 also depicts optional pacing electrodes 3350 located near the distal ends of the sub-portions. In other implementations, the pacing electrodes 3350 may not be as close to the distal ends as they are in FIG. 33 (i.e., they may not be on the "flexible" portions previously-described). In still other implementations, the pacing electrodes may be located on only one of the sub-portions, for example, if that particular sub-portion will be located within the patient at a better location with respect to the heart for pacing.

Figure 34:
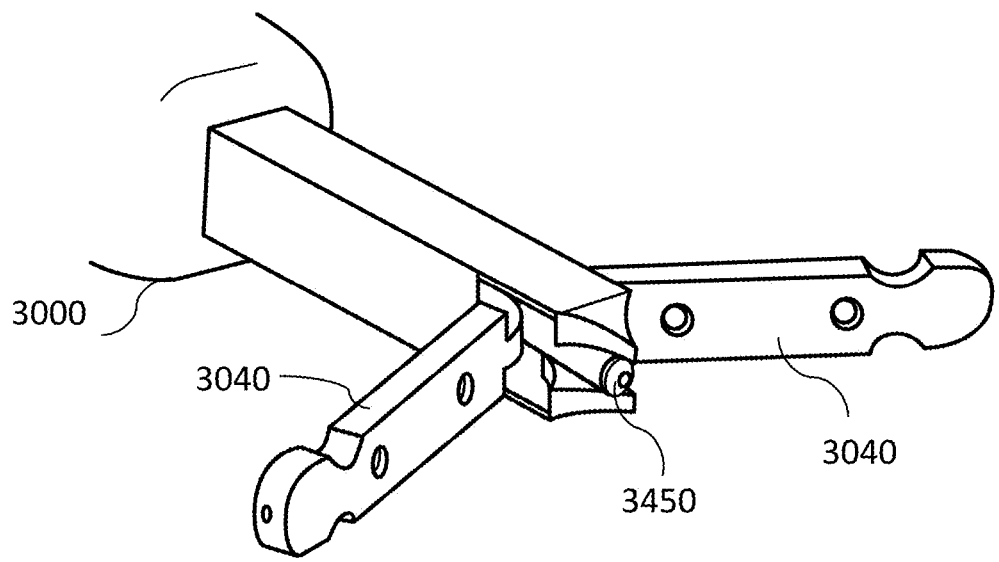
FIG. 34 illustrates an exemplary splitting lead with a pacing electrode extending between lead sub-portions, in accordance with certain aspects of the present disclosure.

FIG. 34 illustrates an embodiment of a splitting lead further including a central pacing electrode 3450 extending between the sub-portions 3040 that travel in multiple directions during implantation. This embodiment is similar to other splitting leads described herein and may also contain any of the features of such (e.g., wrapped electrodes, pacing electrodes on sub-portions, etc.). Central pacing electrode 3450 can be delivered via the delivery system 3000 as part of delivery of the splitting lead (which may include indentations in its sub-portions 3040 so that central pacing electrode 3450 better fits between the sub-portions 3040 when they fold together inside the delivery system). Central pacing electrode 3450 can extend and move along the main axis of the delivery system (e.g., straight down into the patient), and may be independently deployable and retractable/adjustable so the depth of the electrode tip can be independently set at the time of deployment. Consistent with discussions throughout the present disclosure, central pacing electrode 3450 may be used in conjunction with other electrodes and can provide additional vectors for the delivery of therapeutic energy.

Figure 35:
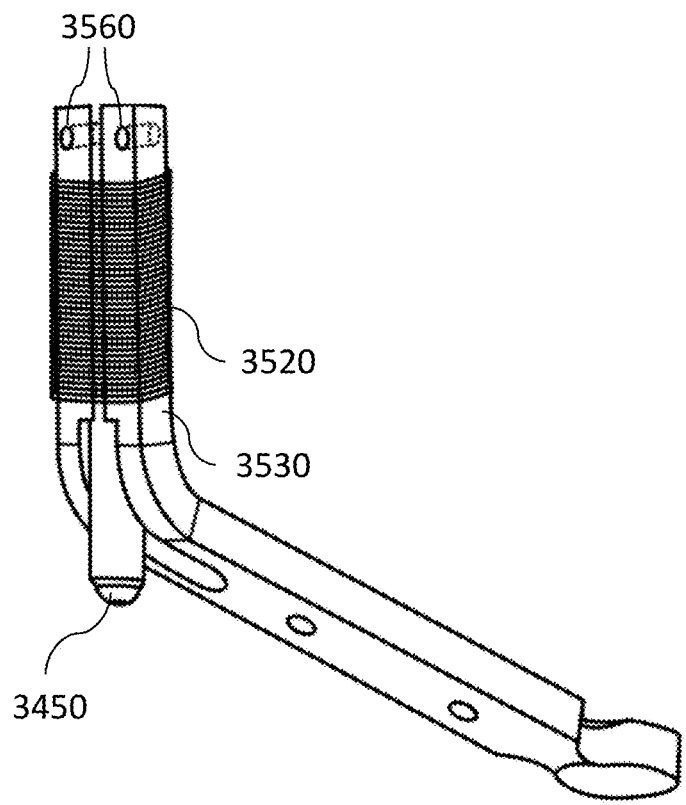
FIG. 35 illustrates a lead with exemplary suture holes and a pacing electrode extending from the lead, in accordance with certain aspects of the present disclosure.

FIG. 35 illustrates how this concept of a central pacing electrode 3450 can also be implemented with non-splitting lead designs such as those discussed above with respect to, for example, FIGS. 18, 19, etc.

FIG. 35 also illustrates how the concept of wrapped electrodes can be implemented with non-splitting lead designs. Specifically, electrode(s) 3520 may be wrapped around a proximal part 3530 of the distal portion of the lead, specifically, a part of the distal portion that does not travel in a different direction during implantation. Such wrapped electrode(s) 3520 can provide additional electrode surface area and may also be separately energized to deliver therapeutic energy along additional vectors. The present disclosure contemplates that such electrodes may be used for defibrillation and/or pacing.

FIG. 35 also depicts suture holes 3560 that may be located in a proximal part 3530 of the distal portion of the lead (i.e., the portion that does not travel in a different direction during implantation). A physician may tie sutures through a patient's tissues and suture holes 3560 in order to better fix the orientation of the distal portion of the lead at implantation. The sutures may be tied to intercostal muscle, skin, or any other portion of the patient suitable for securing the lead. While one exemplary configuration is depicted in FIG. 35, any number and/or combination of suture holes and suture hole locations can be included in any of the lead embodiments detailed throughout the present disclosure. For example, such suture holes may be utilized with splitting leads as well. Furthermore, rather than complete suture holes, one or more grooves or notches may be located on the proximal part 3530 of the distal portion of the lead. Such grooves or notches provide indentations that may aid in securing of the lead to the patient's tissue.

Figure 36:
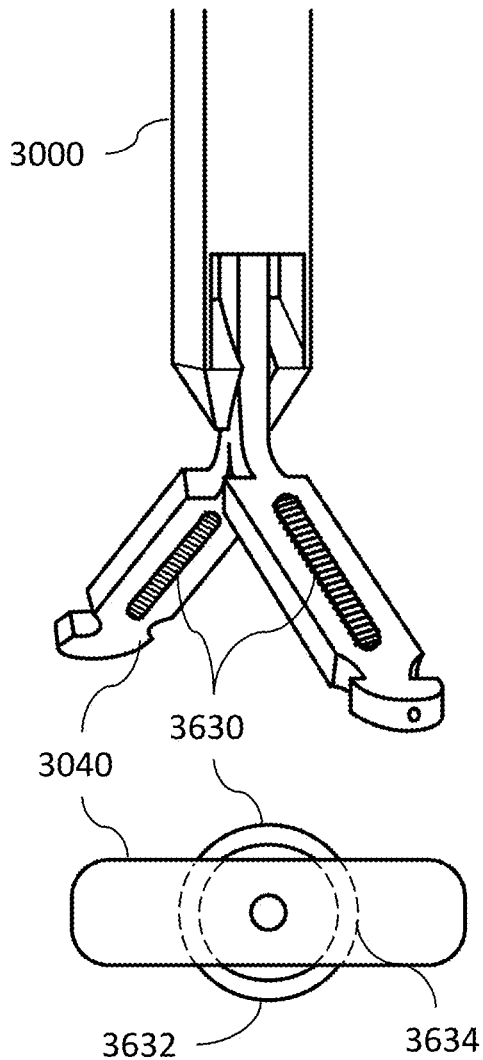
FIG. 36 illustrates an exemplary splitting lead with an embedded circular helical coil electrode, in accordance with certain aspects of the present disclosure.
Figure 37:
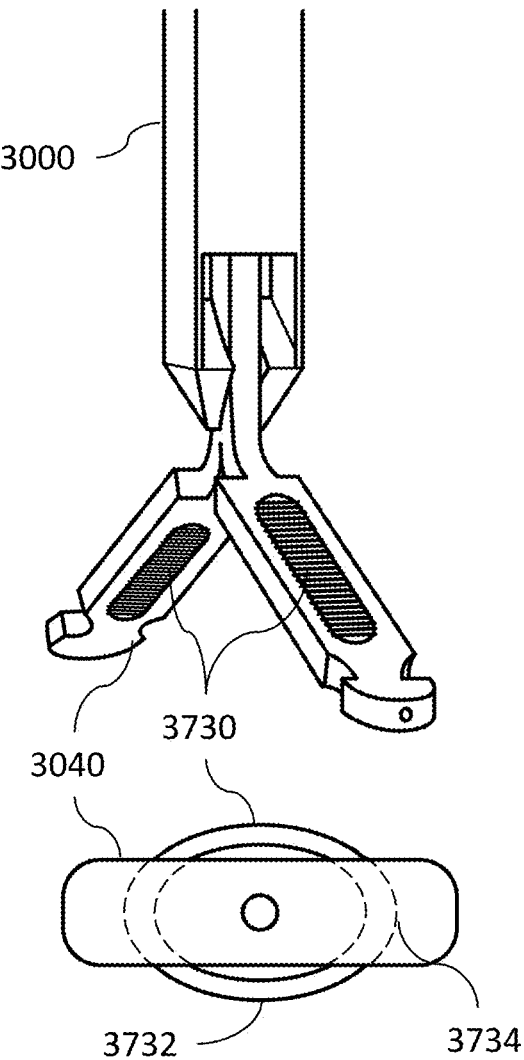
FIG. 37 illustrates an exemplary splitting lead with an embedded elliptical helical coil electrode, in accordance with certain aspects of the present disclosure.

FIGS. 36 and 37 illustrate embodiments of splitting leads that have embedded electrodes (see 3630 and 3730 respectively). Such splitting-lead embedded electrodes may include the features of any of the embedded electrodes previously described with regard to FIG. 26.

The FIGS. 36 and 37 embodiments depict helical coils that are oriented in the longitudinal direction (i.e., along the lengthwise direction of the sub-portion). FIG. 36 depicts an embedded electrode 3630 with a circular shaped helical coil (i.e., as if wrapped around a cylindrical object) while FIG. 37 depicts an embedded electrode 3730 with an elliptical shaped helical coil (i.e., as if wrapped around an object with an elliptical cross-section). Other embodiments could have the embedded electrode be a solid electrode having a circular, elliptical (e.g., oval), or rectangular cross-section. Some elliptical or rectangular embodiments can beneficially provide greater surface area while keeping the thickness of the coil (e.g., in the semimajor direction or in a thinner direction) at a minimum to reduce the overall thickness of the directional lead.

As shown in the embodiments of FIGS. 36 and 37, the electrodes can be partially embedded in the sub-portions 3040 that travel in multiple directions during implantation. Similar to earlier embodiments, these partially embedded electrodes have an embedded portion 3634/3734 and an exposed portion 3632/3732. In the specific examples of FIGS. 36 and 37, the splitting leads have sub-portions that each comprise two parallel planar surfaces and the exposed portions of the embedded electrodes are on both of the planar parallel surfaces.

Simplified end views of the splitting lead sub-portions are shown in the insets of FIGS. 36 and 37, detailing parts of the embedded electrodes that are exposed, and parts that are embedded. As can be seen, the portion of the embedded electrodes that is exposed can have a similar surface area to the previously described electrodes. For example, the exposed portions can include at least 25%, 50%, 75%, etc., of the partially embedded electrode.

These embedded electrodes (also referred to herein equivalently as "partially embedded electrodes") can include additional structural features for increasing surface area and/or current density as described above with reference to FIG. 26. Also, when referring herein to "embedded" electrodes, it is contemplated that some implementations may have a small amount of material between the conductive electrode and the patient that does not significantly reduce therapeutic energy and thus the "exposed" portion is still considered exposed. For example, there may be a thin layer of protective coating or the like between the electrode and the patient's tissue but this thin layer may cause no significant interference with the therapeutic energy provided via the embedded electrode.

FIGS. 38 and 39 illustrate embodiments of embedded electrodes that are exposed only on only one side of the sub-portions. Such embedded electrodes will provide more directional stimulation, as discussed above. In the particular cross-sections of the depicted embodiments, the electrodes are helical coils and have an exposed portion on only one of two planar parallel surfaces.

FIG. 38 also illustrates that there may be multiple embedded electrodes 3830 on a single sub-portion 3040. FIG. 38 is similar to FIG. 36 but instead of one long embedded electrode, there are two shorter embedded electrodes that may be generally inline with each other (though some offset could be present in certain implementations). The embodiment of FIG. 39 provides an alternative design where two embedded electrodes 3930 are positioned side-by-side (e.g., parallel) on the same sub-portion 3040. Such designs can be beneficial in that the splitting of embedded electrodes into sections can provide for a greater number of vectors or can provide for alternative electrode surface areas and current densities. In other embodiments, there may be any number of electrodes besides two (e.g., three, four, five, etc.).

The particular embodiment depicted in FIG. 38 may employ electrodes 3830 for defibrillation and electrodes 3850 for pacing, although it is contemplated that each of the electrodes could be configured to be used for pacing and/or defibrillation. While not shown due to the perspective view, similar electrodes configurations can be utilized on both sub-portions. Moreover, other combinations of defibrillation and pacing electrodes, as discussed throughout this disclosure, may be chosen for the splitting leads.

Figure 40A:
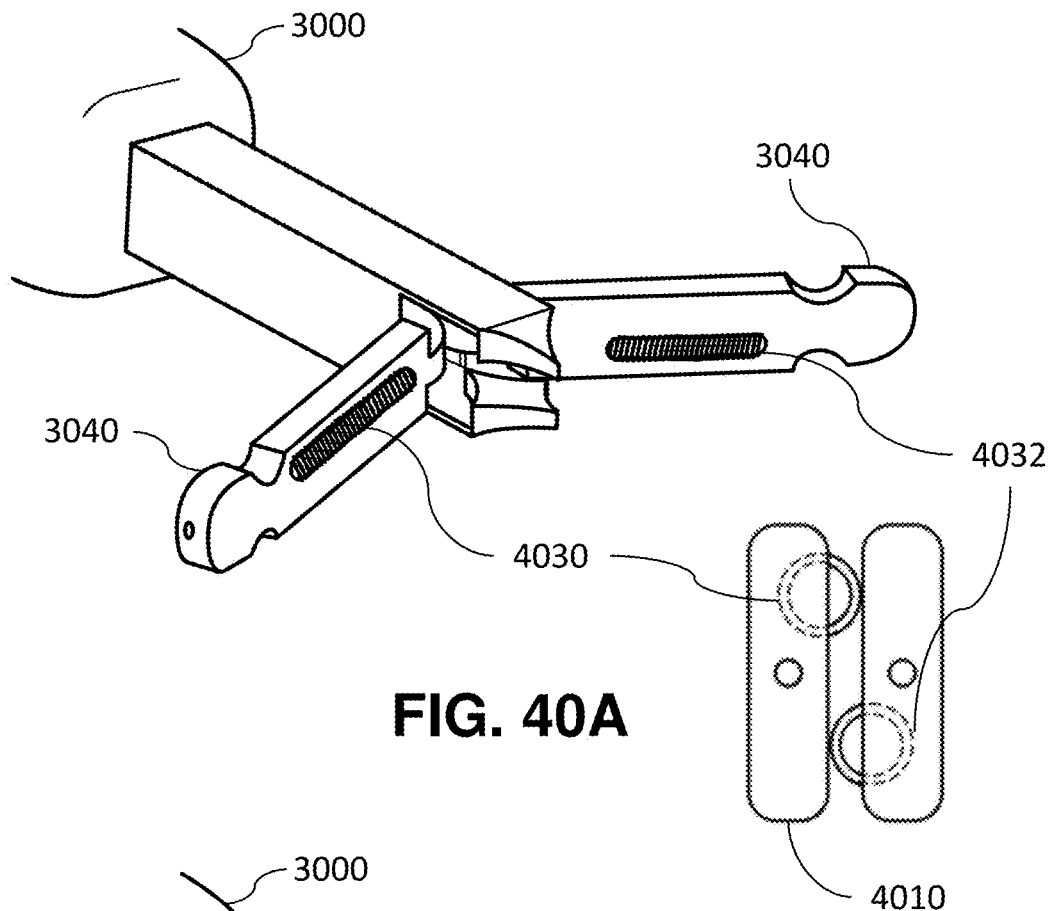
FIG. 40A illustrates an exemplary splitting lead with offset embedded electrodes, in accordance with certain aspects of the present disclosure.
Figure 40B:
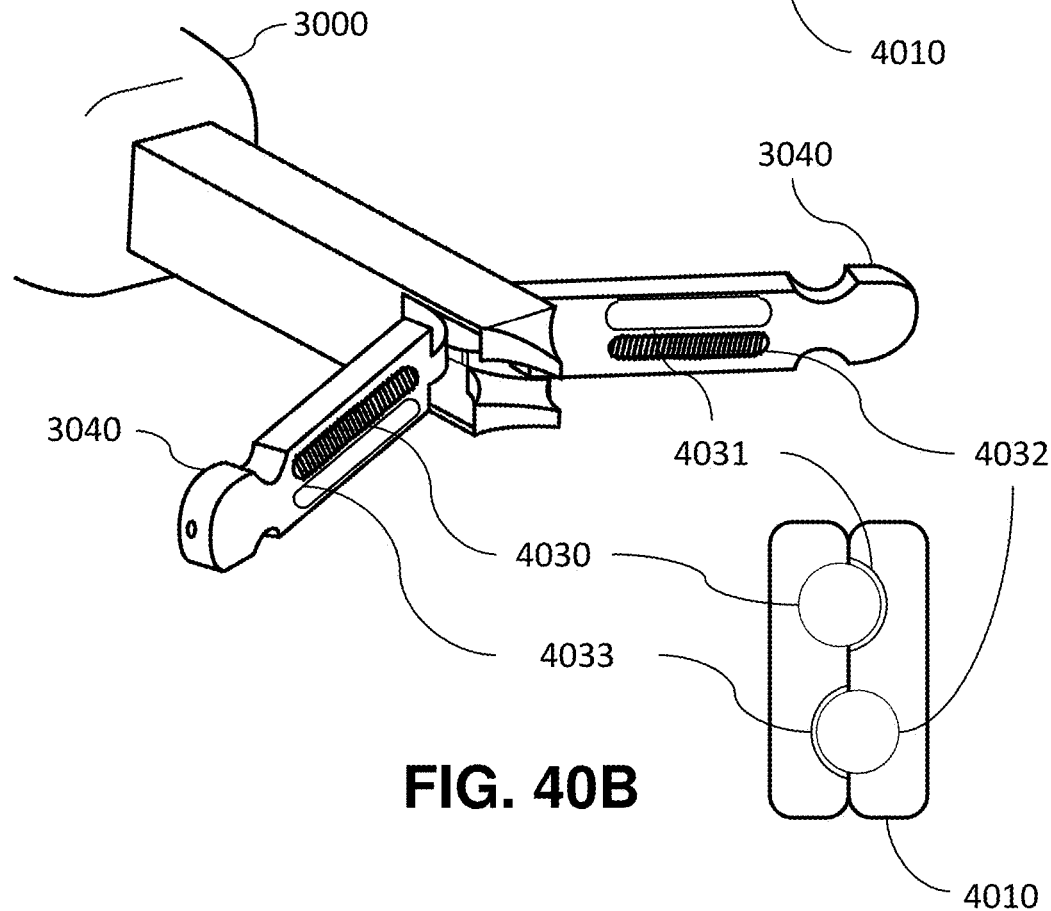
FIG. 40B illustrates an exemplary splitting lead with offset embedded electrodes that fit into opposing concavities, in accordance with certain aspects of the present disclosure.

FIG. 40A illustrates an embodiment of a lead having offset electrodes 4030 and 4032. This embodiment is similar to that shown in FIG. 39 but rather than having two embedded electrodes on each sub-portion 3040 there is one embedded electrode on each sub-portion and the exposed portions of the partially embedded electrodes are offset in order to avoid interference (e.g., contact) when the distal portion of the electrical lead is folded (i.e., before it splits apart into sub-portions that travel in multiple directions during implantation). A simplified view of a folded lead 4010 is depicted by the inset illustrating how such a lead has a smaller form factor than would be possible without such an offset. Additionally, as shown in FIG. 40B, sub-portions 3040 may include concavities 4031 and 4033 equally opposing the shapes of exposed electrodes 4030 and 4032. As shown by the inset section view, when the distal portion of the lead is folded, the exposed portions of the electrodes fit within the concavities of the opposing sub-portion, thereby creating an even smaller form factor when folded. As with other embodiments, the partially embedded electrodes can include pacing electrodes and/or defibrillation electrodes, as well as optionally having a pacing electrode extend between the sub-portions that travel in multiple directions during implantation.

FIGS. 41A, 41B, and 41C illustrate portions of a delivery system deploying a component. The delivery system (for example, the delivery system 200 in FIGS. 9A-D or delivery system 3000 in FIG. 30A) can include a component advancer configured to advance the component into the patient. The delivery system can also include a handle configured to be actuated by an operator. The component advancer can be coupled to the handle and thereby configured to advance the component into the patient by applying a force to a portion of the component in response to actuation of the handle by the operator. Also, the component advancer can be configured to removably engage a portion of the component to deliver the component into the patient.

As depicted in the delivery system of FIG. 30A, the component can be a splitting lead 3010 having a proximal portion 3030 configured to engage a controller and a distal portion 3020 configured to split apart into sub-portions 3040 that travel in multiple directions during implantation into a patient. To facilitate the deployment of such a splitting lead, the delivery system can include, as shown in FIG. 41A, an insertion tip 4110 having a first ramp 4120 configured to facilitate advancement of a first sub-portion into the patient in a first direction. There can be a similar second ramp 4130 (shown in the cross-section view of the tip at the top of FIG. 41A) configured to facilitate advancement of a second sub-portion into the patient in a second direction.

As depicted in FIG. 41A, the first direction (i.e., the direction in which the first ramp advances the first sub-portion of the lead) can be opposite the second direction (i.e., the direction in which the second ramp advances the second sub-portion of the lead). In other words, the first direction can be 180° from the second direction. This directional split is also depicted in FIG. 31A.

In other embodiments, the angle between the first direction and second direction can be approximately 100°, allowing for placement of the sub-portions at least partially under the sternum. This directional split is also depicted in FIG. 31B. Other angles between the first direction and second direction (and their associated ramp configurations) are contemplated, for example, 90°, 110°, 120°, etc.

In some implementations, the delivery system can include a third ramp (e.g., in addition to the first and second ramps) configured to facilitate advancement of a third sub-portion into the patient in a third direction (e.g., 90° from the first and second directions). This can permit deployment of sub-portions approximately 90° apart and either parallel or perpendicular to the sternum of the patient.

In other implementations, at least the first ramp, and optionally the second ramp, may include a gap 4140 configured to facilitate removal of the delivery system after implantation of the splitting lead. An example of how gap 4140 can facilitate removal of the delivery system is depicted in the deployment sequence of FIGS. 41A, 41B, and 41C. The component (here a splitting lead) is shown in FIG. 41A having the sub-portions of the splitting lead engaging the first ramp and the second ramp to split apart in multiple directions. FIG. 41B then depicts a later stage in delivery showing the gap being wide enough to pass the proximal portion 3030 of the splitting lead, but still thinner than the width of the sub-portions of the splitting lead, which must engage the ramps in order to split off in different directions. Once the sub-portions have split apart such that they no longer engage the ramps, the delivery system can begin to withdraw over the proximal portion of the lead. FIG. 41C depicts the delivery system further withdrawn and the proximal portion 3030 of the lead being further exposed.

In another implementation, instead of the first and second ramps being at the same lengthwise position in the insertion tip (i.e., back, to back) the second ramp may be located at a more distal location than the first ramp so that advancement of the second sub-portion will be at a location deeper into the patient.

In some embodiments, the ramps may additionally include a taper at their proximal ends to widen the gap in that location. This widening can facilitate advancement of the component through the insertion tip by reducing the likelihood of the component getting stuck inside the gap.

To facilitate insertion of the delivery tool into patient tissue, the insertion tip may include a tissue-separating component 4150. As shown in FIGS. 41A, 41B, and 41C, the tissue-separating component can be wedge-shaped to separate and/or cut through tissue as needed for insertion. The tissue-separating component may also have a blunted distal end to reduce or avoid damage to tissue, blood vessels, etc. In the same manner as discussed above with regard to the ramps, the tissue-spreading component can include a gap configured to facilitate removal of the delivery system after implantation of the splitting lead.

Some embodiments of the insertion tip can include a movable cover configured to cover the gap during implantation. The movable cover can be configured to prevent tissue from accumulating in the gap when the insertion tip is pushed through patient tissue. Such movable covers can include, for example, a cover that can be pulled off when proper insertion depth is reached. In other examples, the cover can include a pivot, hinge, or flap to allow the movable cover to swivel out of the way of the component.

As depicted in FIG. 41D, other embodiments may incorporate a gap-filling component 4040 on the distal end of the splitting lead to fill the gap between the tissue-separating components. Gap-filling components 4040 may be incorporated on the distal ends of sub-portions 3040 such that, when the splitting lead is folded and loaded into the delivery system, the gap-filling components fit within and fill the gap of the tissue-separating component. Once inserted within the patient tissue, the gap-filling components are deployed with sub-sections 3040, as described previously with regard to FIG. 41A, thereby clearing the gap and allowing for proximal portion 3030 to travel through the gap, as shown in FIGS. 41B and 41C.

As described above, in some implementations, system 200 (FIG. 3) includes the electrical lead 1600 (FIG. 16), handle 300 (FIG. 3), component advancer 302 (FIG. 3), first and second insertion tips 304, 306 (FIG. 3), and/or other components. First insertion tip 304 and second insertion tip 306 may be configured to close around a distal tip of the electrical lead when the electrical lead is placed within component advancer 302. First insertion tip 304 and second insertion tip 306 may be configured to push through biological tissue when in a closed position and to open to enable the electrical lead to exit from component advancer 302 into the patient. Component advancer 302, first insertion tip 304, and second insertion tip 306 may be configured to maintain the electrical lead in a particular orientation during the exit of the component from component advancer 302 into the patient. Also as described above, first insertion tip 304 may include a ramped portion configured to facilitate advancement of the component into the patient in a particular direction, and/or the electrical lead may be configured to bend in a predetermined direction after the exit of the component from the component advancer (e.g., because of its shape memory properties, etc.).

Figure 42:
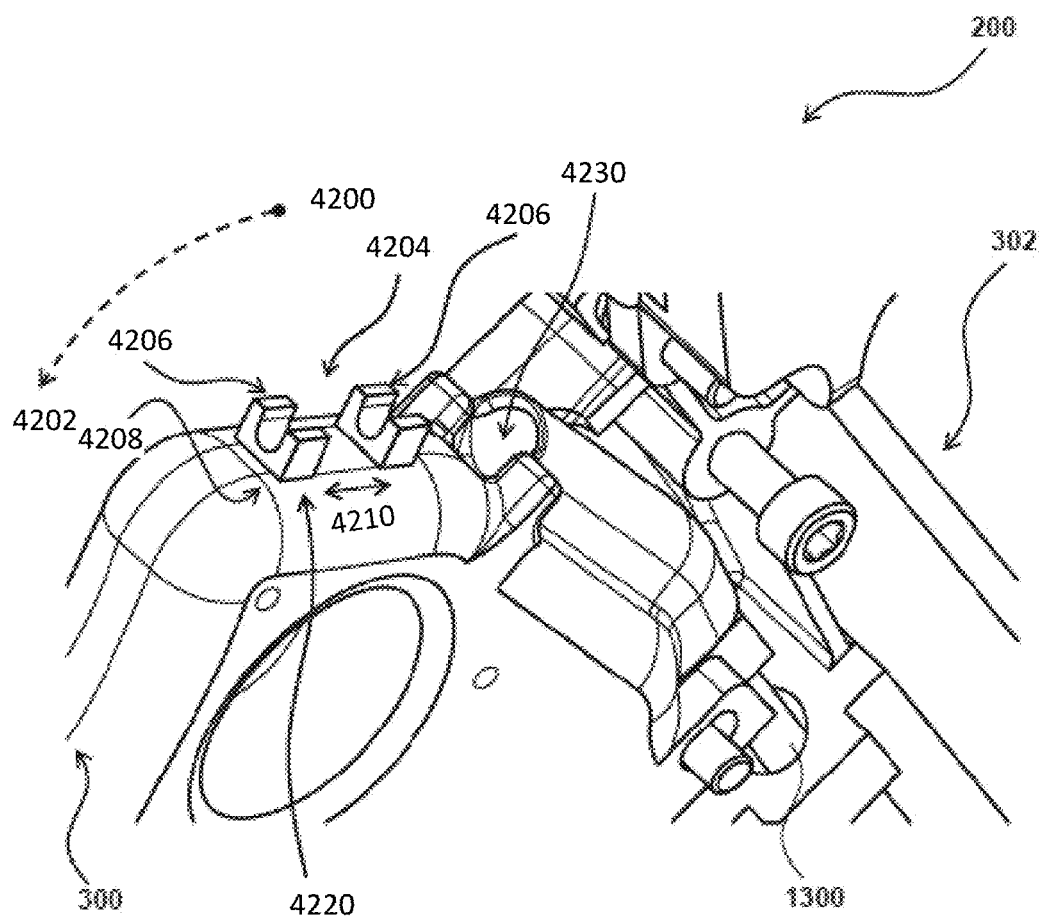
FIG. 42 illustrates exemplary components of a delivery system configured to load (or reload) a component (e.g., an electrical lead) into the delivery system, in accordance with certain aspects of the disclosure; and, FIG. 43 illustrates an example of an alignment block coupled to a proximal portion of an electrical lead, in accordance with certain aspects of the disclosure.

FIG. 42 illustrates components of delivery system 200 configured to load (or reload) a component (e.g., an electrical lead 1600 shown in FIG. 16) into delivery system 200. In some implementations, to facilitate reloading delivery system 200, an operator may thread proximal portion 1606 (FIG. 16) of lead 1600 backwards through insertion tips 304, 306 (FIG. 3), through pusher tube 1300 (in an implementation shown in FIG. 13) and out through an opening 4230 in handle 300. In some implementations, component advancer 302 may be configured to reload a component (e.g., an electrical lead) into delivery system 200. In such implementations, handle 300 may be configured to move from an advanced position 4200 to a retracted position 4202 to facilitate the reload of the component (e.g., the electrical lead).

In some implementations, handle 300 may include a dock 4204 configured to engage an alignment block coupled with the component (e.g., electrical lead) such that, responsive to handle 300 moving from advanced position 4200 to retracted position 4202, the engagement between dock 4204 and the alignment block draws the component into delivery system 200 to reload delivery system 200. As a non-limiting example using the implementation of component advancer 302 shown in FIG. 13-14, once the alignment block and electrical lead are properly seated within dock 4204, handle 300 may be re-cocked (e.g., moved from position 4200 to position 4202), which draws distal portion 1602 of electrical lead 1600 into delivery system 200 and closes insertion tips 304, 306 (FIG. 3).

In some implementations, dock 4204 may comprise one or more alignment and/or locking protrusions 4206 (the example in FIG. 42 illustrates two protrusions 4206) located on a portion 4208 of handle 300 toward component advancer 302. Locking protrusions 4206 may have a "U" shaped channel configured to receive a wire portion (e.g., part of proximal portion 1606) of an electrical lead 1600 (FIG. 16). Locking protrusions 4206 may have a spacing 4210 that corresponds to a size of an alignment block on the wire portion of electrical lead 1600 and allows the alignment block to fit between locking protrusions 4206 (with the wire portions resting in the "U" shaped channels of locking protrusions 4206).

Figure 43:
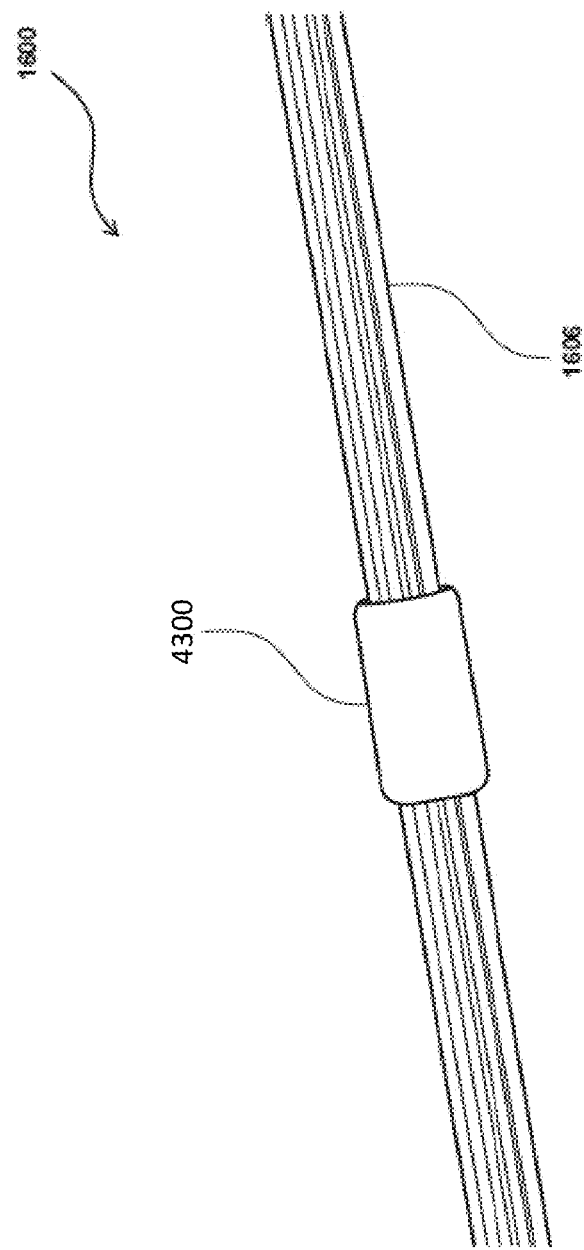

FIG. 43 illustrates an example of an alignment block 4300 coupled to proximal portion 1606 of an electrical lead 1600. Alignment block 4300 may have a cylindrical shape, for example, with a length matching spacing 4210 configured to fit between locking protrusions 4206 shown in FIG. 42.

Returning to FIG. 42, in some implementations, handle 300 may include an alignment surface 4220 configured to receive the proximal portion 1606 (FIG. 43) of electrical lead 1600 (FIG. 16) such that, responsive to handle 300 moving from the advanced position to the retracted position, the component is drawn into delivery system 200 to reload delivery system 200. In some implementations, alignment surface 4220 may be the same as surface 4208, but without locking protrusions 4206. In some implementations, an operator may hold proximal portion 1606 against alignment surface 4220, within a retention block 4206, with finger pressure while handle 300 moves from advanced position 4200 to retracted position 4202, for example. In some implementations, the alignment block 4300 may not be utilized.

In the following, further features, characteristics, and exemplary technical solutions of the present disclosure will be described in terms of items that may be optionally claimed in any combination:

Item 1: An electrical lead for implantation in a patient, the lead comprising: a distal portion comprising one or more electrodes that are configured to generate therapeutic energy for biological tissue of the patient; and a proximal portion coupled to the distal portion and configured to engage a controller, the controller configured to cause the one or more electrodes to generate the therapeutic energy, wherein at least a portion of the distal portion of the lead comprises two parallel planar surfaces that include the one or more electrodes.

Item 2: The electrical lead of Item 1, wherein the two parallel planar surfaces comprise a rectangular prism and the one or more electrodes comprise defibrillation electrodes or cardiac pacing electrodes.

Item 3: The electrical lead of any one of the preceding Items, wherein the one or more electrodes comprise both defibrillation electrodes and cardiac pacing electrodes.

Item 4: The electrical lead of any one of the preceding Items, wherein the distal portion is configured for extravascular implantation and wherein the one or more electrodes comprise both defibrillation electrodes and cardiac pacing electrodes.

Item 5: The electrical lead of any one of the preceding Items, wherein one or more electrodes comprise thin metallic plates.

Item 6: The electrical lead of any one of the preceding Items, wherein the thin metallic plates are rectangular.

Item 7: The electrical lead of any one of the preceding Items, wherein the thin metallic plates are elliptical.

Item 8: The electrical lead of any one of the preceding Items, wherein the thin metallic plates are on both of the two parallel planar surfaces.

Item 9: The electrical lead of any one of the preceding Items, wherein one or more electrodes comprise coil(s) wrapped around the portion of the distal portion of the lead comprising two parallel planar surfaces.

Item 10: The electrical lead of any one of the preceding Items, further comprising an electrically insulating mask over a portion of the coil(s) on one of the parallel planar surfaces.

Item 11: The electrical lead of any one of the preceding Items, wherein at least one electrode is partially embedded in the portion of the distal portion of the lead comprising two planar parallel surfaces, and the partially embedded electrode has an embedded portion and an exposed portion.

Item 12: The electrical lead of any one of the preceding Items, wherein the exposed portion is on both of the two planar parallel surfaces.

Item 13: The electrical lead of any one of the preceding Items, wherein the exposed portion is on only one of the two planar parallel surfaces.

Item 14: The electrical lead of any one of the preceding Items, wherein the exposed portion comprises at least 50% of a perimeter of the partially embedded electrode.

Item 15: The electrical lead of any one of the preceding Items, wherein the partially embedded electrode is a circular helical coil.

Item 16: The electrical lead of any one of the preceding Items, wherein the partially embedded electrode is an elliptical helical coil.

Item 17: The electrical lead of any one of the preceding Items, wherein the partially embedded electrode is a solid electrode having a circular, elliptical, or rectangular cross section.

Item 18: The electrical lead of any one of the preceding Items, wherein the partially embedded electrode includes an additional structural feature to increase surface area beyond that provided by its cross-section.

Item 19: The electrical lead of any one of the preceding Items, wherein the partially embedded electrode includes an additional structural feature to increase current density beyond that provided by its cross-section.

Item 20: The electrical lead of any one of the preceding Items, wherein the partially embedded electrode comprises a feature to increase current density at particular location(s).

Item 21: A method comprising: placing a lead comprising both defibrillation and cardiac pacing electrodes at an extravascular location within a patient.

Item 22: The method of any one of the preceding Items, wherein the extravascular location is in a mediastinum of the patient.

Item 23: The method of any one of the preceding Items, wherein the extravascular location is in a region of a cardiac notch.

Item 24: The method of any one of the preceding Items, wherein the extravascular location is on or near the inner surface of an intercostal muscle.

Item 25: The method of any one of the preceding Items, wherein the placing further comprises inserting the lead through an intercostal space associated with the cardiac notch of a patient.

Item 26: A computer program product comprising a non-transitory, machine-readable medium storing instructions which, when executed by at least one programmable processor, cause the at least one programmable processor to perform operations comprising: receiving sensor data; determining, based at least on the sensor data, an initial set of electrodes on a defibrillation lead including more than two defibrillation electrodes, from which to deliver a defibrillation pulse; delivering the defibrillation pulse with the initial set of electrodes; receiving post-delivery sensor data; determining, based at least on the post-delivery sensor data whether the defibrillation pulse successfully defibrillated the patient; and if necessary, determining an updated set of electrodes from which to deliver a subsequent defibrillation pulse.

Item 27: An electrical lead for implantation in a patient, the lead comprising: a distal portion comprising one or more electrodes that are configured to generate therapeutic energy for biological tissue of the patient; and a proximal portion coupled to the distal portion and configured to engage a controller, the controller configured to cause the one or more electrodes to generate the therapeutic energy, wherein the distal portion is configured to split apart into sub-portions that travel in multiple directions during implantation into the patient.

Item 28: The electrical lead of any one of the preceding Items, wherein the one or more electrodes comprise defibrillation electrodes and/or cardiac pacing electrodes.

Item 29: The electrical lead of any one of the preceding Items, wherein the distal portion is configured to split apart into two sub-portions having a combined length of approximately 6 cm.

Item 30: The electrical lead of any one of the preceding Items, wherein the distal portion is configured to split apart into two sub-portions of equal length.

Item 31: The electrical lead of any one of the preceding Items, wherein the distal portion is configured to split apart into two sub-portions having different lengths.

Item 32: The electrical lead of any one of the preceding Items, wherein the distal portion is configured to split apart into two sub-portions comprising 60% and 40% respectively of their total combined length.

Item 33: The electrical lead of any one of the preceding Items, wherein the sub-portions comprise parallel planar surfaces.

Item 34: The electrical lead of any one of the preceding Items, wherein the sub-portions comprise rectangular prisms including two parallel planar surfaces.

Item 35: The electrical lead of any one of the preceding Items, wherein the distal portion is wider than it is thick and the proximal portion is configured to be thinner than the distal portion in a manner that facilitates removal from a delivery system.

Item 36: The electrical lead of any one of the preceding Items, wherein the sub-portions include distal ends and the distal ends include flexible portions so as to allow the distal ends to change course when encountering sufficient resistance traveling through the biological tissue of the patient.

Item 37: The electrical lead of any one of the preceding Items, wherein the flexible portions comprise a material that flexes more easily relative to material of other areas of the sub-portions.

Item 38: The electrical lead of any one of the preceding Items, wherein the flexible portions comprise one or more cutouts, the one or more cutouts comprising one or more areas having a reduced cross section compared to other areas of the sub-portions.

Item 39: The electrical lead of any one of the preceding Items, wherein the flexible portions are configured to cause the distal ends to be biased to change course in a particular direction.

Item 40: The electrical lead of any one of the preceding Items, wherein the distal ends are at least partially paddle shaped.

Item 41: The electrical lead of any one of the preceding Items, wherein the sub-portions comprise a shape memory material configured to bend in a predetermined direction when the sub-portions exit a delivery system.

Item 42: The electrical lead of any one of the preceding Items, wherein the sub-portions are further configured to move in a direction opposite the predetermined direction responsive to the shape memory material being heated to body temperature.

Item 43: The electrical lead of any one of the preceding Items, wherein the predetermined direction creates an acute angle shape between the sub-portions and the proximal portion.

Item 44: The electrical lead of any one of the preceding Items, wherein the movement in the direction opposite the predetermined direction creates a ninety degree shape, or an obtuse angle shape between the sub-portions and the proximal portion.

Item 45: The electrical lead of any one of the preceding Items, wherein the sub-portions include distal ends and the distal ends include distal tips that are smaller than the distal ends.

Item 46: The electrical lead of any one of the preceding Items, wherein the sub-portions include distal ends and the distal ends include distal tips that are more rigid compared to other portions of the distal end.

Item 47: The electrical lead of any one of the preceding Items, wherein electrodes are wrapped around the sub-portions that travel in multiple directions during implantation.

Item 48: The electrical lead of any one of the preceding Items, wherein the sub-portions comprise rectangular prisms including two parallel planar surfaces.

Item 49: The electrical lead of any one of the preceding Items, wherein the one or more electrodes wrapped around the sub-portions are elliptical.

Item 50: The electrical lead of any one of the preceding Items, wherein electrode(s) are also wrapped around a proximal part of the distal portion of the lead, which does not travel in a different direction during implantation.

Item 51: The electrical lead of any one of the preceding Items, wherein the electrodes wrapped around the distal portion of the lead comprise pacing electrodes.

Item 52: The electrical lead of any one of the preceding Items, wherein the electrodes wrapped around the distal portion of the lead comprise defibrillation electrodes.

Item 53: The electrical lead of any one of the preceding Items, further comprising pacing electrodes.

Item 54: The electrical lead of any one of the preceding Items, wherein the pacing electrodes are located near distal ends of the sub-portions.

Item 55: The electrical lead of any one of the preceding Items, wherein the pacing electrodes are located on only one of the sub-portions.

Item 56: The electrical lead of any one of the preceding Items, wherein a pacing electrode extends between the sub-portions that travel in multiple directions during implantation.

Item 57: The electrical lead of any one of the preceding Items, wherein electrodes are partially embedded in the sub-portions that travel in multiple directions during implantation, and the partially embedded electrodes have an embedded portion and an exposed portion.

Item 58: The electrical lead of any one of the preceding Items, wherein the sub-portions each comprise two parallel planar surfaces and the exposed portion is on both of the planar parallel surfaces.

Item 59: The electrical lead of any one of the preceding Items, wherein the sub-portions each comprise two parallel planar surfaces and the exposed portion is on only one of the two planar parallel surfaces.

Item 60: The electrical lead of any one of the preceding Items, wherein the partially embedded electrodes are helical coils.

Item 61: The electrical lead of any one of the preceding Items, wherein the exposed portions of the partially embedded electrodes are offset in order to avoid interference when the distal portion of the electrical lead is folded before it splits apart into sub-portions that travel in multiple directions during implantation.

Item 62: The electrical lead of any one of the preceding Items, further comprising concavities on the sub-portions such that exposed portions of the offset electrodes fit within the concavities when the electrical lead is folded.

Item 63: The electrical lead of any one of the preceding Items, wherein the partially embedded electrodes comprise pacing electrodes.

Item 64: The electrical lead of any one of the preceding Items, wherein the partially embedded electrodes comprise defibrillation electrodes.

Item 65: The electrical lead of any one of the preceding Items, further comprising pacing electrodes.

Item 66: The electrical lead of any one of the preceding Items, wherein a central pacing electrode extends between the sub-portions that travel in multiple directions during implantation.

Item 67: The electrical lead of any one of the preceding Items, further comprising one or more suture holes in a proximal part of the distal portion of the lead, which does not travel in a different direction during implantation.

Item 68: The electrical lead of any one of the preceding Items, further comprising one or more grooves or notches on a proximal part of the distal portion of the lead, which does not travel in a different direction during implantation.

Item 69: A delivery system for a component that is a splitting lead having a proximal portion configured to engage a controller and a distal portion configured to split apart into sub-portions that travel in multiple directions during implantation into a patient, the delivery system comprising: a handle configured to be actuated by an operator; a component advancer configured to advance the component into the patient, the component advancer configured to removably engage a portion of the component, the component advancer coupled to the handle and configured to advance the component into the patient by applying a force to the portion of the component in response to actuation of the handle by the operator; and an insertion tip comprising: a first ramp configured to facilitate advancement of a first sub-portion into the patient in a first direction; and a second ramp configured to facilitate advancement of a second sub-portion into the patient in a second direction.

Item 70: The delivery system of any one of the preceding Items, wherein first direction is opposite the second direction.

Item 71: The delivery system of any one of the preceding Items, wherein an angle between the first direction and second direction is approximately 100°.

Item 72: The delivery system of any one of the preceding Items, further comprising a third ramp configured to facilitate advancement of a third sub-portion into the patient in a third direction.

Item 73: The delivery system of any one of the preceding Items, wherein at least the first ramp includes a gap configured to facilitate removal of the delivery system after implantation of the splitting lead.

Item 74: The delivery system of any one of the preceding Items, wherein the gap is wide enough to pass the proximal portion of the splitting lead but also thinner than a width of the sub-portions of the splitting lead so that the sub-portions of the splitting lead engage the first ramp and the second ramp to split apart in multiple directions.

Item 75: The delivery system of any one of the preceding Items, wherein the second ramp is at a more distal location than the first ramp so that advancement of the second sub-portion will be at a location deeper into the patient.

Item 76: The delivery system of any one of the preceding Items, wherein the insertion tip further comprises a tissue-separating component.

Item 77: The delivery system of any one of the preceding Items, wherein the tissue-separating component is wedge-shaped.

Item 78: The delivery system of any one of the preceding Items, wherein the tissue-separating component has a blunted distal end.

Item 79: The delivery system of any one of the preceding Items, wherein the tissue-separating component includes a gap configured to facilitate removal of the delivery system after implantation of the splitting lead.

Item 80: The delivery system of any one of the preceding Items, wherein the insertion tip further includes a movable cover configured to cover the gap.

Item 81: The delivery system of any one of the preceding Items, further comprising the splitting lead, wherein a distal end of the splitting lead includes a gap-filling component configured to fill the gap of the tissue-separating component when the splitting lead is loaded into the delivery system.

Item 82: A method comprising: inserting a lead delivery system into a patient; operating the lead delivery system to advance a lead so that a distal portion of the lead splits apart and travels in multiple directions within the patient.

Item 83: The method any one of the preceding Items, wherein inserting the lead delivery system comprises insertion through an intercostal space associated with the cardiac notch of a patient.

Item 84: The method of any one of the preceding Items, further comprising operating the lead delivery system to place the distal portion of the lead in an extravascular location of the patient.

Item 85: The method of any one of the preceding Items, wherein the extravascular location is in a mediastinum of the patient.

Item 86: The method of any one of the preceding Items, wherein the extravascular location is in a region of a cardiac notch.

Item 87: The method of any one of the preceding Items, wherein the extravascular location is on or near the inner surface of an intercostal muscle.

Item 88: The method of any one of the preceding Items, wherein the distal portion of the lead splits apart into two portions that travel in opposite directions parallel to a sternum of the patient.

Item 89: The method of any one of the preceding Items, wherein the distal portion of the lead splits apart into two portions that travel in directions approximately 100° apart and under a sternum of the patient.

Item 90: The method of any one of the preceding Items, wherein the distal portion of the lead splits apart into three portions that travel in directions approximately 90° apart and parallel or perpendicular to a sternum of the patient.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" (or "computer readable medium") refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" (or "computer readable signal") refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, computer programs and/or articles depending on the desired configuration. Any methods or the logic flows depicted in the accompanying figures and/or described herein do not necessarily require the particular order shown, or sequential order, to achieve desirable results. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The implementations described above can be directed to various combinations and subcombinations of the disclosed features and/or combinations and subcombinations of further features noted above. Furthermore, above described advantages are not intended to limit the application of any issued claims to processes and structures accomplishing any or all of the advantages.

Additionally, section headings shall not limit or characterize the invention(s) set out in any claims that may issue from this disclosure. Further, the description of a technology in the "Background" is not to be construed as an admission that technology is prior art to any invention(s) in this disclosure. Neither is the "Summary" to be considered as a characterization of the invention(s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention(s), and their equivalents, that are protected thereby.

What is claimed is:

1. An electrical lead for implantation in a patient, the lead comprising:
    a distal portion comprising one or more electrodes that are configured to generate therapeutic energy for biological tissue of the patient; and
    a proximal portion coupled to the distal portion and configured to engage a controller, the controller configured to cause the one or more electrodes to generate the therapeutic energy,
    wherein the distal portion is configured to split apart into sub-portions that travel in multiple directions during implantation into the patient, and
    wherein the distal portion is wider than it is thick and the proximal portion is configured to be thinner than the distal portion in a manner that facilitates removal from a delivery system.

2. The electrical lead of claim 1, wherein the one or more electrodes comprise defibrillation electrodes and/or cardiac pacing electrodes.

3. The electrical lead of claim 1, wherein the distal portion is configured to split apart into two sub-portions having a combined length of approximately 6 cm.

4. The electrical lead of claim 1, wherein the sub-portions include distal ends and the distal ends include flexible portions so as to allow the distal ends to change course when encountering sufficient resistance traveling through the biological tissue of the patient.

5. The electrical lead of claim 4, wherein the flexible portions are configured to cause the distal ends to be biased to change course in a particular direction.

6. The electrical lead of claim 4, wherein the flexible portions comprise a material that flexes more easily relative to material of other areas of the sub-portions.

7. The electrical lead of claim 4, wherein the flexible portions comprise one or more cutouts, the one or more cutouts comprising one or more areas having a reduced cross section compared to other areas of the sub-portions.

8. The electrical lead of claim 4, wherein the distal ends are at least partially paddle shaped.

9. The electrical lead of claim 1, wherein the sub-portions comprise a shape memory material configured to bend in a predetermined direction when the sub-portions exit a delivery system.

10. The electrical lead of claim 9, wherein the sub-portions are further configured to move in a direction opposite the predetermined direction responsive to the shape memory material being heated to body temperature.

11. The electrical lead of claim 10, wherein the movement in the direction opposite the predetermined direction creates a ninety degree shape, or an obtuse angle shape between the sub-portions and the proximal portion.

12. The electrical lead of claim 9, wherein the predetermined direction creates an acute angle shape between the sub-portions and the proximal portion.

13. The electrical lead of claim 1, wherein electrode(s) are al-se wrapped around a proximal part of the distal portion of the lead, which does not travel in a different direction during implantation.

14. The electrical lead of claim 13, wherein the electrodes wrapped around the distal portion of the lead comprise defibrillation electrodes, and the electrical lead further comprising pacing electrodes, wherein the pacing electrodes are located near distal ends of the sub-portions.

15. The electrical lead of claim 13, wherein the electrodes wrapped around the distal portion of the lead comprise defibrillation electrodes, and the electrical lead further comprising pacing electrodes, wherein the pacing electrodes are located on only one of the sub-portions.

16. The electrical lead of claim 1, wherein a central pacing electrode extends between the sub-portions that travel in multiple directions during implantation.

17. The electrical lead of claim 1, wherein electrodes are partially embedded in the sub-portions that travel in multiple directions during implantation, and the partially embedded electrodes have an embedded portion and an exposed portion.

18. The electrical lead of claim 17, wherein the exposed portions of the partially embedded electrodes are offset in order to avoid interference when the distal portion of the electrical lead is folded before it splits apart into sub-portions that travel in multiple directions during implantation.

19. The electrical lead of claim 18, further comprising concavities on the sub-portions such that exposed portions of the offset electrodes fit within the concavities when the electrical lead is folded.

20. The electrical lead of claim 17, wherein a central pacing electrode extends between the sub-portions that travel in multiple directions during implantation.

21. The electrical lead of claim 17, wherein the sub-portions each comprise two parallel planar surfaces and the exposed portion is on only one of the two planar parallel surfaces.

22. The electrical lead of claim 17, wherein the partially embedded electrodes are helical coils.

23. The electrical lead of claim 1, further comprising one or more suture holes in a proximal part of the distal portion of the lead, which does not travel in a different direction during implantation.

24. The electrical lead of claim 1, further comprising one or more grooves or notches on a proximal part of the distal portion of the lead, which does not travel in a different direction during implantation.

25. The electrical lead of claim 1, wherein the distal portion is configured to split apart into two sub-portions having different lengths.

26. The electrical lead of claim 1, wherein the distal portion is configured to split apart into two sub-portions comprising 60% and 40% respectively of their total combined length.

27. The electrical lead of claim 1, wherein the sub-portions comprise parallel planar surfaces.

28. The electrical lead of claim 1, wherein the sub-portions include distal ends and the distal ends include distal tips that are more rigid compared to other portions of the distal end.

29. The electrical lead of claim 1, wherein electrodes are wrapped around the sub-portions that travel in multiple directions during implantation, the sub-portions comprise rectangular prisms including two parallel planar surfaces, and the one or more electrodes wrapped around the sub-portions are elliptical.

30. An electrical lead for implantation in a patient, the lead comprising:
a distal portion comprising one or more electrodes that are configured to generate therapeutic energy for biological tissue of the patient;
a proximal portion coupled to the distal portion and configured to engage a controller, the controller configured to cause the one or more electrodes to generate the therapeutic energy, wherein the distal portion is configured to split apart into sub-portions that travel in multiple directions during implantation into the patient; and
one or more suture holes in a proximal part of the distal portion of the lead, which does not travel in a different direction during implantation.

31. The electrical lead of claim 30, wherein the one or more electrodes comprise defibrillation electrodes and/or cardiac pacing electrodes.

32. The electrical lead of claim 30, wherein the distal portion is configured to split apart into two sub-portions having a combined length of approximately 6 cm.

33. The electrical lead of claim 30, wherein the sub-portions include distal ends and the distal ends include flexible portions so as to allow the distal ends to change course when encountering sufficient resistance traveling through the biological tissue of the patient.

34. The electrical lead of claim 33, wherein the flexible portions are configured to cause the distal ends to be biased to change course in a particular direction.

35. The electrical lead of claim 33, wherein the flexible portions comprise a material that flexes more easily relative to material of other areas of the sub-portions.

36. The electrical lead of claim 33, wherein the flexible portions comprise one or more cutouts, the one or more cutouts comprising one or more areas having a reduced cross section compared to other areas of the sub-portions.

37. The electrical lead of claim 33, wherein the distal ends are at least partially paddle shaped.

38. The electrical lead of claim 30, wherein the sub-portions comprise a shape memory material configured to bend in a predetermined direction when the sub-portions exit a delivery system.

39. The electrical lead of claim 38, wherein the sub-portions are further configured to move in a direction opposite the predetermined direction responsive to the shape memory material being heated to body temperature.

40. The electrical lead of claim 39, wherein the movement in the direction opposite the predetermined direction creates a ninety degree shape, or an obtuse angle shape between the sub-portions and the proximal portion.

41. The electrical lead of claim 38, wherein the predetermined direction creates an acute angle shape between the sub-portions and the proximal portion.

42. The electrical lead of claim 30, wherein electrode(s) are wrapped around a proximal part of the distal portion of the lead, which does not travel in a different direction during implantation.

43. The electrical lead of claim 42, wherein the electrodes wrapped around the distal portion of the lead comprise defibrillation electrodes, and the electrical lead further comprising pacing electrodes, wherein the pacing electrodes are located near distal ends of the sub-portions.

44. The electrical lead of claim 42, wherein the electrodes wrapped around the distal portion of the lead comprise defibrillation electrodes, and the electrical lead further comprising pacing electrodes, wherein the pacing electrodes are located on only one of the sub-portions.

45. The electrical lead of claim 30, wherein a central pacing electrode extends between the sub-portions that travel in multiple directions during implantation.

46. The electrical lead of claim 30, wherein electrodes are partially embedded in the sub-portions that travel in multiple directions during implantation, and the partially embedded electrodes have an embedded portion and an exposed portion.

47. The electrical lead of claim 46, wherein the exposed portions of the partially embedded electrodes are offset in order to avoid interference when the distal portion of the electrical lead is folded before it splits apart into sub-portions that travel in multiple directions during implantation.

48. The electrical lead of claim 47, further comprising concavities on the sub-portions such that exposed portions of the offset electrodes fit within the concavities when the electrical lead is folded.

49. The electrical lead of claim 46, wherein a central pacing electrode extends between the sub-portions that travel in multiple directions during implantation.

50. The electrical lead of claim 46, wherein the sub-portions each comprise two parallel planar surfaces and the exposed portion is on only one of the two planar parallel surfaces.

51. The electrical lead of claim 46, wherein the partially embedded electrodes are helical coils.

52. The electrical lead of claim 30, further comprising one or more grooves or notches on a proximal part of the distal portion of the lead, which does not travel in a different direction during implantation.

53. The electrical lead of claim 30, wherein the distal portion is configured to split apart into two sub-portions having different lengths.

54. The electrical lead of claim 30, wherein the distal portion is configured to split apart into two sub-portions comprising 60% and 40% respectively of their total combined length.

55. The electrical lead of claim 30, wherein the sub-portions comprise parallel planar surfaces.

56. The electrical lead of claim 30, wherein the sub-portions include distal ends and the distal ends include distal tips that are more rigid compared to other portions of the distal end.

57. The electrical lead of claim 30, wherein electrodes are wrapped around the sub-portions that travel in multiple directions during implantation, the sub-portions comprise rectangular prisms including two parallel planar surfaces, and the one or more electrodes wrapped around the sub-portions are elliptical.

* * * * *